US009974882B2

(12) United States Patent
Machida et al.

(10) Patent No.: US 9,974,882 B2

(45) Date of Patent: May 22, 2018

(54) DUST REDUCER CONSISTING OF MULTI-COMPONENT METAL COMPOUND, WATER ABSORBING AGENT CONTAINING MULTI-COMPONENT METAL COMPOUND, AND METHOD FOR PRODUCING THE SAME

(71) Applicant: Nippon Shokubai Co., Ltd., Osaka (JP)

(72) Inventors: Sayaka Machida, Hyogo (JP); Hiroyuki Ikeuchi, Hyogo (JP); Taishi Kobayashi, Hyogo (JP); Mariko Tamaki, Hyogo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 136 days.

(21) Appl. No.: 14/432,446

(22) PCT Filed: Oct. 1, 2013

(86) PCT No.: PCT/JP2013/076739

§ 371 (c)(1),
(2) Date: Mar. 30, 2015

(87) PCT Pub. No.: WO2014/054656

PCT Pub. Date: Apr. 10, 2014

(65) Prior Publication Data

US 2015/0258237 A1 Sep. 17, 2015

(30) Foreign Application Priority Data

Oct. 1, 2012 (JP) ................................. 2012-219517
Sep. 5, 2013 (JP) ................................. 2013-184485
Sep. 5, 2013 (JP) ................................. 2013-184487

(51) Int. Cl.

| | |
|---|---|
| ***B01J 20/04*** | (2006.01) |
| ***A61L 15/60*** | (2006.01) |
| ***C08L 33/02*** | (2006.01) |
| ***B01J 20/26*** | (2006.01) |
| ***C08J 3/24*** | (2006.01) |
| ***A61L 15/18*** | (2006.01) |
| ***A61L 15/26*** | (2006.01) |
| ***A61L 15/42*** | (2006.01) |
| ***A61L 15/56*** | (2006.01) |
| ***C09K 3/22*** | (2006.01) |
| ***G01N 31/00*** | (2006.01) |

(52) U.S. Cl.

CPC ............... *A61L 15/60* (2013.01); *A61L 15/18* (2013.01); *A61L 15/26* (2013.01); *A61L 15/42* (2013.01); *A61L 15/56* (2013.01); *B01J 20/041* (2013.01); *B01J 20/267* (2013.01); *C08J 3/245* (2013.01); *C08L 33/02* (2013.01); *C09K 3/22* (2013.01); *G01N 31/00* (2013.01); *B01J 2220/46* (2013.01); *B01J 2220/68* (2013.01); *C08J 2333/02* (2013.01)

(58) Field of Classification Search

CPC .............................. B01J 20/041; B01J 20/267
See application file for complete search history.

(56) References Cited

U.S. PATENT DOCUMENTS

| | | | |
|---|---|---|---|
| 4,735,987 | A | 4/1988 | Morita et al. |
| 2011/0003926 | A1 | 1/2011 | Nogi et al. |

FOREIGN PATENT DOCUMENTS

| | | |
|---|---|---|
| CN | 101392038 | 3/2009 |
| EP | 1840157 | 10/2007 |
| JP | A-S62-223203 | 10/1987 |
| JP | 2-215863 | 8/1990 |
| JP | 7-242709 | 9/1995 |
| JP | 2003-525105 | 8/2003 |
| WO | WO-1997/030109 | 8/1997 |
| WO | WO-2000/010619 | 3/2000 |
| WO | WO 01/32117 | 5/2001 |
| WO | WO-2009/005114 | 1/2009 |

OTHER PUBLICATIONS

Extended European Search Report Issued in EP 13843510.2 dated Jul. 12, 2016.

*Primary Examiner* — Paul West

(74) *Attorney, Agent, or Firm* — Cesari and McKenna, LLP

(57) ABSTRACT

[Problem] To provide a dust reducer which suppresses blocking against moisture absorption and has a reduced amount of dust generation, without impairing the water absorption physical properties that are required from a water absorbing agent, such as water absorption capacity under load; a method for producing a water absorbing agent using the dust reducer; and a water absorbing agent in which blocking against moisture absorption is suppressed and which has a reduced amount of dust generation. [Solution] A dust reducer for a water absorbing agent containing a surface crosslinked polyacrylic acid (salt)-based water absorbent resin as a main component, wherein the dust reducer is a multi-component metal compound which has a hydrotalcite structure and contains a hydroxyl group and two kinds of metal cations that are divalent and trivalent.

12 Claims, No Drawings

DUST REDUCER CONSISTING OF MULTI-COMPONENT METAL COMPOUND, WATER ABSORBING AGENT CONTAINING MULTI-COMPONENT METAL COMPOUND, AND METHOD FOR PRODUCING THE SAME

CROSS REFERENCE TO RELATED APPLICATIONS

This application is the National Stage of International Application No. PCT/JP2013/076739, filed on Oct. 1, 2013, which claims the benefit of Japanese Application Nos. 2012/219515, filed on Oct. 1, 2012, 2013-184485, filed on Sep. 5, 2013, and 2013-184487, filed on Sep. 5, 2013. The contents of all prior applications are hereby incorporated by reference in their entirety.

TECHNICAL FIELD

The present invention relates to a dust reducer for a water absorbing agent used in hygienic materials such as paper diapers, sanitary napkins, and so-called incontinence pads, and to a water absorbing agent containing a multi-component metal compound, and a method for producing the same.

BACKGROUND ART

Since water absorbent resin particles lose fluidity as a result of moisture absorption, various investigations have been made, and a known representative method is a method of adding inorganic particles of clay, silica or the like. However, in this method, the added fine particles become dust and cause deterioration in the work environment, and the added fine particles cause a decrease in the water absorbent performance such as the water absorption capacity under load.

For that reason, a method of adding and wet mixing inorganic particles in the form of slurry, and a method of adding a coating agent such as a polymer have also be suggested; however, there have been limitations on the amount of addition and the like, because the water itself that is used for the addition causes a decrease in fluidity, or in order to avoid deterioration in the performance of the water absorbent resin particles by addition of the coating agent.

WO 00/10619 discloses a super absorbent polymer (SAP) which has a coagulation preventive function provided by addition of kaolin and has a reduced amount of dust. Specifically, disclosed is a super absorbent polymer obtained by adding 0.5% to 3% by mass of kaolin to a particulate SAP precursor material, followed by addition of a surface cross-linking aqueous solution containing ethylene carbonate thereto and heating of the mixture; by adding an aqueous solution containing kaolin in an amount of 2% to 3% by mass relative to the super absorbent polymer after a heating treatment; and by adding a surface crosslinking aqueous solution containing kaolin, followed by a heating treatment. The coagulation preventive function is dependent on the amount of addition of kaolin, and it is known that the coagulation preventive function is low at 0.5% by mass. Furthermore, in a qualitative dust evaluation, a tendency that the coagulation preventive function depends on the amount of addition of kaolin is observed. Also, in a method in which an aqueous solution containing kaolin is not added after surface crosslinking, the AUL is decreased.

Japanese Patent Application Laid-Open (JP-A) No. 62-223203 discloses a method for producing a highly swellable water absorbent polymer that is crosslinked using a crosslinking agent in the presence of a binary metal hydroxide having an anion exchange capability. Specifically, a highly swellable polymer which has a high water-absorbing speed, does not show stickiness after water absorption, and has gas permeability is obtained by adding hydrotalcite in an amount of about 5% to 20% by mass and a crosslinking agent to a water absorbent resin particle-containing solution obtained by reverse phase suspension polymerization, and performing azeotropic dehydration. According to the relevant patent document, it is described that co-presence of hydrotalcite at the time of the crosslinking reaction is essential, and simple mixing is not so effective. Regarding the reason for this, as a result of IR and X-ray analyses of the polymer thus obtained, it is speculated that a completely new composite has been formed, unlike the case of simple mixing.

WO 97/030109 discloses a method for controlling dust by physical coating with a hydrophobic organic anti-dusting agent; however, hydrophobic organic anti-dusting agents have problems such as a decrease in the water-absorbing speed because the surface of the water absorbing agent become hydrophobic.

Additives for imparting hygroscopic fluidity have problems such as generation of dust and deterioration in the water absorption performance such as a decrease in the water absorption capacity under load or the water-absorbing speed.

Therefore, there is a demand for an additive which suppresses blocking against moisture absorption without impairing the water absorption performance, suppresses the generation of dust, and has fewer restrictions on the production method.

SUMMARY OF INVENTION

Technical Problem

An object of the present invention is to provide a dust reducer which suppresses blocking against moisture absorption without impairing the water absorption physical properties required for a water absorbing agent, such as the water absorption capacity under load, and also has a reduced amount of dust generation; a method for producing a water absorbing agent using the dust reducer; and a water absorbing agent which has blocking against moisture absorption suppressed and has a reduced amount of dust generation. Another object of the present invention is to provide a water absorbing agent which is improved decreased urine resistance and resistance to coloration with the lapse of time, when an inorganic compound having a hydrotalcite structure and containing divalent and trivalent metal cations and a hydroxyl group is used.

Means for Solving Problem

The inventors of the present invention conducted a thorough investigation in order to solve the problems described above, and as a result, the inventors found that an inorganic compound having a hydrotalcite structure and containing divalent and trivalent metal cations and a hydroxyl group (hereinafter, may be referred to as multi-component metal compound) has an effect of reducing the amount of dust itself of a water absorbing agent. Furthermore, the inventors found that the reducing effect is effective not only in decreasing dust generation of a water absorbing agent including the multi-component metal compound and a water absorbent resin powder, but also in suppressing the amount of the dust generation caused by addition of other inorganic fine particles. Furthermore, the inventors elucidated that the cause of the decrease in urine resistance and the decrease in the resistance to coloration with the lapse of time is the influence exerted by the divalent metal in the multi-component metal compound, particularly magnesium ion ($Mg^{2+}$), and found that the problems are ameliorated by adding a chelating agent.

Moreover, the inventors found that the multi-component metal compound exhibits an effect of reducing the amount of dust generation only by dry mixing, and a surprising effect that the multi-component metal compound exhibits gel blocking reducing action with a small amount of the compound, without decreasing the water absorption physical properties such as the water absorption capacity under load, can be obtained. Thus, the inventors completed the present invention.

The dust reducer of the present invention is a multi-component metal compound containing a hydroxyl group and two kinds of metal cations that are divalent and trivalent, which decreases dust generation of a water absorbing agent including a surface-cross-linked polyacrylic acid (salt)-based water absorbent resin as a main component.

DESCRIPTION OF EMBODIMENTS

Furthermore, it is more preferable that the divalent and trivalent metal cations of the multi-component metal compound are cations of magnesium and aluminum, respectively (hereinafter, may be referred to as HT compound).

An embodiment of the method for producing a water absorbing agent of the present invention includes a surface cross-linking step; and a multi-component metal compound addition step of adding a multi-component metal compound which has a hydrotalcite structure and contains a hydroxyl group and two kinds of metal cations that are divalent and trivalent, to a polyacrylic acid (salt)-based water absorbent resin powder in an amount of 0.01% to 5% by mass, preferably 0.01% to 3% by mass, and more preferably 0.01% to 1% by mass.

In regard to the multi-component metal compound addition step, it is preferable that the water absorbent resin powder and the multi-component metal compound are dry mixed, and it is more preferable that the surface cross-linking step is carried out in a preceding step and/or a subsequent step of the multi-component metal compound addition step.

According to a suitable embodiment of the water absorbing agent of the present invention, the multi-component metal compound is included in an amount of 0.01% to 5% by mass, more preferably 0.01% to 3% by mass, and still more preferably 0.01% to 1% by mass, and the blocking ratio against moisture absorption is 0% to 30% by mass. Furthermore, according to a suitable embodiment of the water absorbing agent of the present invention, the water absorbing agent is obtained by the production method described above, and the blocking ratio against moisture absorption is 0% to 30% by mass. Such a water absorbing agent has high water absorption performance.

The multi-component metal compound related to the present invention not only reduces dust of a water absorbing agent including the multi-component metal compound and a water absorbent resin powder, but also has an ability to reduce the dust increased by adding inorganic fine particles other than the multi-component metal compound. Furthermore, since a third component needed to add the multi-component metal compound, for example, water, is not needed, the production process is simplified, and there is no need to consider the influence exerted by the third component. Furthermore, only by dry mixing, high adhesiveness is obtained, and the multi-component metal compound itself exhibits a high blocking against moisture absorption effect even if used in a small amount, and does not impair the water absorption performance.

A water absorbing agent containing the multi-component metal compound produces a less amount of dust, does not easily cause blocking against moisture absorption, and has high water absorption performance. Therefore, in the production process for the water absorbing agent and the production process for an absorbent body using the water absorbing agent, deterioration of the work environment caused by dust scattering or the like is suppressed.

Hereinafter, the present invention will be described in detail; however, the scope of the present invention can be appropriately modified, without being restricted by these descriptions, to the extent that the gist of the present invention is maintained even in examples other than the following illustrated examples. Furthermore, in the present invention, weight and mass, percent (%) by weight and percent (%) by mass, and parts by weight and parts by mass may be respectively used in an interchangeable manner, and the usage in the descriptions will be uniformly set to mass, percent (%) by mass, and parts by mass.

[1] DEFINITIONS OF TERMS

(1-1) Water Absorbing Agent

According to the present specification, the term "water absorbing agent" is a gelling agent for an aqueous liquid, which contains a water absorbent resin as a main component and is obtained by subjecting the water absorbent resin to a surface cross-linking step and a multi-component metal addition step. Here, the term "main component" implies that the content of the water absorbent resin in a water absorbing agent is 70% by mass or more of the water absorbing agent, and the content is preferably 80% by mass or more, and still more preferably 90% by mass or more (the upper limit is 99.99% by mass). A water absorbing agent includes a multi-component metal compound in addition to the water absorbent resin, and in addition to them, the water absorbing agent may further include inorganic fine particles, a cationic polymer compound, a water-soluble polyvalent metal cation-containing compound, a surfactant, a coloration preventing agent, a urine resistance improving agent, a deodorizer, a fragrance, an antimicrobial agent, a foaming agent, a pigment, a dye, a fertilizer, an oxidizing agent, a reducing agent and the like, respectively in an amount of 0% to 10% by mass, and preferably 0.1% to 1% by mass.

(1-2) Surface Crosslinked Water Absorbent Resin

According to the present specification, the "surface cross-linked water absorbent resin" is a gelling agent for an aqueous solution, which is obtained by subjecting a water absorbent resin to a surface cross-linking step, and even in a case in which the resin is obtained by carrying out a surface cross-linking step after a surface crosslinking agent addition step and a multi-component metal compound addition step, the resin is referred to as a surface crosslinked water absorbent resin.

(1-3) Polyacrylic Acid (Salt)-Based Water Absorbent Resin

According to the present specification, a water absorbent resin means a water-swellable, water-insoluble polymer gelling agent. Furthermore, the term "water-swellable"

means that the CRC (absorption capacity without load) defined by ERT441.2-02 is 5 [g/g] or more, and the term "water-insoluble" means that the Extr (water soluble component) defined by ERT470.2-02 is 0% to 50% by mass.

Furthermore, the water absorbent resin is not intended to be limited such that the entire amount (100% by mass) be is composed of polymers, and the water absorbent resin may include additives and the like to the extent that the performance described above is maintained. In the present invention, a water absorbent resin composition containing a small amount of additives is also collectively referred to as a water absorbent resin. Furthermore, examples of the shape of the water absorbent resin include a sheet form, a fiber form, a film form, and a gel form; however, a powder form is preferred, while a water absorbent resin in the form of a powder having the particle size or moisture content described below is particularly preferred. This may also be referred to as a water absorbent resin powder.

The term "polyacrylic acid (salt)-based water absorbent resin" according to the present specification means a polymer which optionally contains a graft component, and contains, as a repeating unit, acrylic acid and/or a salt thereof (hereinafter, referred to as acrylic acid (salt)) as a main component.

Specifically, the polyacrylic acid (salt)-based water absorbent resin refers to a polymer which contains 50 mol % to 100 mol % of acrylic acid (salt) among all the monomers used in polymerization (excluding crosslinking agents), and refers to a water absorbent resin containing preferably 70 mol % to 100 mol %, more preferably 90 mol % to 100 mol %, and particularly preferably substantially 100 mol %, of acrylic acid (salt). Furthermore, according to the present invention, a polyacrylic acid salt type (neutralized type) polymer is also collectively referred to as a polyacrylic acid (salt)-based water absorbent resin.

(1-4) "EDANA" and "ERT"

The term "EDANA" is the abbreviation for the European Disposables and Nonwovens Associations, and the term "ERT" is the abbreviation for a method for analyzing a water absorbent resin (EDANA Recommended Test Methods), which is a European standard. Meanwhile, according to the present invention, unless particularly stated otherwise, the physical properties of a water absorbent resin are measured according to the original document of ERT (published document: revised in 2002).

(a) "CRC" (ERT441.2-02)

The term "CRC" is the abbreviation for Centrifuge Retention Capacity, and means the absorption capacity without load (hereinafter, also referred to as "absorption capacity"). Specifically, the CRC is the absorption capacity (unit: [g/g]) obtained after 0.200 g of a water absorbent resin in a non-woven fabric bag is allowed to freely swell for 30 minutes in a large excess of a 0.9% by mass aqueous solution of sodium chloride (physiological saline), and then is dehydrated at 250 G using a centrifuge.

(b) "AAP" (ERT442.2-02)

The term "AAP" is the abbreviation for the Absorption Against Pressure, and means the absorption capacity under load. Specifically, the AAP is the absorption capacity (unit: [g/g]) obtained after 0.900 g of a water absorbent resin is allowed to swell in a 0.9% by mass aqueous solution of sodium chloride (physiological saline) for one hour under a load of 2.06 kPa (0.3 psi).

(c) "PSD" (ERT420.2-02)

The term "PSD" is the abbreviation for the Particle Size Distribution, and means the particle size distribution measured by sieve classification. Meanwhile, the mass average particle size (D50) and the particle size distribution width are measured by the same method as that for the "Average Particle Diameter and Distribution of Particle Diameter" described in European Patent No. 0349240.

(1-5) Others

According to the present specification, the expression "X to Y" that indicates a range means "equal to or more than X and equal to or less than Y." Furthermore, the unit of mass "t (ton)" means "metric ton", and unless particularly stated otherwise, the unit "ppm" means "ppm by mass". Furthermore, the term "-acid (salt)" means "-acid and/or a salt thereof", and "(meth)acryl" means "acryl and/or methacryl". In regard to the measurement of physical properties and the like, unless particularly stated otherwise, the measurement is made at room temperature (20° C. to 25° C.) and a relative humidity of 40 to 50% RH.

[2] POLYACRYLIC ACID (SALT)-BASED WATER ABSORBENT RESIN POWDER AND METHOD FOR PRODUCING WATER ABSORBING AGENT

The method for producing a water absorbing agent of the present invention includes a surface cross-linking step; and a multi-component metal compound addition step of adding a multi-component metal compound which is an inorganic compound containing a hydroxyl group and two kinds of metal cations that are divalent and trivalent to a polyacrylic acid (salt)-based water absorbent resin powder in an amount of 0.01% to 3% by mass. The surface cross-linking step and the multi-component metal compound addition step will be illustrated below, and suitable exemplary embodiments of the water absorbent resin powder and the method for producing a water absorbing agent will also be described.

Meanwhile, the water absorbent resin powder to which the multi-component metal compound is added, may be present before or after surface cross-linked. That is, the water absorbent resin powder to which the multi-component metal compound is added may be a surface crosslinked water absorbent resin powder.

(2-1) Step for Preparing Aqueous Solution of Acrylic Acid (Salt)-Based Monomer

According, to the present specification, the term "aqueous solution of an acrylic acid (salt)-based monomer" is a monomer aqueous solution including acrylic acid (salt) as a main component. The relevant aqueous solution refers to a formulation of components that constitute a water absorbent resin powder, such as a crosslinking agent, a graft component, and trace components (a chelating agent, a surfactant, a dispersant and the like) as necessary, and means an aqueous solution supplied to polymerization after a polymerization initiator is added to the formulation as received.

The acrylic acid (salt) may be unneutralized, or may be in a salt form (a completely neutralized form or a partially neutralized form). Also, the monomer aqueous solution may have a concentration exceeding the saturation concentration, or may be a hypersaturated aqueous solution or aqueous slurry solution (aqueous dispersion liquid) of acrylic acid (salt), and these are handled as the aqueous solution of an acrylic acid (salt)-based monomer of the present invention. From the viewpoint of the physical properties of the water absorbent resin powder thus obtainable, it is preferable to use an aqueous solution of an acrylic acid (salt)-based monomer at a concentration less than or equal to the saturation concentration.

Furthermore, the solvent for the monomer is preferably water, and the acrylic acid (salt)-based monomer is handled as an aqueous solution. Here, regarding the term "aqueous solution", it is not limited such that 100% by mass of the solvent should be water, and 0% to 30% by mass, and preferably 0% to 5% by mass, of a water-soluble organic solvent (for example, an alcohol) may be used in combination. In the present invention, these are regarded as aqueous solutions.

According to the present specification, the term "aqueous solution of an acrylic acid (salt)-based monomer in the middle of preparation" refers to an aqueous solution of acrylic acid (salt) before all the constituent components are incorporated into the above-described monomer aqueous solution containing acrylic acid (salt) as a main component, and specifically, an aqueous solution of acrylic acid, or a completely neutralized or partially neutralized aqueous solution of an acrylic acid salt corresponds to the relevant term.

When the aqueous solution of an acrylic acid (salt)-based monomer in the middle of preparation is further neutralized, water as a solvent is incorporated therein, the trace components described above, or the like are incorporated therein, the final aqueous solution of an acrylic acid (salt)-based monomer is obtained. Meanwhile, in regard to this final aqueous solution of an acrylic acid (salt)-based monomer, the state before the aqueous solution is introduced into a polymerization apparatus, or the state after the aqueous solution has been introduced into a polymerization apparatus but before polymerization is initiated, is referred to as an "aqueous solution of an acrylic acid (salt)-based monomer after the preparation before the polymerization step."

(Monomer)

The monomer used is not particularly limited as long as the monomer which forms a water absorbent resin by polymerization, and examples thereof include anionic unsaturated monomers (salts) such as (meth)acrylic acid, maleic acid (anhydride), itaconic acid, cinnamic acid, vinylsulfonic acid, allyltoluenesulfonic acid, vinyltoluenesulfonic acid, styrenesulfonic acid, 2-(meth)acrylamido-2-methylpropanesulfonic acid, 2-(meth)acryloylethanesulfonic acid, 2-(meth)acryloylpropanesulfonic acid, and 2-hydroxyethyl(meth)acryloylphosphate; mercapto group-containing unsaturated monomers; phenolic hydroxyl group-containing unsaturated monomers; amide group-containing unsaturated monomers such as (meth)acrylamide, N-ethyl(meth)acrylamide, and N,N-dimethyl(meth)acrylamide; amino group-containing unsaturated monomers such as N,N-dimethylaminoethyl(meth)acrylate, N,N-dimethylaminopropyl(meth) acrylate, and N,N-dimethylaminopropyl(meth)acrylamide; and the like. These monomers may be used singly, or may be used in combination of two or more kinds.

The content (amount of use) of the acrylic acid (salt) is usually 50% by mole or more, preferably 70% by mole or more, more preferably 80% by mole or more, still more preferably 90% by mole or more, and particularly preferably 95% by mole or more (the upper limit is 100% by mole), relative to the total amount of the monomers (excluding an internal crosslinking agent). Meanwhile, the polyacrylic acid (salt) according to the present invention is a concept which is not limited to unneutralized polymer (neutralization rate: 0% by mole) and includes partially neutralized or completely neutralized (neutralization rate: 100% by mole).

According to the present invention, the neutralization rate of the acrylic acid (salt)-based monomer or a water-containing gel-like crosslinked polymer obtained after polymerization is not particularly limited; however, from the viewpoints of the physical properties of the resulting water absorbent resin powder and the reactivity of the surface crosslinking agent, the neutralization rate is preferably 40% to 90% by mole, and more preferably 50% to 80% by mole.

However, when the neutralization rate is low, the water-absorbing speed (for example, FSR or Vortex) tends to be decreased. On the contrary, when the neutralization rate is high, the reactivity between the polyacrylic acid (salt)-based water absorbent resin powder and the surface crosslinking agent, particularly an alkylene carbonate, is decreased, and productivity tends to be decreased, or the liquid permeability (for example, SFC) or the absorption capacity under load (for example, AAP or PUP) tends to be decreased. Therefore, a neutralization rate in the above-described range is preferred. Furthermore, neutralization after polymerization is not needed for the applications in which there is a possibility for the product to be brought into contact with the human body, such as paper diapers.

Also, from the viewpoints of the absorption capacity without load (CRC) or the absorption capacity under load (AAP) of the water absorbing agent obtainable as a final product, the acrylic acid (salt)-based monomer or a water-containing gel-like crosslinked polymer is such that a portion or the entirety may be in a salt form, and monovalent salts such as sodium salt, lithium salt, potassium salt, ammonium salt, and amines are preferred. Among others, alkali metal salts are more preferred, sodium salt and/or potassium salt is still more preferred, and from the viewpoints of the cost and physical properties, sodium salt is particularly preferred.

(Polymerization Inhibitor)

The acrylic acid (salt)-based monomer may include a polymerization inhibitor. The polymerization inhibitor is not particularly limited; however, examples thereof include the N-oxyl compounds disclosed in WO 2008/096713, manganese compounds, substituted phenol compounds, and the like. Among them, substituted phenols are preferred, and methoxyphenols are particularly preferred.

Examples of the methoxyphenols include o-, m- or p-methoxyphenol, methoxyphenols having one or two or more substituents such as a methyl group, a t-butyl group and a hydroxyl group, and the like; however, in the present invention, p-methoxyphenol is particularly preferred.

Furthermore, the content of the polymerization inhibitor in the acrylic acid (salt)-based monomer is preferably 10 to 200 ppm, and is more preferably 5 to 160 ppm, 10 to 160 ppm, 10 to 100 ppm, and 10 to 80 ppm in this order, while the content is most preferably 10 to 70 ppm. When the content is 10 to 200 ppm, deterioration of the color hue (coloration known as yellow tint or yellowing) of the resulting water absorbing agent is reduced, and when the polymerization inhibitor is removed by purification such as distillation, there is a reduced risk of causing unintended polymerization.

(Internal Crosslinking Agent)

The monomer aqueous solution may include an internal crosslinking agent as necessary. Regarding the internal crosslinking agent, any known agent can be used, and examples thereof include N,N'-methylenebis(meth)acrylamide, (poly)ethylene glycol di(meth)acrylate, (poly) propylene glycol di(meth)acrylate, trimethylolpropane tri(meth) acrylate, glycerin tri(meth)acrylate, glycerin acrylate methacrylate, ethylene oxide-modified trimethylolpropane tri(meth)acrylate, pentaerythritol hexa(meth)acrylate, triallyl cyanurate, triallyl isocyanurate, triallyl phosphate, triallylamine, poly(meth)allyloxyalkane, (poly)ethylene glycol diglycidyl ether, glycerol diglycidyl ether, ethylene glycol, polyethylene glycol, propylene glycol, glycerin, 1,4-butanediol, pentaerythritol, ethylenediamine, ethylene carbonate, propylene carbonate, polyethyleneimine, glycidyl(meth) acrylate, and the like. Among these, one kind or two or more kinds may be used in consideration of reactivity, and among others, it is preferable to use a compound having two or more polymerizable unsaturated groups.

Furthermore, when two or more kinds of internal cross-linking agents are used in combination, since the internal crosslinked structure can be modified by changing the reactivity of the functional groups thereof, it is preferable to select internal crosslinking agents having different functional groups from the compounds exemplified above, including amide compounds, (meth)acrylate compounds, allyl compounds, amine compounds, imine compounds, alcohol compounds, carbonate compounds and glycidyl compounds, and use them in combination.

The amount of use of the internal crosslinking agent can be appropriately determined in accordance with desired physical properties of the water absorbing agent; however, the amount of use is preferably 0.001% to 5% by mole, more preferably 0.005% to 2% by mole, and still more preferably 0.01% to 1% by mole, relative to the total amount of the acrylic acid (salt)-based monomer. Furthermore, in a case in which two or more kinds of the internal crosslinking agents are used in combination, the amount of use of each of the internal crosslinking agents is preferably 0.001% to 5% by mole, more preferably 0.005% to 2% by mole, and still more preferably 0.01% to 1% by mole, relative to the total amount of the acrylic acid (salt)-based monomer.

When this amount of use (in the case of using two or more kinds in combination, the total amount) is 0.001% to 5% by mole, the amount of water soluble components of the resulting water absorbing agent is low, and a sufficient amount of water absorption under load can be secured. Also, an appropriate crosslinking density of the resulting water absorbing agent is obtained, and a sufficient amount of water absorption is obtained. Meanwhile, regarding the internal crosslinking agent, the entire amount may be added to the aqueous solution of the acrylic acid (salt)-based monomer obtained after the preparation before the polymerization step, or a portion thereof may be added after the initiation of polymerization.

(2-2) Aqueous Solution Polymerization Step (Polymerization Method)

Examples of the polymerization method for obtaining a water absorbent resin powder include spray polymerization, droplet polymerization, bulk polymerization, precipitation polymerization, aqueous solution polymerization, reverse phase suspension polymerization, and the like; however, aqueous solution polymerization of using monomers in the form of an aqueous solution is suitably used.

The aqueous solution polymerization is a method of polymerizing a monomer aqueous solution without using a dispersing solvent, and the method is disclosed in, for example, U.S. Pat. Nos. 4,625,001, 4,873,299, 4,286,082, 4,973,632, 4,985,518, 5,124,416, 5,250,640, 5,264,495, 5,145,906 and 5,380,808; European Patent Nos. 0811636, 0955086 and 0922717, etc.

There are no particular limitations on the concentration of the monomer aqueous solution at the time of the polymerization; however, the concentration is preferably from 20% by mass to the saturation concentration, more preferably 25% to 80% by mass, and still more preferably 30% to 70% by mass. When the concentration is 20% by mass or more, a decrease in productivity can be suppressed. Meanwhile, since polymerization in the state of slurry of the monomer (aqueous dispersion liquid of an acrylic acid salt) may bring about deterioration in the physical properties, it is preferable to perform polymerization at a concentration less than or equal to the saturation concentration (see; JP-A No. 1-318021).

Furthermore, in order to accelerate polymerization and enhance the physical properties, a degassing process for dissolved oxygen (for example, purging process with an inert gas) may also be provided as necessary at the time of polymerization. In addition to that, for the purpose of achieving an increase in the water-absorbing speed, an increase in the surface area, an increase in the drying rate, and the like, gas bubbles (particularly, of an inert gas) or various foaming agents (for example, organic or inorganic carbonates, azo compounds, and urea compounds) may be incorporated at the time of polymerization, and foaming may be induced to obtain, for example, a volume 1.001 to 10 times the original volume at the time of polymerization or at the time of drying.

The polymerization step according to the present invention can be carried out at any of normal pressure, under reduced pressure, or under pressure; however, the polymerization step is preferably carried out at normal pressure (or near normal pressure, usually ±10 mmHg). Furthermore, the temperature at the time of initiation of polymerization may vary depending on the kind of the polymerization initiator used; however, the temperature is preferably 15° C. to 130° C., and more preferably 20° C. to 120° C.

(Polymerization Initiator)

The polymerization initiator used in the present invention is appropriately determined according to the polymerization mode and is not particularly limited; however, examples thereof include a photodegradable type polymerization initiator, a thermally degradable type polymerization initiator, a redox polymerization initiator, and the like. Polymerization is initiated by these polymerization initiators.

Examples of the photodegradable type polymerization initiator described above include benzoin derivatives, benzil derivatives, acetophenone derivatives, benzophenone derivatives, azo compounds, and the like. Specific examples include benzoin, benzoin methyl ether, benzoin ethyl ether, benzoin isopropyl ether, α-methylbenzoin, α-phenylbenzoin, anthraquinone, methylanthraquinone, acetophenone, 2,2-diethoxyacetophenone, 2,2-dimethoxy-2-phenylacetone, benzyldiacetylacetophenone, benzophenone, p-chlorobenzophenone, 2-hydroxy-2-methylpropiophenone, diphenyl disulfide, tetramethylthiuram sulfide, α-chloromethylnaphthalene, anthracene, hexachlorobutadiene, pentachlorobutadiene, Michler's ketone, 2-chlorothioxanthone, 2,4-diethylthioxanthone, benzyl dimethyl ketal, bis(2,4,6-trimethylbenzoyl)-phenylphosphine oxide, 2-methyl-1-[4-(methylthio)phenyl]-2-morpholinopropanone-1,2-hydroxy-2-methyl-1-phenylpropan-1-one, 1-[4-(2-hydroxyethoxy)-phenyl]-2-hydroxy-2-methyl-1-propan-1-one, and the like. Such a photodegradable type polymerization initiator may be a commercially available product, and examples thereof include trade name: IRGACURE (registered trademark) 184 (hydroxycyclohexyl phenyl ketone), IRGACURE (registered trademark) 2959 (1-[4-(2-hydroxyethoxy)-phenyl]-2-hydroxy-2-methyl-1-propan-1-one) and the like, manufactured by Ciba Specialty Chemicals Corp.

Furthermore, examples of the thermally degradable type polymerization initiator described above include persulfuric acid salts such as sodium persulfate, potassium persulfate, and ammonium persulfate; peroxides such as hydrogen peroxide, t-butyl peroxide, and methyl ethyl ketone peroxide; azo compounds such as 2,2'-azobis(2-amidinopropane) dihydrochloride and 2,2'-azobis[2-(2-imidazolin-2-yl)propane]dihydrochloride; and the like.

Furthermore, examples of the redox polymerization initiator described above include systems using the persulfuric acid salts or peroxides in combination with reducing compounds such as L-ascorbic acid or sodium hydrogen sulfite.

It is also a preferred embodiment that the photodegradable type polymerization initiator and the thermally degradable type polymerization initiator are used in combination. Furthermore, active energy radiation such as ultraviolet radiation, electron beam or γ-radiation may also be used alone, or in combination with the polymerization initiators described above.

The amount of use of the polymerization initiator described above is preferably 0.0001% to 1% by mole, and more preferably 0.0005% to 0.5% by mole, relative to the amount of the monomers. When this amount of use is in the range described above, deterioration in the color hue of the water absorbent resin powder is reduced, and there remains a less amount of residual monomers.

(Additives and the Like)

On the occasion of the polymerization described above, a chain transfer agent such as hypophosphorous acid (salt), a chelating agent such as diethylenetriaminepentaacetic acid (salt), and the like may also be added to the reaction system before polymerization or in the middle of polymerization as necessary.

(More Suitable Polymerization Method)

According to the present invention, from the viewpoints of the physical properties (for example, water-absorbing speed and liquid permeability) of the water absorbent resin powder, the ease of control of polymerization, and the like, at least one of reverse phase suspension polymerization, spray polymerization, droplet polymerization and aqueous solution polymerization, particularly aqueous solution polymerization is employed as the method for polymerizing an aqueous solution of an acrylic acid (salt)-based monomer.

Examples of a preferred embodiment of the aqueous solution polymerization described above include high temperature-initiated aqueous solution polymerization employing a polymerization initiation temperature of preferably 40° C. or higher, more preferably 50° C. or higher, still more preferably 60° C. or higher, particularly preferably 70° C. or higher, and most preferably 80° C. or higher (the upper limit is the boiling point); or high concentration aqueous solution polymerization employing a monomer concentration of preferably 40% by mass or more, more preferably 45% by mass or more, and still more preferably 50% by mass or more (the upper limit is 90% by mass or less, preferably 80% by mass or less, and still more preferably 70% by mass or less); and high concentration/high temperature-initiated aqueous solution polymerization combining the aforementioned polymerization modes.

The polymerization mode is preferably kneader polymerization or belt polymerization, and preferred modes of the aqueous solution polymerization include continuous belt polymerization (disclosed in U.S. Pat. Nos. 4,893,999 and 6,241,928, US Patent Application Publication No. 2005/215734, WO2008/114847 and the like), continuous kneader polymerization, batch kneader polymerization (disclosed in U.S. Pat. Nos. 6,987,151, 6,710,141, WO 2008/114848 and the like), and the like.

Further examples include high temperature-initiated continuous aqueous solution polymerization, high concentration continuous aqueous solution polymerization, and high concentration/high temperature-initiated continuous aqueous solution polymerization, which combine the preferred embodiments and preferred polymerization modes described above.

Also, another preferred example is batch or continuous kneader polymerization carried out under the conditions of a polymerization initiation temperature of 15° C. or higher and a monomer concentration of 30% by mass or more.

Furthermore, on the occasion of the polymerization described above, the polymerization initiation time (time period from the time point of adding the polymerization initiator to the initiation of polymerization) is preferably more than 0 but not more than 300 seconds, and more preferably 1 to 240 seconds.

(2-3) Gel-Crushing Step

The present step is an optional step for obtaining a particulated hydrogel (hereinafter, referred to as "particulated hydrogel") by gel-crushing a water-containing gel-like crosslinked polymer (hereinafter, referred to as "hydrogel") that is obtained through the polymerization step and the like (particularly, aqueous solution polymerization) described above.

As the hydrogel is subjected to gel-crushing in the aqueous solution polymerization, and particularly as the hydrogel is finely granulated by gel-crushing by kneading, a balance between the water-absorbing speed and liquid permeability is promoted, and impact resistance is also enhanced. That is, aqueous solution polymerization of performing gel-crushing particularly during polymerization (for example, kneader polymerization) or after polymerization (for example, belt polymerization, and if necessary, kneader polymerization) is preferred.

The gel-crusher that can be used in the present invention is not particularly limited; however, examples thereof include a gel-crusher equipped with plural rotating stirring blades, such as a batch type or continuous type double arm kneader; a single-screw extruder, a twin-screw extruder, a meat chopper and the like. Among them, a screw type extruder having a perforated plate at the tip is preferred, and for example, the screw type extruder disclosed in JP-A No. 2000-063527 may be used.

In the gel-crushing step of the present invention, the temperature of the hydrogel (gel temperature) before gel-crushing is preferably 60° C. to 120° C., and more preferably 65° C. to 110° C., from the viewpoints of particle size control and physical properties. When the gel temperature described above is in the range described above, adequate hardness (softness) of the hydrogel is obtained, and the control of the particle shape and the particle size distribution at the time of gel-crushing is made easier. Meanwhile, the gel temperature can be controlled by the temperature at the time of polymerization or by heating, cooling or the like after polymerization.

Furthermore, the mass average particle size (D50) (defined by sieve classification) of the particulated hydrogel after gel-crushing is preferably 0.5 to 10 mm, more preferably 1.0 to 10 mm, and still more preferably 2.0 to 8.0 mm. Furthermore, the proportion of coarse particles having a particle size of 10 mm or more that are included in the particulated hydrogel supplied to the drying step as the subsequent step, is preferably 10% by mass or less, more preferably 5% by mass or less, and still more preferably 1% by mass or less, relative to the total amount of the particulated hydrogel.

According to the present invention, the polymerization step and the gel-crushing step can also be carried out by any of a kneader polymerization method in which a water-containing gel-like crosslinked polymer is gel-crushed during polymerization; a method of supplying a water-containing gel-like crosslinked polymer obtained by continuous belt polymerization to the gel-crushing step, and a method of performing the polymerization step and the gel-crushing step in a batch mode.

(2-4) Drying Step

The present step is a step for obtaining a dry polymer by drying the hydrogel obtainable through the polymerization step and the like. Meanwhile, when the polymerization step is aqueous solution polymerization, gel-crushing (fine granulation) is carried out before drying and/or after drying of the hydrogel. Also, the dried polymer obtainable in the drying step (aggregates) may be supplied directly to the pulverizing step.

The drying method according to the present invention is not particularly limited, and various methods can be employed. Specifically, examples include heat drying, hot air drying, drying under reduced pressure, infrared drying, microwave drying, azeotropic dehydration drying with a hydrophobic organic solvent, high humidity drying using a high temperature steam, and the like, and one kind or two kinds thereof can be used in combination. The drying temperature is preferably 100° C. to 300° C., and more preferably 150° C. to 250° C.

Furthermore, since the drying time is dependent on the surface area or moisture content of the hydrogel, the kind of the drying machine, and the like, for example, the drying time is preferably 1 minute to 5 hours, and more preferably 5 minutes to 1 hour. Furthermore, the resin solid content that is determined from the drying loss (1 g of powders or particles is dried for 3 hours at 180° C.) is preferably 80% by mass or more, more preferably 85% to 99% by mass, and still more preferably 90% to 98% by mass.

(2-5) Pulverizing/Classification Step

The present step is a step for obtaining a water absorbent resin powder preferably having a particular particle size, by pulverizing and/or classifying the dried polymer obtained in the drying step. Meanwhile, this step is different from the gel-crushing step described above (2-3) in terms of the fact that the object of pulverization is subjected to a drying step. Also, the water absorbent resin obtained after the pulverization step may also be referred to as a pulverization product.

(Particle Size Distribution)

The mass average particle size (D50) of the water absorbent resin powder supplied to the surface cross-linking step as the subsequent step, is preferably in the range of 200 to 600 μm, more preferably in the range of 200 to 550 μm, still more preferably in the range of 250 to 500 μm, and particularly preferably in the range of 300 to 450 μm, from the viewpoints of the water-absorbing speed, liquid permeability, absorption capacity under load, and the like.

Furthermore, it is more desirable to have a less amount of fine particles having a particle size of less than 150 μm as defined by standard sieve classification, and from the viewpoints of liquid permeability and the like, the content of the fine particles is preferably 0% to 5% by mass, more preferably 0% to 3% by mass, and still more preferably 0% to 1% by mass. Furthermore, it is more desirable to have a less amount of coarse particles having a particle size of 850 μm or more, and preferably 710 μm or more, as defined by standard sieve classification, and from the viewpoints of the water-absorbing speed and the like, the content of the coarse particles is preferably 0% to 5% by mass, more preferably 0% to 3% by mass, and still more preferably 0% to 1% by mass.

In regard to the distribution range of particle size, in view of the water-absorbing speed, liquid permeability, absorption capacity under load and the like, it is preferable that 95% by mass or more of the particles are included, more preferably 98% by mass or more of the particles are included, and still more preferably 99% by mass or more of the particles are included (the upper limit is 100% by mass), in the range of preferably 150 μm or more but less than 850 μm, and more preferably 150 μm or more but less than 710 μm.

Control of the particle size described above can be achieved by the polymerization step, the gel-crushing step, or the pulverizing/classification step after of the drying step; however, it is particularly preferable to carry out the control by the classification step after drying. Furthermore, measurement of the particle size described above is carried out according to the method stipulated in WO 2004/69915 or EDANA-ERT420.2-02, using the JIS standard sieves (Z8801-1 (2000)).

Furthermore, the shape of the water absorbent resin powder of the present invention may be a spherical shape or an aggregate thereof, or may be an irregular shape (crushed form) obtained by subjecting a hydrogel or a dried polymer to the pulverizing step. However, from the viewpoint of the water-absorbing speed, an irregular shape (crushed form) or a granulated material thereof is preferred.

In order to further solve the problems of the present invention, the aforementioned particle size described above is preferably also applied to the product obtained after the surface cross-linking step, and still more preferably to the final product water absorbing agent. That is, in view of the water-absorbing speed, liquid permeability, absorption capacity under load and the like, the water absorbing agent of the present invention is preferably such that 95% by mass or more is included, more preferably 98% by mass or more is included, and still more preferably 99% by mass or more is included (the upper limit is 100% by mass), preferably in the range of 150 μm or more but less than 850 μm, and more preferably 150 μm or more but less than 710 μm.

(2-6) Fine Powder Recycling Step

It is preferable that a classification step (including a second classification step that follows the surface cross-linking step; hereinafter, the same) is included after the drying step, and during the above-described classification step, water absorbent resin fine particles are separated as a product that has passed through a standard sieve having a mesh size of 150 μm, and then these water absorbent resin fine particles or a product obtained by adding water thereto is recycled (reutilized) to a step before the drying step. Meanwhile, coarse particles that are removed by the classification step described above may be re-pulverized if necessary, and the fine particles that are removed by the classification step described above may be disposed of, may be used in other applications, or may be supplied to the present fine powder recycling step.

By removing the fine particles, the water-absorbing speed (for example, FSR) can be further increased.

That is, according to the production method of the present invention, the fine powder recycling step refers to a step for separating water absorbent resin fine particles (particularly, particles including 70% by mass or more of particles having a particle size of 150 μm or less; hereinafter, also referred to as "fine powder") that are generated in the drying step and optionally the pulverizing, classification step, and then are recycled, either directly or after hydrating or granulating the fine powder, to a step before the drying step, and preferably to the polymerization step, gel-crushing step or drying step.

When the fine powder is recycled, the particle sizes of the water absorbent resin and the water absorbing agent can be controlled, and also, the water-absorbing speed can be further increased by this step.

The fine powder to be recycled may be a fine powder before the surface cross-linking step, or may be a fine powder obtainable after the surface cross-linking step, and the amount of recycling of the fine powder is preferably 1% to 40% by mass, and more preferably 5% to 30% by mass, of the dried polymer.

A fine powder recycling method suitable for the present invention is a method of mixing water absorbent resin fine powder or a hydration product or granulation product thereof, and if necessary, inorganic fine particles and the like into the monomer aqueous solution before polymerization or into the hydrogel during polymerization. Meanwhile, examples of the method for recycling into a monomer aqueous solution before polymerization are described in WO 92/001008 and WO 92/020723; examples of the method for recycling into a hydrogel during polymerization are described in WO 2007/074167, WO 2009/109563, WO 2009/153196, and WO 2010/006937; and examples of the method for recycling into the drying step (dryer) are described in U.S. Pat. No. 6,228,930 and the like. However, these fine powder recycling methods are preferably applied.

(2-7) Surface Cross-Linking Agent Adding Step

The present step is a step for preparing a water absorbent resin powder containing a surface cross-linking agent that is supplied to the surface cross-linking step. In general, surface cross-linking is carried out through addition of an organic surface cross-linking agent that will be described below, through polymerization of monomers at the surface of the water absorbent resin powder, or through addition of a radical polymerization initiator such as a persulfuric acid salt, heating/ultraviolet irradiation, and the like. According to the present invention, it is preferable to add an organic surface cross-linking agent to the water absorbent resin powder obtainable by the classification step, and to the water absorbent resin powder including the water absorbent resin powder obtained through the fine powder recycling step. Also, a liquid permeability enhancing agent adding step that will be described below may also be carried out simultaneously.

(Organic Surface Cross-Linking Agent)

The organic surface cross-linking agent that can be used in the present invention is preferably an organic compound having a reactive group such as a hydroxyl group and/or an amino group, which undergoes a dehydration esterification reaction or a dehydration amidation reaction with a carboxyl group, which is a functional group of the polyacrylic acid (salt)-based water absorbent resin powder, from the viewpoint of the physical properties of the resulting water absorbent resin powder. The organic compound is not limited to an alcohol compound or an amine compound, which directly carries a hydroxyl group or an amino group, and may be a cyclic compound such as an alkylene carbonate compound or an oxazolidinone compound, and a compound having a reactive group that produces a hydroxyl group or an amino group, and/or a reactive group that directly reacts with the carboxyl group is also included therein.

Examples of the organic surface cross-linking agent include a polyhydric alcohol compound, an epoxy compound, a polyvalent amine compound or a condensate thereof with a haloepoxy compound, an oxazoline compound, a (mono-, di- or poly-)oxazolidinone compound, an oxetane compound, an alkylene carbonate compound, and the like; and an epoxy compound, a polyhydric alcohol compound, an alkylene carbonate compound, and an oxazolidinone compound are more preferred. These may be used singly, or two or more kinds thereof may be used in combination.

Specific examples of the organic surface cross-linking agent include polyalcohol compounds such as (di-, tri-, tetra- or poly-)ethylene glycol, (di- or poly-)propylene glycol, 1,3-propanediol, 2,2,4-trimethyl-1,3-pentanediol, (poly) glycerin, 2-butene-1,4-diol, 1,4-butanediol, 1,3-butanediol, 1,5-pentanediol, 1,6-hexanediol, trimethylolpropane, di- or triethanolamine, pentaerythritol, and sorbitol; epoxy compounds such as (poly)ethylene glycol diglycidyl ether, (di- or poly-)glycerol polyglycidyl ether, and glycidol; oxazoline compounds such as 2-oxazolidone, N-hydroxyethyl-2-oxazolidone, and 1,2-ethylenebisoxazoline; alkylene carbonate compounds such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, and 1,3-dioxopan-2-one; haloepoxy compounds such as epichlorohydrin, epibromohydrin, and α-methylepichlorohydrin, and polyvalent amine adducts thereof (for example, KYMENE manufactured by Hercules, Inc.; registered trademark); silane coupling agents such as γ-glycidoxypropyltrimethoxysilane and γ-aminopropyltriethoxysilane; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol, 3-chloromethyl-3-methyloxetane, 3-chloromethyl-3-ethyloxetane, and polyvalent oxetane compounds; cyclic urea compounds such as 2-imidazolidinone; and the like.

The polyhydric alcohol is preferably a polyhydric alcohol having 2 to 8 carbon atoms, more preferably a polyhydric alcohol having 3 to 6 carbon atoms, and still more preferably a polyhydric alcohol having 3 to 4 carbon atoms. Furthermore, a diol is preferred, and examples thereof include ethylene glycol, propylene glycol, 1,3-propanediol, and 1,4-butanediol. A polyhydric alcohol selected from propylene glycol (1,2-propanediol), 1,3-propanediol and 1,4-butanediol is preferred.

Furthermore, as the epoxy compound, a polyglycidyl compound, and preferably ethylene glycol diglycidyl ether, is suitably used. 2-Oxazolidinone is suitably used as the oxazoline compound, and 1,3-dioxolan-2-one (ethylene carbonate) is suitably used as the alkylene carbonate compound.

Furthermore, it is preferable to use two or more kinds of compounds selected from a polyhydric alcohol compound, an epoxy compound, an oxazoline compound, and an alkylene carbonate compound in combination. From the viewpoint of obtaining superior physical properties, a combination of a polyhydric alcohol and the aforementioned organic surface cross-linking agent other than a polyhydric alcohol is preferred, and a combination of a polyhydric alcohol and an epoxy compound or an alkylene carbonate compound is more preferred. From the viewpoint of an increase in CRC, it is still more preferable to use a combination of at least a polyhydric alcohol and an alkylene carbonate compound.

In the case of combining the plural organic surface cross-linking agents described above, particularly in regard to a combination of a polyhydric alcohol and the organic surface cross-linking agent other than a polyhydric alcohol, the ratio (mass ratio) thereof is preferably such that polyhydric alcohol:other than polyhydric alcohol is 1:100 to 100:1, more preferably 1:50 to 50:1, and still more preferably 1:30 to 30:1.

The temperature of the solvent in which these compounds are mixed is appropriately determined; however, if the temperature is too low, solubility or viscosity may be excessively lowered. Therefore, particularly in a case in which a solid non-polymeric organic compound is used as a surface cross-linking agent, and particularly ethylene carbonate is used as a surface cross-linking agent, water that has been warmed to a temperature higher or equal to room temperature (preferably 30° C. to 100° C., more preferably 35° C. to 70° C., and still more preferably 40° C. to 65° C.) is used as the solvent.

That is, it is preferable that the other compound to be mixed with a non-polymeric organic compound (particularly a solid surface cross-linking agent, and a solid polyhydric alcohol or a cyclic compound such as an alkylene carbonate), particularly water, is warmed, and it is more preferable that the temperature is in the temperature range described above.

Furthermore, it is preferable that the alkylene carbonate compound or the polyhydric alcohol compound, and particularly a solid alkylene carbonate compound, is heated in advance before mixing with water. Regarding the heating temperature, it is preferable to heat the compound at a temperature higher than the temperature of the aqueous solution of a surface cross-linking agent after addition of water, and specifically, in the case of a solid alkylene carbonate compound, it is preferable to heat and melt the polyhydric alcohol, particularly the solid polyhydric alcohol, as well. The temperature is preferably 30° C. to 100° C., more preferably 35° C. to 70° C., and still more preferably 40° C. to 65° C.

(Solvent and Concentration)

The amount of addition of the organic surface cross-linking agent is such that the total amount is preferably 0.001 to 15 parts by mass, and more preferably 0.01 to 5 parts by mass, relative to 100 parts by mass of the water absorbent resin before addition.

Furthermore, in a case in which two kinds selected from a polyhydric alcohol compound and a compound other than a polyhydric alcohol are used as the organic surface cross-linking agent, the total amount of the polyhydric alcohol compound is preferably 0.001 to 10 parts by mass, and still more preferably 0.01 to 5 parts by mass, and the total amount of the compound other than a polyhydric alcohol is preferably 0.001 to 10 parts by mass, and still more preferably 0.01 to 5 parts by mass, relative to 100 parts by mass of the water absorbent resin before addition.

The organic surface cross-linking agent is preferably added as an aqueous solution. The amount of water used in the aqueous solution is preferably 0.5 to 20 parts by mass, and more preferably 0.5 to 10 parts by mass, as the total amount relative to 100 parts by mass of the water absorbent resin before the addition treatment. Meanwhile, the water of crystallization, water of hydration of the surface cross-linking agent or the like is also included in this amount of water.

Furthermore, a hydrophilic organic solvent may also be added to the aqueous solution of the organic surface cross-linking agent, and the amount of the hydrophilic organic solvent is preferably more than 0 parts by mass but not more than 10 parts by mass, and more preferably more than 0 parts by mass but not more than 5 parts by mass, relative to 100 parts by mass of the water absorbent resin before the addition treatment. Examples of the hydrophilic organic solvent include primary alcohols having 1 to 4 carbon atoms, and preferably 2 to 3 carbon atoms, as well as lower ketones having 4 or fewer carbon atoms, such as acetone. Particularly, volatile alcohols having a boiling point of lower than 150° C., and more preferably lower than 100° C. is more preferred because the volatile alcohols are volatilized at the time of the surface cross-linking treatment without leaving any residue.

Specific examples include lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane, tetrahydrofuran, and methoxy(poly)ethylene glycol; amides such as ∈-caprolactam and N,N-dimethylformamide; sulfoxides such as dimethyl sulfoxide; polyhydric alcohols such as polyoxypropylene and an oxyethylene-oxypropylene block copolymer; and the like.

Furthermore, on the occasion of mixing of the surface cross-linking agent solution into the water absorbent resin powder, water-insoluble fine particles or a surfactant may also be allowed to co-exist in an amount of more than 0 parts by mass but not more than 10 parts by mass, preferably more than 0 parts by mass but not more than 5 parts by mass, and more preferably more than 0 parts by mass but not more than 1 part by mass, relative to 100 parts by mass of the water absorbent resin before the addition treatment, to the extent that the effects of the present invention are not impaired. In this case, the surfactant and the like used therein are disclosed in U.S. Pat. No. 7,473,739 and the like. Examples of the water-insoluble fine particles include silicon dioxide (silica), zeolite, talc, titanium dioxide, and the like.

The surface cross-linking agent concentration in the surface cross-linking agent solution is appropriately determined; however, in view of the physical properties, an aqueous solution having a concentration of 1% to 80% by mass, 5% to 60% by mass, 10% to 40% by mass, or 15% to 30% by mass, is used. Meanwhile, the balance includes the hydrophilic organic solvent and other components.

The temperature of the surface cross-linking agent solution used is appropriately determined from the solubility of the organic surface cross-linking agent, viscosity of the aqueous solution, and the like; however, the temperature is preferably −10° C. to 100° C., more preferably 5° C. to 70° C., still more preferably 10° C. to 65° C., and particularly preferably in the range of 25° C. to 50° C. When the temperature is in the above-mentioned range, it is preferable because harmful effects, such as hydrolysis of a cyclic compound (for example, decomposition from ethylene carbonate to ethylene glycol, or decomposition from oxazolidinone to ethanolamine) before the surface cross-linking agent is mixed with or reacts with the water absorbent resin powder and volatilization of water or the hydrophilic organic solvent, which leads to a decrease in miscibility, are reduced, and there is a less risk that the surface cross-linking agent solution may be coagulated, or the surface cross-linking agent may be precipitated.

(Combined Use of Acid or Base in Surface Cross-Linking Agent Solution)

The surface cross-linking agent solution may further include an acid or a base, in addition to the organic surface cross-linking agent, water, a hydrophilic organic solvent, a surfactant, and water-insoluble fine particles, in order to promote the reaction or uniform mixing of the surface cross-linking agent.

Regarding the acid or base, an organic acid or a salt thereof, an inorganic acid or a salt thereof, or an inorganic base is used, and the acid or base is appropriately used in an amount of 0 to 10 parts by mass, more preferably 0.001 to 5 parts by mass, and still more preferably 0.01 to 3 parts by mass, relative to 100 parts by mass of the water absorbent resin before the addition treatment. The organic acid is a water-soluble organic acid having 1 to 6 carbon atoms, and more preferably 2 to 4 carbon atoms, and is a water-soluble saturated organic acid, and particularly a hydroxyl group-containing saturated organic acid.

Other examples include non-crosslinkable water-soluble inorganic bases (preferably alkali metal salts, ammonium salts, alkali metal hydroxides, and ammonia or hydroxide thereof), non-reducing alkali metal salt pH buffering agents (preferably hydrogen carbonates, dihydrogen phosphates, hydrogen phosphate, and the like), and the like.

(Method for Adding Organic Surface Cross-Linking Agent Solution)

The organic surface cross-linking agent is added to the water absorbent resin powder by an addition treatment. The method for the addition treatment is not particularly limited, and for example, a method of immersing the water absorbent resin in a hydrophilic organic solvent, and adsorbing the additive cross-linking agent thereto; a method of mixing by spraying or dropping an additive cross-linking agent solution directly to the water absorbent resin; and the like may be used. From the viewpoint of uniformly adding a predetermined amount, the latter method is preferred. Furthermore, in order to uniformly add the cross-linking agent, it is preferable to perform the addition treatment while the water absorbent resin is stirred, and it is preferable to spray a surface cross-linking agent solution.

In regard to the addition treatment, two or more kinds of cross-linking agents having different compositions may be simultaneously added using, for example, different spray nozzles; however, a single composition is preferred from the viewpoints of uniformity and the like. Furthermore, if a single composition is to be used, plural spray nozzles may be used in consideration of the size and throughput of the addition treatment apparatus, the spray angle of the spray nozzles, and the like.

Suitable examples of the apparatus used in the addition treatment (hereinafter, may be referred to as a mixing apparatus) include a cylindrical mixing machine, a double-walled conical mixing machine, a V-shaped mixing machine, a ribbon type mixing machine, a screw type mixing machine, a flow type furnace, a rotary disc mixing machine, a gas stream type mixing machine, a double-armed kneader, an internal mixing machine, a pulverizing kneader, a rotational mixing machine, a screw type extruder, a Turbulizer, a Proshare Mixer, and the like. Furthermore, for large-scale production such as industrial production, an apparatus capable of continuous mixing is preferred. Also, the respective addition treatments may be carried out using the same apparatus, or may be carried out using different apparatuses.

The water absorbent resin powder supplied to the present step is preferably heated and kept warm, and the temperature is preferably in the range of 30° C. to 100° C., more preferably in the range of 35° C. to 80° C., and still more preferably in the range of 40° C. to 70° C. When the water absorbent resin powder is heated and kept warm at the suitable temperature, the chance of the surface treatment becoming insufficient or non-uniform due to precipitation of the surface cross-linking agent, moisture absorption of the water absorbent resin, and the like, is reduced. Also, there is less risk that precipitation and the like of the surface cross-linking agent may occur as a result of evaporation of water from the aqueous solution of surface cross-linking agent or the like.

(2-8) Surface Cross-Linking Step

The present step is a step of performing a heating treatment in order to treat the surface or the vicinity of the surface of the water absorbent resin powder by cross-linking, in order to increase the absorption capacity under load and liquid permeability of the water absorbent resin powder. The present step can be carried out simultaneously with the surface cross-linking agent adding step, or can be carried out after the surface cross-linking agent adding step, and it is preferable to carry out the present step after the surface cross-linking agent adding step. Furthermore, the present step may be carried out once, or may be carried out several times under the same conditions or under different conditions.

In the case of emphasizing the resistance to damage as a physical property of the resulting water absorbing agent, the heating temperature is more preferably 250° C. or lower, still more preferably 70° C. to 200° C., and particularly preferably 90° C. to 180° C. On the other hand, in the case of emphasizing the water absorbent performance, the heating temperature is more preferably 120° C. to 280° C., still more preferably 150° C. to 250° C., and particularly preferably 170° C. to 230° C. Furthermore, the heating time is preferably 1 minute to 2 hours.

(Heating Apparatus)

Regarding the heating apparatus used in the present invention, a continuous type or batch type heating apparatus equipped with a known drying machine or a gas discharging mechanism and/or gas supplying mechanism intended for adopting a predetermined atmosphere to the heating furnace, and preferably a continuous type heating apparatus is suitable.

Regarding the heating mode for the heating apparatus, conductive heat transfer type, radiant heat transfer type, hot air heat transfer type, or dielectric heating type is suitable. More preferably, the heating mode is a conductive heat transfer and/or hot air heat transfer mode, and still more preferably the conductive heat transfer mode.

The so-called control temperature of the heating apparatus may be any temperature at which the water absorbent resin can be heated to an appropriate temperature, and it is not necessary for the control temperature to be constant from the beginning to the end of the process. However, in order to prevent partial overheating and the like, the control temperature is preferably 50° C. to 300° C.

Next, in order to increase the efficiency of heating and carry out an uniform heating treatment, an apparatus having a mechanism for continuously stirring and/or fluidizing the object to be heated is preferred. The stirring and/or fluidizing system is preferably a system of groove type stirring, screw type, rotary type, disc type, kneading type, fluidizing vessel type, or the like, and a stirring system based on the stirring blades (paddles) or a stirring system based on the movement of the heat transfer surface itself such as a rotary retort furnace is more preferred. Meanwhile, since the stirring and/or fluidizing mechanism is intended to perform a uniform heating treatment, the stirring and/or fluidizing mechanism may not be used in a case in which the throughput is small, for example, in a case in which the thickness of the object to be dried is less than 1 cm.

The heating apparatus includes a gas discharging mechanism for discharging the vapor generated from the object to be heated, and the dew point and temperature of the atmosphere in the heating unit (interior of the heating apparatus) can be controlled by regulating the mechanism, for example, through the discharge amount. Meanwhile, the heating unit does not mean a so-called heat source such as a heater or a dielectric coil, but is a place for increasing the temperature of the object to be heated.

Regarding the discharge mechanism, besides those simple exhaust ports, in a case in which a gas is discharged through an outlet of a heat-treated object, the outlet also corresponds to the discharge mechanism. Furthermore, it is preferable to adjust the amount of discharged gas or pressure using a blower or the like. The site of exhausting is not limited to a single site, and plural sites can be provided in consideration of the size of the heating apparatus and the state of regulation of the dew point and temperature.

The heating apparatus includes a gas supply mechanism, and the dew point and temperature of the atmosphere of the heating unit can be controlled by regulating the mechanism, for example, through the amount of supply.

The gas pressure at the heating unit is preferably a pressure slightly decreased from normal pressure. The range of the pressure is such that the pressure difference relative to the atmospheric pressure is preferably 0 to −10 kPa, more preferably 0 to −5 kPa, and still more preferably 0 to −2 kPa.

When industrial continuous production is implemented, a heating apparatus of a batch treatment system or continuous treatment system equipped with the mechanism described above can be used.

In the case of a batch treatment (batch) system, a method of substantially equally distributing the object to be heated in one tray or in plural trays and letting the object to be heated to stand; a method of filling a single vessel or plural vessels with the object to be heated, and heating the object to be heated while stirring with a stirring blade or the like; a fluidizing vessel; or the like is used. Furthermore, in the case of a continuous treatment system, a system of substantially equally distributing the object to be heated on a belt or in plural trays, and transporting the object to be heated; a system of transporting the object to be heated while stirring with a stirring blade, a screw or the like; a system of transporting the object to be heated by means of an inclination of the heating surface; or the like is used.

Meanwhile, in the case of performing the addition treatment both before and after the heating treatment, the addition treatment may be carried out using the same apparatus as that used for the addition treatment, or using different apparatuses. Particularly in the case of using a continuous type production apparatus, it may be preferable in view of production efficiency that the same apparatus is used for the addition treatment before heating and the heating treatment, and another apparatus is used for the addition treatment after heating.

Furthermore, the water absorbent resin taken out from the heating apparatus as necessary may be cooled preferably to a temperature below 100° C., or to 0° C. to 95° C., or 40° C. to 90° C., for the purpose of suppressing excessive progress of the cross-linking reaction or enhancing handleability in the subsequent steps.

(Liquid Permeability Enhancing Agent Adding Step)

The present step is a step of adding a liquid permeability enhancing agent to the water absorbent resin particles obtained after the drying step, or to the water absorbent resin particles obtained after the surface cross-linking step. The liquid permeability enhancing agent as used in the present invention refers to a substance which enhances the saline flow conductivity (SFC) of the water absorbent resin particles after the liquid permeability enhancing agent adding step, as compared with the SFC of the water absorbent resin particles before the liquid permeability enhancing agent adding step.

(Liquid Permeability Enhancing Agent)

An example of the liquid permeability enhancing agent used in the present step is a water-soluble polyvalent metal cation-containing compound. This polyvalent metal cation is a divalent or higher-valent metal cation, and a divalent to tetravalent metal cation is preferred, while a trivalent cation is more preferred.

The term water-soluble is directed to a compound which dissolves in 100 g of water (25° C.) in an amount of 1 g or more, and preferably 10 g or more. A polyvalent metal compound containing the polyvalent metal cation may be mixed directly (mainly in a solid state) with the water absorbent resin particles; however, it is preferable to mix the polyvalent metal compound prepared in the form of an aqueous solution, with the water absorbent resin.

The polyvalent metal cation element that can be used in the present invention is at least one or more metals selected from typical metals and transition metals of Group 4 to Group 11. One selected from Mg, Ca, Ti, Zr, V, Cr, Mn, Fe, Co, Ni, Pd, Cu, Zn, Cd and Al is preferred, Mg Ca, Zn or Al is more preferred, and Al is particularly preferred.

Regarding the polyvalent metal compound containing the polyvalent metal cation, the counter anion may be any of organic or inorganic anions, and there are no particular limitations. Examples thereof include water-soluble aluminum salts such as aluminum acetate, aluminum lactate, aluminum acrylate, aluminum chloride, polyaluminum chloride, aluminum sulfate, aluminum nitrate, bis(potassium aluminum sulfate), and bis(sodium aluminum sulfate); water-soluble alkaline earth metal salts such as calcium chloride, calcium nitrate, magnesium chloride, magnesium sulfate, and magnesium nitrate; transition metal salts such as zinc chloride, zinc sulfate, zinc nitrate, copper sulfate, cobalt chloride, zirconium chloride, zirconium sulfate, and zirconium nitrate; and the like. Among these, particularly preferred is an aluminum compound, and among others, aluminum sulfate is preferred. A powder of hydrated crystals such as aluminum sulfate 14-18 hydrates can be most suitably used.

In the case of using a polyvalent metal salt of an organic acid, preferred anions are bases corresponding to acids such as aliphatic acids such as anisic acid, benzoic acid, p-hydroxybenzoic acid, formic acid, valeric acid, citric acid, glycolic acid, glyceric acid, glutaric acid, chloroacetic acid, chloropropionic acid, cinnamic acid, succinic acid, acetic acid, tartaric acid, lactic acid, pyruvic acid, fumaric acid, propionic acid, 3-hydroxypropionic acid, malonic acid, maleic acid, butyric acid, isobutyric acid, imidinoacetic acid, malic acid, isethionic acid, methylmaleic acid, adipic acid, itaconic acid, crotonic acid, oxalic acid, salicylic acid, gluconic acid, gallic acid, sorbic acid, and stearic acid. Among these, tartaric acid salts and lactic acid salts are preferred, and lactic acid salts such as aluminum lactate and calcium lactate are most preferred.

The method for mixing the polyvalent metal cation involves mixing of an aqueous solution containing the polyvalent metal cation, particularly an aqueous solution having a polyvalent metal cation concentration of 1% to 60% by mass, and preferably 10% to 50% by mass, with the water absorbent resin, and it is more desirable to heat the mixture at about 40° C. to 150° C., and preferably 60° C. to 100° C., as necessary after mixing. The amount of use of water is preferably 0.1 to 5 parts by mass, and more preferably 0.5 to 3 parts by mass, relative to 100 parts by mass of the water absorbent resin.

More preferably, a polyhydric alcohol or an α-hydroxycarboxylic acid is used in combination at the time of mixing.

The polyhydric alcohol or α-hydroxycarboxylic acid is appropriately selected from the various compounds described above. It is preferable that the polyhydric alcohol or α-hydroxycarboxylic acid is used in a smaller amount than water, and in an amount of 0 to 4 parts by mass, 0.01 to 3 parts by mass, or 0.1 to 0.5 parts by mass, relative to 100 parts by mass of the water absorbent resin.

The amount of use of the polyvalent metal compound is, in terms of the polyvalent metal cation (for example, in the case of an aluminum salt, $Al^{3+}$ irrespective of the kind of the salt), preferably in the range of 0.001 to 1 part by mass, more preferably in the range of 0.005 to 0.5 parts by mass, still more preferably in the range of 0.01 to 0.2 parts by mass, and particularly preferably in the range of 0.02 to 0.1 parts by mass, relative to 100 parts by mass of the water absorbent resin particles.

When the polyvalent metal cation content in the particulate water absorbing agent relative to 100 parts by mass of the water absorbent resin is less than 0.001 parts by mass, the increase of SFC is not sufficient, and when the content is more than 1 part by mass, the AAP may be significantly decreased.

(2-9) Multi-Component Metal Compound Adding Step

The method for producing a water absorbing agent of the present invention includes a step for adding a multi-component metal compound.

The multi-component metal compound adding step is a step of adding a multi-component metal compound to the water absorbent resin powder. The multi-component metal compound adding step is preferably carried out after the drying step, and more preferably carried out after the pulverizing/classification step. Furthermore, it is preferable that the multi-component metal compound adding step is carried out as a preceding step and/or subsequent step of the surface cross-linking step (the surface cross-linking step is carried out as a preceding step and/or subsequent step of the multi-component metal compound adding step), and particularly preferably carried out after the surface cross-linking step (a multi-component metal compound is added to the surface cross-linked water absorbent resin powder). Furthermore, the relevant step may be carried out several times, and in that case, the step is carried out at least once after the drying step. More preferably, the step is carried out after the pulverizing/classification step, and preferably carried out as a preceding step and/or subsequent step of the surface cross-linking step, and particularly preferably carried out after the surface cross-linking step.

(Dust Reducer)

A dust reducer is a multi-component metal compound used for the purpose of reducing the amount of dust generated from a water absorbing agent. Specifically, it is desirable if the amount of dust determined according to the method described in the Examples described below is reduced in the water absorbing agent obtainable after the addition of the multi-component metal compound, compared with the water absorbing agent in the case in which the multi-component metal compound has not been added. Specifically, it is preferable that the amount of dust of the water absorbing agent after the addition is reduced by 10% or more, more preferably reduced by 20% or more, and still more preferably reduced by 30% or more, compared with the water absorbing agent in the case in which the multi-component metal compound has not been added. The multi-component metal compound of the present invention is a multi-component metal compound containing a hydroxyl group and two kinds of metal cations that are divalent and trivalent, and has the functions of reducing the decrease in the water absorption performance such as AAP of the water absorbing agent and suppressing blocking against moisture absorption.

Examples of the divalent metal cation include $Mg^{2+}$, $Fe^{2+}$, $Zn^{2+}$, $Ca^{2+}$, $Ni^{2+}$, $Co^{2+}$, and $Cu^{2+}$, and from the viewpoints of heat resistance and the like, $Mg^{2+}$ is preferred. Examples of the trivalent metal cation include $Al^{3+}$, $Fe^{3+}$, and $Mn^{3+}$, and from the viewpoints of heat resistance and the like, $Al^{3+}$ is preferred. Therefore, according to a suitable embodiment of the multi-component metal compound as a dust reducer, the divalent metal cation is magnesium cation, and the trivalent metal cation is aluminum cation.

It is preferable that the multi-component metal compound has a hydrotalcite-like structure that is known as a structure of a layered compound represented by general formula (1) $5[M_1{}^{2+}{}_{1-x}M_2{}^{3+}{}_x(OH^-)_2]^{x+}.[(A^{n-})_{x/n}.mH_2O]^{x-}$ (wherein $M_1{}^{2+}$ represents a divalent metal cation; $M_2{}^{3+}$ represents a trivalent metal cation; $A^{n-}$ represents an n-valent anion; and $H_2O$ represents water).

Furthermore, the ratio of the divalent metal cation and the trivalent metal cation in the general formula (1) is such that x is preferably in the range of 0.2 to 0.75, more preferably in the range of 0.25 to 0.7, and still more preferably in the range of 0.25 to 0.5. Furthermore, examples of the anion include $OH^-$, $F^-$, $Cl^-$, $Br^-$, $NO_3{}^-$, $CO_3{}^{2-}$, $SO_4{}^{2-}$, $Fe(CN)_6{}^{3-}$, $CH_3COO^-$, oxalate ion, salicylate ion, and the like; however, carbonate anion is preferred. Also, m represents a real number larger than 0, and it is preferable that $0<m\leq10$.

The shape of the multi-component metal compound is not particularly limited; however, the shape is preferably spherical (including a powder form). Also, it is preferable that the multi-component metal compound has a constant particle size, and the volume average particle size is preferably 2 μm or less, more preferably 1.5 μm or less, and still more preferably 1 μm or less. When the particle size is increased, it is necessary to use a large amount of addition in order to obtain a sufficient dust reducing effect, and as a result, the water absorption performance of the resulting water absorbing agent may be impaired. If the particle size is too small, there is a risk that workability may be deteriorated at the time of the adding step, or sufficient performance may not be obtained. Therefore, the volume average particle size is preferably 0.05 μm or more, more preferably 0.1 μm or more, and still more preferably 0.3 μm or more. Meanwhile, the volume average particle size of the dust reducer can be measured by the "laser diffraction scattering method" (measured using, for example, trade name: Microtrac MT3000II particle size analyzer manufactured by Nikkiso Co., Ltd.). Furthermore, measurement of the average particle size of the multi-component metal compound adhering to the water absorbent resin surface can be carried out by a measurement method using SEM (scanning electron microscopy), which is a method described in the Examples.

Furthermore, the multi-component metal compound may have an organic compound intercalated between the layers, and may also be subjected to a surface treatment for increasing miscibility with a resin and the like.

Preferred examples of the structural formula of the multi-component metal compound include $Mg_6Al_2(OH)_{16}CO_3.4H_2O$, $Mg_4Al_2(OH)_{12}CO_3.3H_2O$ and the like, and specific examples include DHT-4H and DHT-6 manufactured by Kyowa Chemical Industry Co., Ltd.; STABIACE HT-1-NC and STABIACE HT-P manufactured by Sakai Chemical Industry Co., Ltd; and the like.

It does not matter whether HT compounds are surface-treated or not; however, HT compounds that are not surface-treated are more preferred. Specific examples of the surface treating agent used in the surface treatment include the following (a) to (j):

(a) higher fatty acids such as stearic acid, oleic acid, erucic acid, palmitic acid, and lauric acid;

(b) metal salts such as lithium salts, sodium salts and potassium salts of the acids of (a);

(c) anionic surfactants including sulfuric acid ester salts of higher alcohols such as stearyl alcohol and oleyl alcohol; sulfuric acid ester salts of polyethylene glycol ether, amide-bonded sulfuric acid ester salts, ether-bonded sulfonic acid salts, ester-bonded sulfonates, amide-bonded alkylarylsulfonic acid salts, ether-bonded alkylarylsulfonic acid salts, and the like;

(d) mono- or diesters of ortho-phosphoric acid and oleyl alcohol, stearyl alcohol and the like, or mixtures thereof, which are acid forms or phosphoric acid esters of alkali metal salts, amine salts, or the like of those compounds;

(e) silane coupling agents such as vinylethoxysilane, γ-methacryloxypropyltrimethoxysilane, vinyltris(2-methoxyethoxy)silane, and γ-aminopropyltrimethoxysilane;

(f) titanium coupling agents such as isopropyltriisostearoyl titanate, isopropyltris(dioctyl pyrophosphate) titanate, and isopropyltridecylbenzenesulfonyl titanate;

(g) alkali coupling agents such as acetoalkoxyaluminum diisopropylate;

(h) ethanolamines such as monoethanolamine, diethanolamine, and triethanolamine;

(i) n-propanolamines such as n-propanolamine, di-n-propanolamine, and tri-n-propanolamine; and (j) isopropanolamines such as monoisopropanolamine, diisopropanolamine, and triisopropanolamine.

Among them, ethanolamines such as monoethanolamine, diethanolamine and triethanolamine are preferred.

(Amount of Addition)

The amount of addition of the multi-component metal compound is preferably 0.01% to 5% by mass, more preferably 0.01% to 4.5% by mass, still more preferably 0.1% to 4.5% by mass, further still more preferably 0.1% to 4% by mass, and particularly preferably 0.15% to 3.5% by mass, relative to the amount of the polyacrylic acid (salt)-based water absorbent resin powder. If the amount of addition is less than 0.01% by mass, a sufficient dust reducing effect is not obtained, and if the multi-component metal compound is added in an amount of more than 5% by mass, a reducing effect corresponding to the amount of addition is not obtained.

Therefore, the content of the multi-component metal compound in the final absorbing agent of the present invention is defined as described above; however, since the amount of addition of the multi-component metal compound is a small amount relative to the amount of the water absorbing agent, the content in the absorbing agent is also substantially 0.01% by mass to 5% by mass.

In order to sufficiently suppress blocking against moisture absorption only by the addition of the multi-component metal compound, the amount of addition is preferably 0.1% by mass or more, and more preferably 0.2% by mass or more. Furthermore, from the viewpoint of the water absorption performance, the amount of addition is preferably 1% by mass or less, more preferably 0.8% by mass or less, still more preferably 0.6% by mass or less, and particularly preferably 0.4% by mass or less.

(Adding/Mixing Method)

It is preferable to dry mix the multi-component metal compound of the present invention with a water absorbent resin powder. It is preferable because the amount of dust of the resulting water absorbing agent is reduced by dry mixing. The term dry mixing means mixing in a state in which any liquid substance other than the liquid substance absorbed or retained by the multi-component metal compound and the water absorbent resin powder supplied to the present step does not exist. Specifically, the present invention includes an embodiment in which a multi-component metal compound containing hygroscopic moisture or an organic compound retained between layers, is mixed with a water absorbent resin powder including a dry residue, hygroscopic moisture, the surface cross-linking agent added in the surface cross-linking agent adding step, a solvent and the like, without further adding a liquid substance.

In order to sufficiently obtain the effects of the multi-component metal compound, it is preferable to mix thoroughly after the addition, and the specific mixing conditions may be appropriately determined in accordance with the apparatus used, throughput and the like. For example, a method of stirring and mixing for about 30 seconds to 1 minute at a speed of rotation of 300 rpm using a Lödige mixer; and a method of stirring and mixing for 20 minutes to 1 hour at speed of rotation of 60 rpm using a paddle type stirring apparatus may be mentioned. Furthermore, a method of mixing while imparting vibration, or a method of adding a water absorbent resin powder while stirring may also be used.

(2-10) Other Additive Adding Step

The present step is a step of adding additives for the multi-component metal compound in order to impart various functions to the (surface-cross-linked) water absorbent resin, and is composed of one process or plural processes. Examples of the additives include inorganic/organic fine particles, a cationic polymer compound, a water-soluble polyvalent metal cation-containing compound, a surfactant, a coloration preventing agent, a urine resistance enhancing agent, a deodorizer, a fragrance, an antimicrobial agent, a foaming agent, a pigment, a dye, a fertilizer, an oxidizing agent, a reducing agent, and the like. Furthermore, the additives may also be additives having their functions imparted or improved.

Unless particularly stated otherwise, the amount of the additives is less than 10% by mass, preferably less than 5% by mass, and more preferably less than 1% by mass, relative to 100% by mass of the surface cross-linked water absorbent resin powder. Furthermore, these additives may be added simultaneously with the surface cross-linking agent adding step, or may be added in a separate step.

(Inorganic/Organic Fine Particles)

Examples of the inorganic fine particles include inorganic fine particles other than the multi-component metal compound, such as water-insoluble fine particulate inorganic powders such as silicon dioxide, titanium dioxide, aluminum oxide, magnesium oxide, zinc oxide, talc, metal phosphates (for example, calcium phosphate, barium phosphate, and aluminum phosphate), metal borates (for example, titanium borate, aluminum borate, iron borate, magnesium borate, manganese borate, and calcium borate), silicic acid or salts thereof, clay, diatomaceous earth, zeolite, bentonite, kaolin, and active white clay. Examples of the organic fine particles include organic fine powders such as calcium lactate, aluminum lactate, metal soaps (polyvalent metal salts of long-chain fatty acids). The volume average particle size (defined with a laser diffraction scattering particle size analyzer) of the inorganic/organic fine particles is preferably 10 μm or less, and more preferably 1 μm or less. The lower limit of the volume average particle size of the inorganic/ organic fine particles is not particularly limited; however, the lower limit is preferably 5 nm or more.

These may be incorporated in the form of a powder into the water absorbent resin, may be incorporated in the form of an aqueous dispersion (slurry, for example, colloidal silica), or may be incorporated in the form of being dispersed in the surface cross-linking agent or an aqueous solution thereof.

The multi-component metal compound of the present invention has an effect of suppressing the amount of dust by adding the inorganic fine particles described above to a water absorbent resin powder, and when using inorganic fine particles, it is preferable to use the multi-component metal compound in combination.

The amount of addition of the inorganic/organic fine particles used is preferably 0.01 to 3 parts by mass, and more preferably 0.1 to 1.0 parts by mass, relative to 100 parts by mass of the water absorbent resin added.

(Cationic Polymer Compound)

The cationic polymer compound is not particularly limited; however, the cationic polymer compounds listed as examples in U.S. Pat. Nos. 5,382,610 and 7,098,284, WO 2009/110645, WO 2009/041731, and WO 2009/041727 can be suitably used. Among them, polyethyleneimine, polyvinylamine, polyallylamine, and a condensate of dimethylamine/ammonia/epichlorohydrin are preferred.

The molecular weight of the cationic polymer compound is, as mass average molecular weight, preferably 1000 to 5,000,000, more preferably 2000 to 1,000,000, and still more preferably 10,000 to 500,000.

The cationic polymer compound is preferably water-soluble. Here, the term water-soluble implies that 1 g or more of the cationic polymer compound dissolves in 100 g of water at 25° C.

These may be directly mixed with the water absorbent resin, may be incorporated in the form of a solution, particularly an aqueous solution, or may be incorporated after being dissolved in a surface cross-linking agent or an aqueous solution thereof.

(Water-Soluble Polyvalent Metal Cation-Containing Compound)

The water-soluble polyvalent metal cation-containing compound refers to a compound other than the multi-component metal compound containing divalent or higher-valent, and preferably trivalent or higher-valent, metal cations. Examples of the trivalent or higher-valent metal cations include aluminum, zirconium, and titanium, and aluminum is preferred. Examples of the polyvalent metal cation-containing compound include polyvalent metal compounds etc., including inorganic salts of polyvalent metals such as aluminum sulfate, aluminum chloride, zirconium chloride oxide, ammonium zirconium carbonate, potassium zirconium carbonate, potassium zirconium carbonate, zirconium sulfate, zirconium acetate, and zirconium nitrate; organic salts of polyvalent metals such as aluminum acetate, aluminum lactate, zirconium hydroxychloride, titanium triethanolaminate, and titanium lactate; and the like. Among them, a compound containing aluminum as the polyvalent metal cation is preferred.

These may be directly incorporated in the form of a powder to the water absorbent resin, may be incorporated in the form of a solution, particularly an aqueous solution, or may be incorporated after being dissolved in a surface cross-linking agent or an aqueous solution thereof.

The amount of addition of the water-soluble polyvalent metal cation-containing compound is, in terms of the amount of the polyvalent metal cation, preferably 0.001 to 5 parts by mass, more preferably 0.01 to 2 parts by mass, and still more preferably 0.01 to 1 part by mass, relative to 100 parts by mass of the water absorbent resin added.

Also, the water-soluble polyvalent metal cation-containing compound may be added several times, and in that case, for example, when the compound is added twice, the (mass) ratio thereof is defined to be in the range of 1/99 to 99/1, and preferably 10/90 to 90/10. When the ratio is beyond these ranges, the circumstance is highly similar to that of addition in a single time, and it is not preferable because the effect of addition in several times is insufficient.

In the case of adding the water-soluble polyvalent metal cation-containing compound as an aqueous solution, a hydrophilic organic solvent (an alcohol or a polyglycol) or surfactant may be used in combination with water so as to enhance dispersibility, solubility, or miscibility. The amount of water used is appropriately determined based on the kind of the additive or the addition method; however, the amount is, for example, 0 part by mass (dry mixing) to 50 parts by mass, 0.1 to 10 parts by mass, or 0.5 to 5 parts by mass, relative to 100 parts by mass of the water absorbent resin.

(Surfactant)

Furthermore, the polyacrylic acid (salt)-based water absorbent resin powder may include a surfactant, and it is preferable that the production method of the present invention includes a step of incorporating a surfactant in any step.

When the surface of the water absorbent resin powder of the present invention is coated with a surfactant, a water absorbent resin powder having a high water-absorbing speed and high liquid permeability is obtained. Meanwhile, there are no particular limitations on the surfactant, but examples thereof include the surfactants, that is, nonionic surfactants, anionic surfactants, cationic surfactants, amphoteric surfactants, and the like disclosed in WO 97/017397 and U.S. Pat. No. 6,107,358. These surfactants may be surfactants that are polymerizable or reactive with acrylic acid (salt)-based monomers or water absorbent resin powder. Regarding the specific compound, the compounds described in Patent Documents 45 and 46 (2-1) are applied.

The kind or amount of use of the surfactant used is appropriately determined; however, preferably the surfactant is used in the range of surface tension described above, and is used in an amount in the range of 0 to 0.5 parts by mass, 0.00001 to 0.1 parts by mass, or 0.001 to 0.05 parts by mass, relative to 100 parts by mass of the water absorbent resin. Among these surfactants, from the viewpoint of effect, anionic surfactants, nonionic surfactants, or silicone-based surfactants are preferably used, and nonionic surfactants or silicone-based surfactants are more preferably used.

(Coloration Preventing Agent and Urine Resistance Enhancing Agent)

According to the present invention, it is preferable to further include a coloration preventing agent or a urine resistance enhancing agent selected from chelating agents (particularly, organic phosphorus-based chelating agents and aminocarboxylic acid-based chelating agents), α-hydroxycarboxylic acids (particularly, malic acid (salts)), and inorganic or organic reducing agents (particularly, sulfur-based inorganic reducing agents) for the purpose of preventing coloration or deterioration (or reduction of residual monomers, and the like). Meanwhile, a water absorbent resin powder having a large surface area generally tends to be susceptible to coloration or deterioration. Among others, from the viewpoints of an effect of prevention of coloration with the lapse of time and an enhancement of urine resistance, it is preferable that the water absorbing agent includes a chelating agent, and from the viewpoint of the coloration preventing effect, it is preferable that the water absorbing agent includes compounds selected from the group consisting of a chelating agent, an α-hydroxycarboxylic acid (salt), an inorganic or organic reducing agent (particularly, a sulfur-based inorganic reducing agent), and a phosphorus compound. Therefore, a suitable exemplary embodiment of the present invention further includes a chelating agent adding step in which a chelating agent is added.

Examples of the chelating agent described above include the chelating agents disclosed in U.S. Pat. Nos. 6,599,989 and 6,469,080, European Patent No. 2163302, and the like, particularly non-polymeric chelating agents, and more specifically organic phosphorus-based chelating agents, aminocarboxylic acid-based chelating agents, inorganic polyvalent phosphoric acids, and amino-polyvalent phosphoric acids.

Examples of the organic phosphorus-based chelating agents include nitriloacetic acid-di(methylenephosphinic acid), nitrilodiacetic acid-(methylenephosphinic acid), nitriloacetic acid-β-propionic acid-methylenephosphonic acid, nitrilotris(methylenephosphonic acid), 1-hydroxyethylidenediphosphonic acid, and the like. Examples of the aminocarboxylic acid-based chelating agents include iminodiacetic acid, hydroxyethyliminodiacetic acid, nitrilotriacetic acid, nitrilotripropionic acid, ethylenediaminetetraacetic acid, diethylenetriamine pentaacetic acid, triethylenetetraminehexaacetic acid, trans-1,2-diaminocyclohexanetetraacetic acid, N,N-bis(2-hyroxyethyl)glycine, diaminopropanoltetraacetic acid, ethylenediaminedipropionic acid, hydroxyethylenediaminetriacetic acid, glycol ether diaminetetraacetic acid, diaminopropanetetraacetic acid, N,N'-bis(2-hydroxybenzyl)ethylenediamine-N,N'-diacetic acid, 1,6-hexamethylenediamine-N,N,N',N'-tetraacetic acid, salts thereof, and the like.

Examples of the inorganic polyvalent phosphoric acid include metaphosphoric acid, pyrophosphoric acid, tripolyphosphoric acid, hexametaphosphoric acid, salts thereof, and the like.

Examples of the amino-polyvalent phosphoric acid include ethylenediamine-N,N'-di(methylenephosphinic acid), ethylenediaminetetra(methylenephosphinic acid), cyclohexanediaminetetra(methylenephosphonic acid), ethylenediamine-N,N'-diacetic acid-N,N'-di(methylenephosphonic acid), ethylenediamine-N,N'-di(methylenephosphonic acid), ethylenediaminetetra(methylenephosphonic acid), polymethylenediaminetetra(methylenephosphonic acid), diethylenetriaminepenta(methylenephosphonic acid), salts thereof, and the like.

Preferred examples of the salts include monovalent salts, particularly alkali metal salts such as sodium salts and potassium salts; ammonium salts, and amine salts, while sodium salts and potassium salts are particularly preferred.

Among the chelating agents described above, aminocarboxylic acid-based chelating agents, amino-polyvalent phosphoric acids and salts thereof are suitably used from the viewpoint of preventing coloration. Among them, diethylenetriaminepentaacetic acid, triethylenetetraminehexaacetic acid, trans-1,2-diaminocyclohexanetetraacetic acid, ethylenediaminetetra(methylenephosphonic acid), diethylenetriaminepenta(methylenephosphonic acid), and salts thereof are more suitably used. Among these, ethylenediaminetetra (methylenephosphonic acid) or salts thereof are most preferred.

Examples of the α-hydroxycarboxylic acids include malic acid (salts), succinic acid (salts), and lactic acid (salts) disclosed in US Patent Application Publication No. 2009/0312183 and the like.

Examples of the inorganic or organic reducing agents described above include the sulfur-based reducing agents, particularly sulfites, hydrogen sulfites, and the like, disclosed in US Patent Application Publication No. 2010/0062252 and the like.

The inorganic reducing agent according to the present invention is distinguished from the reducing agent as a polymerization initiator used in the polymerization step. That is, an inorganic reducing agent refers to a compound having reducing properties, and may have a reducing inorganic element. Specific examples thereof include compounds having reducing sulfur atoms or reducing phosphorus atoms, and preferred examples include a compound containing a reducing sulfur atom and a water-soluble compound containing a reducing phosphorus atom. Therefore, regardless of being an inorganic compound or organic compound, any compound having a reducing sulfur atom or a reducing phosphorus atom is regarded as the inorganic reducing agent of the present invention.

The inorganic reducing agent may be in an acid form, but is preferably in a salt form, and regarding salts, monovalent or polyvalent metal salts are more preferred, and monovalent salts are still more preferred. Among these inorganic reducing agents, oxygen-containing reducing inorganic compounds listed below as examples, that is, inorganic reducing agents in which sulfur or phosphorus is bonded to oxygen, and among them, oxygen-containing reducing inorganic salts, are preferred. Also, these inorganic reducing agents may also be inorganic reducing agents formed from organic compounds having an alkyl group, a hydroxyalkyl group and the like, which carry reducing inorganic atoms, and preferably reducing sulfur atoms or phosphorus atoms.

Furthermore, in regard to an inorganic reducing agent carrying a reducing sulfur atom or a reducing phosphorus atom that is used in the present invention, the oxidation number of a most stable sulfur atom is +6 (positive hexavalent), and the oxidation number of a phosphorus atom is +5 (positive pentavalent). However, in general, various atoms having oxidation numbers less than or equal to those values have reducing properties, so that sulfur compounds having a value of +4 (for example, sulfite, hydrogen sulfite, and pyrosulfite), sulfur compounds having a value of +3 (for example, dithionite), sulfur compounds having a value of +2 (for example, sulfoxylate), phosphorus compounds having a value of +4 (for example, hypophosphate), phosphorus compounds having a value of +3 (for example, phosphate and pyrophosphate), and phosphorus compounds having a value of +1 (for example, hypophosphite) are used. In these reducing inorganic compounds, the reducing sulfur atoms or reducing phosphorus atoms may be substituted with organic materials.

There are no particular limitations on the inorganic compounds containing sulfur atoms as inorganic reducing agents; however, examples thereof include sulfites such as sodium sulfite, potassium sulfite, calcium sulfite, zinc sulfite, and ammonium sulfite; hydrogen sulfites such as sodium hydrogen sulfite, potassium hydrogen sulfite, calcium hydrogen sulfite, and ammonium hydrogen sulfite; pyrosulfites such as sodium pyrosulfite, potassium pyrosulfite, and ammonium pyrosulfite; dithionites such as sodium dithionite, potassium dithionite, ammonium dithionite, calcium dithionite, and zinc dithionite; trithionates such as potassium trithionate and sodium trithionate; tetrathionates such as potassium tetrathionate and sodium tetrathionate; thiosulfates such as sodium thiosulfate, potassium thiosulfate, and ammonium thiosulfate; nitrites such as sodium nitrite, potassium nitrite, calcium nitrite, and zinc nitrite; and the like. Examples of inorganic compounds containing phosphorus atoms include sodium hypophosphite and the like. Furthermore, examples of organic compounds containing sulfur atoms as inorganic reducing agents include 2-hydroxy-2-sulfinatoacetate, sodium formaldehydesulfoxylate, formamidinesulfinic acid and thioglycolic acid tris(2-carboxyethyl)phosphine hydrochloride (TCEP), and tributylphosphine (TBP) and the like. Among these, sulfites, hydrogen sulfites, pyrosulfites and dithionites are preferred, and preferred examples include sodium sulfite, sodium hydrogen sulfite, potassium pyrosulfite, sodium dithionite, 2-hydroxy-2-sulfinatoacetic acid, 2-hydroxy-2-sulfonatoacetic acid, and/or salts thereof. Preferred salts include alkali metal and alkaline earth metal salts, and preferred examples include Li, Na and K, while sodium salts are particularly preferred. 2-Hydroxy-2-sulfinatoacetic acid (salt) may be used in combination with 2-hydroxy-2-sulfonatoacetic acid (salt).

2-Hydroxy-2-sulfinatoacetic acid as a preferred inorganic reducing agent is an inorganic reducing agent of the present invention because it has a reducing sulfur atom as a sulfinato group, and is available as BRUGGOLITE (registered trademark) FF7, which is commercially available from Brueggemann Chemical KG (Heilbron, Germany), or is available as BRUGGOLITE (registered trademark) FF6 containing 50% to 60% by weight of 2-hydroxy-2-sulfinatoacetic acid disodium salt, 30% to 35% by weight of sodium sulfite ($Na_2SO_3$), and 10% to 15% by weight of 2-hydroxy-2-sulfonatoacetic acid disodium salt.

There are organic phosphorus compounds and inorganic phosphorus compounds as phosphorus compounds are, and preferred examples thereof include water-soluble phosphorus compounds. When the phosphorus compound is water-insoluble, it is not preferable because the affinity with a hydrogel-like polymer or a water absorbent resin is decreased, and the effects of prevention of coloration of a particulate water absorbing agent and coloration prevention with the lapse of time are deteriorated. Furthermore, from the viewpoints of the physical properties, for example, the absorption capacity under load of the resulting water absorbing agent, and suppression of a decrease in surface tension, inorganic phosphorus compounds are preferred.

A particularly preferred phosphorus compound is a water-soluble inorganic phosphorus compound, and specific examples thereof include phosphoric acid, phosphorous acid, hypophosphorous acid, triphosphoric acid, tripolyphosphoric acid, and salts thereof (for example, disodium monohydrogen phosphate, monosodium dihydrogen phosphate, trisodium phosphate, and the like), and a particularly preferred compound is phosphoric acid (salt) that does not have reducing properties from the viewpoint of the absorption characteristics of the water absorbing agent. Furthermore, preferred examples of the salt include water-soluble monovalent salts, that is, alkali metal salts such as sodium salts and potassium salts, ammonium salts, and amine salts. Among the salts thereof, from the viewpoint of the effect of preventing coloration with the lapse of time, most preferred salts are salts exhibiting acidity of pH 7 or lower, which include phosphoric acid, monosodium dihydrogen phosphate, monopotassium dihydrogen phosphate, and monoammonium dihydrogen phosphate.

The phosphorus compounds described above may be used singly, or may be used in combination of two or more kinds.

The amount of use of the coloration preventing agent or the urine resistance enhancing agent is preferably 0 to 3 parts by mass, more preferably 0.001 to 1 part by mass, and particularly preferably 0.05 to 0.5 parts by mass, relative to 100 parts by mass of the water absorbent resin powder.

The coloration preventing agent or urine resistance (weather resistance) enhancing agent may be added to the monomers, hydrogel, dry polymer, water absorbent resin powder, and the like; however, it is preferable to add the agent after the polymerization step. Particularly, since the inorganic or organic reducing agent is consumed in the polymerization step, it is preferable to add the coloration preventing agent or urine resistance enhancing agent after the polymerization step, and more preferably after the drying step, and it is particularly preferable to add at least a portion thereof after the surface cross-linking step.

According to a suitable exemplary embodiment, the coloration preventing agent or urine resistance (weather resistance) enhancing agent is added in the (2-1) Step for preparing aqueous solution of acrylic acid (salt)-based monomer described above, or is added to the water absorbent resin powder obtained in the surface cross-linking step after the (2-8) Surface cross-linking step and before the (2-9) Multi-component metal compound adding step.

The amounts of use in the various production processes substantially become the contents in the water absorbing agent thus obtained; however, the various compounds in the water absorbing agent can be appropriately quantitatively analyzed in the same manner as in quantitative analyses of residual monomers or water soluble components, by extracting each of the compounds from the water absorbing agent using water or physiological saline, and performing liquid chromatography, ion chromatography or the like.

As described above, it is preferable that the water absorbing agent includes a chelating agent; however, it is preferable that at least a portion of the chelating agent is added in the (2-1) Step for preparing acrylic acid (salt)-based monomer, or the (2-2) Aqueous solution polymerization step, and it is more preferable that the chelating agent is added to the aqueous solution of an acrylic acid (salt)-based monomer at least in the step (2-1). At this time, the amount of addition of the chelating agent is preferably 0.1% to 3.0% by mass relative to the amount of the acrylic acid (salt)-based monomer.

Furthermore, from the viewpoint of preventing coloration with the lapse of time, in addition to the addition of the chelating agent in the (2-1) Step for preparing aqueous solution of acrylic acid (salt)-based monomer or in the (2-2) Aqueous solution polymerization step, it is preferable to further add any one of the chelating agent, inorganic reducing agent, α-hydroxycarboxylic acid and phosphorus compound after the surface cross-linking and before the (2-9) Multi-component metal compound adding. From the viewpoint of enhancing urine resistance, it is preferable to further add any one of the chelating agent and inorganic reducing agent after the surface cross-linking and before the (2-9) Multi-component metal compound adding. At this time, the amount of addition (total amount) of these compounds is preferably 0.001 to 5 parts by mass relative to 100 parts by mass of the water absorbent resin particles after surface cross-linking. The chelating agent, inorganic reducing agent and phosphorus compound may be used singly, or may be used in combination of two or more kinds thereof.

The addition of the chelating agent, inorganic reducing agent, α-hydroxycarboxylic acid and phosphorus compound may be added to the water absorbent resin after the surface cross-linking without solvent, and in a case in which the compounds are solid, powder mixing (dry blending) is acceptable; however, in view of fixing to the water absorbent resin, the compounds are used in the form of a solution, an aqueous solution, or an aqueous liquid. Regarding the solvent, water or a mixed solvent of water and an organic solvent is used in an amount in the range of 0.01 to 10 parts by mass, 0.05 to 30 parts by mass, and 0.1 to 10 parts by mass, relative to 100 parts by mass of the water absorbent resin, and the aqueous solution concentration may be about 1% to 50% by mass. Furthermore, a surfactant and the like may also be used as necessary. The solvent may be dried, if necessary.

In addition to that, the water-soluble polysiloxanes described in WO 2009/093708, the primary to tertiary amine compounds described in WO 2008/108343, and the like can also be preferably used as additives.

[3] PHYSICAL PROPERTIES OF WATER ABSORBING AGENT OR POLYACRYLIC ACID (SALT)-BASED WATER ABSORBENT RESIN POWDER (3-1) AAP (Absorption Capacity Under Load)

It is preferable that the water absorbent resin to be mixed with the multi-component metal compound, and the water absorbing agent obtained by such mixing have predetermined AAP values. By taking the surface cross-linking after polymerization as an example of the achieving means, the absorption capacity (AAP) against a 0.9 mass % aqueous solution of sodium chloride under a pressure of 2.06 kPa exhibits a value of 20 (g/g) or more, preferably 25 (g/g) or more, and more preferably 30 (g/g) or more. Meanwhile, it is preferable if the AAP is higher; however, from the viewpoint of the balance with other physical properties (or example, CRC), the upper limit is preferably 40 (g/g) or less, more preferably 35 (g/g) or less, and still more preferably 33 (g/g) or less. The AAP can be controlled by surface cross-linking and the CRC.

While the addition of inorganic fine particles other than a multi-component metal compound, such as silica that has been conventionally used, causes a significant decrease in the AAP (for example, 3 to 10 g/g), the multi-component metal compound of the present invention is such that if the compound is added in an amount necessary for adjusting the blocking ratio against moisture absorption to 30% by mass or less, the AAP almost does not decrease (usually 1 g/g or less, or 0.5 g/g or less). Therefore, the AAP enhancing effect caused by surface cross-linking can be maintained at a high level, and satisfactory absorption in actual use (for example, high absorption capacity in diapers) is exhibited.

Specifically, the water absorbing agent of the present invention is such that the absorption capacity (AAP) against a 0.9 mass % aqueous solution of sodium chloride under a pressure of 2.06 kPa is preferably 20 (g/g) or more, more preferably 25 (g/g) or more, and still more preferably 30 (g/g) or more. Meanwhile, it is preferable if the AAP is higher; however, the upper limit thereof is usually about 50 (g/g) or less.

(3-2) CRC (Absorption Capacity without Load)

The absorption capacity without load (CRC) of the water absorbent resin to be mixed with the multi-component metal compound and the water absorbing agent obtained by such mixing exhibits a value of 25 (g/g) or more, preferably 30 (g/g) or more, and more preferably 33 (g/g) or more. When the absorption capacity without load is low, the efficiency in the case of using the water absorbing agent in hygienic materials such as diapers is poor. Meanwhile, it is preferable if the CRC is higher; however, from the viewpoint of the balance with other physical properties (for example, AAP), the upper limit is preferably 60 (g/g) or less, more preferably 50 (g/g) or less, and still more preferably 45 (g/g) or less. The CRC can be controlled with the cross-linking density at the time of polymerization or surface cross-linking.

When the multi-component metal compound of the present invention is added in an amount necessary for adjusting the blocking ratio against moisture absorption to 30% by mass or less, similarly to the case of the AAP, a decrease in the CRC (weight fraction added to the most, for example, the decrease in the CRC by about 1% at the time of addition of 1% by weight, usually 1 g/g or less, or 0.5 g/g or less) is also small. Therefore, since a water absorbing agent having a high CRC value is obtained, the water absorbing agent exhibits satisfactory absorption performance (for example, high absorption capability in diapers) in actual use.

In other words, as a result of the addition of the multi-component metal compound of the present invention to a water absorbent resin powder, a balance between high AAP and low blocking ratio against moisture absorption can be achieved in the resulting water absorbing agent, and the amount of dust is also reduced.

(3-3) Solid Content

The solid content of the water absorbing agent is a value calculated by the method described in the Examples, and is preferably 85% to 99% by mass, more preferably 88% to 98% by mass, and still more preferably 90% to 95% by mass. If the solid content is less than 85% by weight, it is not preferable because the absorption capacity without load or the absorption capacity under load is decreased, and if the solid content is higher than 98% by weight, it is not preferable because the decrease in the absorption capacity under load resulting from mechanical damage caused by conveyance or the like is large.

(3-4) Blocking Ratio Against Moisture Absorption

The blocking ratio against moisture absorption is calculated by the method described in the Examples, and it is preferable if the blocking ratio against moisture absorption is lower. The blocking ratio against moisture absorption is preferably 30% by mass or less, more preferably 28% by mass or less, and still more preferably 26% by mass or less. The lower limit value is 0% by mass or more in view of the principle of calculation. The blocking ratio against moisture absorption can be controlled to a low level, even if only the multi-component metal compound of the present invention is used, by adding an appropriate amount of the metal compound particularly after the surface cross-linking step, and dry blending. When the blocking ratio against moisture absorption is controlled to a low level, the water absorbing agent can be used stably even under any work environment or the use conditions at the user's site (for example, the operating conditions for a diaper production process).

(3-5) Amount of Dust

The amount of dust of the water absorbent resin to be mixed with the multi-component metal compound and the water absorbing agent obtained by such mixing is calculated by the method described in the Examples.

The value of the amount of dust varies depending on the method for producing the water absorbent resin powder; the additives other than the multi-component metal compound; or the like; however, the amount of dust in a water absorbing agent is usually preferably 200 mg/kg of the water absorbing agent or less, more preferably 150 mg/kg of the water absorbing agent or less, still more preferably 100 mg/kg of the water absorbing agent or less, and particularly preferably 70 mg/kg of the water absorbing agent or less. The value is ideally 0 mg/kg of the water absorbing agent; however, in consideration of the productivity in actual use and the productivity in an industrial scale, the lower limit value is 10 mg/kg of the water absorbing agent or more, preferably 15 mg/kg of the water absorbing agent or more, and more preferably 20 mg/kg of the water absorbing agent or more.

The amount of dust can be controlled to a low level by controlling the particle size of the water absorbent resin, as well as by use of the multi-component metal compound of the present invention, particularly dry mixing after the surface cross-linking step. When the amount of dust is controlled to a low level, there is no problem of dust even under any work environment or the use conditions at the user's site (for example, operating conditions for a diaper production process).

The multi-component metal compound of the present invention can be used in a water absorbent resin, for example, a film, a sheet or a gel, having a substantially zero amount of dust; however, usually, the multi-component metal compound of the present invention can be used in a water absorbent resin in a powder form, particularly a water absorbent resin having the particle size described below, and in a water absorbent resin powder containing a predetermined amount of dust. The multi-component metal compound can be suitably used in a water absorbent resin powder, for example, a water absorbent resin powder containing dust in an amount of 2 mg/kg of the water absorbent resin powder or more, preferably 5 mg/kg of the water absorbent resin powder or more, more preferably 5 to 1000 mg/kg of the water absorbent resin powder, 10 to 500 mg/kg of the water absorbent resin powder, and more preferably 20 to 400 mg/kg of the water absorbent resin powder, and particularly in an irregularly shaped water absorbent resin powder.

(3-4) Extr.

The Extr. (water soluble components) of the water absorbent resin or water absorbing agent obtainable by the present invention is preferably 5% to 30% by mass, more preferably 5% to 20% by mass, still more preferably 5% to 18% by mass, and particularly preferably 5% to 15% by mass. When the Extr. exceeds 30% by mass, there is a risk that the resulting water absorbent resin or water absorbing agent may have weak gel strength and poor liquid permeability. Also, when the water absorbent resin is used in a water absorbent body such as a diaper, there is a risk that a water absorbent resin having less return of liquid (rewetting) when a pressure is applied on the water absorbent body, may not be obtained, which is not preferable.

Meanwhile, the Extr. can be appropriately controlled with the internal cross-linking agent described above and the like. In order to obtain a water absorbent resin or water absorbing agent having an Extr. value of less than 5% by mass, it is necessary to use a large amount of the internal cross-linking agent, and it is not preferable because the CRC is markedly decreased, in addition to cost increase and generation of residual cross-linking agent (exceeding the detection limit)

(3-5) Particle Size

There are no particular limitations on the particle size or particle size distribution of the water absorbent resin (particularly before the surface cross-linking step and/or before the multi-component metal compound adding step) or the resulting water absorbing agent used in the present invention; however, it is preferable to regulate the particle size after adding and mixing the final surface post-crosslinking agent, and to adjust the particle size to the range described below (defined by sieve classification).

The upper limit of the particle size is particles having a particle size of less than 1 mm, and it is preferable to obtain a water absorbent resin or water absorbing agent having the particle size described below. When particles having a particle size of 1 mm or more, particularly particles having a particle size of 850 μm or more, are included in a large amount, when the coarse particles are used particularly in thin hygienic materials and absorbent articles, there is a risk that the wearer may have unpleasant feelings, the coarse particles may damage the water-impermeable material that constitutes the absorbent articles, a so-called back sheet, by scratching, and the coarse particles may cause leakage of urine and the like in actual use, which is not preferable. Therefore, it is preferable if there is a less amount of particles having a particle size of 850 μm or more, and the amount is preferably 0% to 5% by mass, more preferably 0% to 3% by mass, and still more preferably 0% to 1% by mass, while it is particularly preferable that the coarse particles are substantially not included.

On the other hand, regarding the fine particles side, the proportion of particles having a particle size of less than 150 μm is preferably 0% to 3% by mass, more preferably 0% to 2% by mass, and still more preferably 0% to 1.5% by mass. When there is a large amount of fine particles in the water absorbent resin or water absorbing agent, the fine particles tend to cause an increase in dust, a decrease in hygroscopic fluidity, and decreases in the physical properties such as AAP and liquid permeability.

Furthermore, while the range described is maintained, the particle size distribution of the water absorbent resin or water absorbing agent is such that in the range of 150 μm or more but less than 850 μm, preferably 95% by mass or more of the particles are included, more preferably 98% by mass or more is included, and still more preferably 99% by mass or more is included. It is most preferable that substantially the entire amount is included in the given range.

Furthermore, in the present invention, the water absorbent resin that has been subjected to the above-described steps, and the water absorbing agent obtainable as a final product are such that the mass average particle size defined by standard sieve classification is preferably 600 μm or less, and in order to enhance the performance, the mass average particle size is more preferably in the range of 550 to 200 μm, still more preferably in the range of 500 to 250 μm, and most preferably in the range of 450 to 300 μm. Furthermore, the proportion of particles having a particle size of less than 300 μm is preferably 10% by mass or more, more preferably in the range of 10% to 50% by mass, and still more preferably in the range of 10 to 30% by mass.

The particle size can be appropriately controlled by applying pulverization or classification (before the surface cross-linking step and/or after the surface cross-linking step), or granulation, the fine powder recycling step, and the like. Furthermore, while the multi-component metal compound of the present invention is in the form of fine particles (preferably less than 2 μm and as described above), the multi-component metal compound does not cause an increase in a fine powder (for example, less than 150 μm) of the added water absorbing agent or in dust. The reason for this is not clearly known, but it is speculated that since cationic fine particles bring about an interaction with the carboxyl groups (anionic groups) of the water absorbent resin, and are associated at the surface of the water absorbent resin (preferably, having particles having a size of 150 μm or more but less than 850 μm as a main component), an increase in fine powder or suppression of dust is achieved.

When the particle size is deviated from these ranges, a well-balanced water absorbent resin which maintains a desired absorption capacity and also has excellent liquid permeability, may not be obtained. Particularly, there is a risk that particles having a particle size of less than 150 μm may not only decrease liquid permeability, but also have adverse effects due to dust generation or the like on the environment of production operation for an absorbent article which uses the water absorbent resin as a raw material. Therefore, it is preferable that the amount of fine particles is as smaller as possible.

(3-6) Shape

The shape of the water absorbing agent and the water absorbent resin can be applied particularly to a sheet form, a fibrous form, a powder form, a gel form or the like, and can also be applied to a powder form having the particle size described above and to irregularly shaped particles. Here, the term irregular shape means the particle shape obtained by pulverizing a gel or a dried product. Meanwhile, the particles may be a granulation product, or may also be primary particles.

(3-7) Method for Evaluating Colorability of Water Absorbing Agent Raw Material According to Water-Soluble Magnesium Ion Quantification Method The multi-component metal compound in which the divalent metal cation is magnesium ion may have decreased coloration resistance or urine resistance, and the inventors of the present invention found that the degree of deterioration of coloration resistance and the elution amount of magnesium ions from the multi-component metal compound are correlated to each other. It has been conventionally known that one of the causes for a decrease in coloration resistance is the influence exerted by transition metals such as Fe; however, the influence exerted by magnesium, which is an alkaline earth metal, is not known.

In general, the stability constant of a chelating agent, log $K_{ML}$, is such that Fe ion which is widely known as a cause of coloration in a water absorbing agent has a higher value than Mg ion. For example, in the case of EDTA, $Fe^{2+}$ has a value of 14.3, and $Fe^{3+}$ has a value of 25.1, while $Mg^{2+}$ has a value of 8.7. In the case of DTPA, $Fe^{2+}$ has a value of 16.6, and $Fe^{3+}$ has a value of 28.6, while $Mg^{2+}$ has a value of 9.3. That is, since a chelating agent that is used as a coloration resistance enhancing agent will trap Fe ions far much preferentially to Mg ions, it is not likely that the capturing ability for Fe ions is interrupted by the presence of Mg ions.

The present invention also relates to a method for evaluating colorability of a water absorbing agent caused by water-soluble magnesium ions in the raw materials used in the production of the water absorbing agent. Specifically, when a water absorbing agent includes 0.1 ppm by mass or more, particularly 0.2 ppm by mass or more, of magnesium ions in terms of the amount of addition to the water absorbing agent determined by the (5-12) method for quantitatively analyzing water-soluble magnesium ions as described below, it may be speculated that there is a concern about a decrease in the coloration resistance of the water absorbing agent. Particularly, in hydrotalcite, the amount of water-soluble magnesium ions may vary with the composition or production method, and the amount of magnesium can be utilized as a means for selecting more suitable hydrotalcite.

Meanwhile, the present evaluation method can be applied not only to multi-component metal compounds, but also to other additives containing magnesium, for example, magnesium oxide, magnesium carbonate, or hard water. In that case, evaluation can be carried out using other additives containing magnesium, instead of hydrotalcite, in the evaluation method of (5-12) described below.

(3-8) Water Absorbing Agent Containing Magnesium Ion and Chelating Agent

The present invention also relates to a water absorbing agent containing a chelating agent and a raw material which has a converted amount of water-soluble magnesium ions of 0.1 ppm by mass or more, in the method for evaluating colorability described above. When the converted amount is less than 0.1 ppm, a decrease in coloration resistance to the extent that requires addition of a chelating agent is not observed. When the converted amount is 20 ppm by mass or more, since a large amount of a chelating agent is needed, there may be a problem from the viewpoint of cost. Meanwhile, it is preferable that the converted amount is smaller, and the converted amount is preferably 15 ppm by mass or less, more preferably 10 ppm by mass or less, still more preferably 5 ppm by mass or less, and particularly preferably 1 ppm by mass or less.

Furthermore, the raw material is preferably hydrotalcite containing magnesium and aluminum.

Furthermore, regarding the chelating agent, the chelating agents described in the (2-10) Coloration preventing agent can be used. Furthermore, it is more preferable when the α-hydroxycarboxylic acid (particularly malic acid (salt)) and the inorganic or organic reducing agent (particularly, sulfur-based inorganic reducing agent) described in the (2-10) Coloration preventing agent are used in combination.

[4] APPLICATIONS ETC. OF PARTICULATE WATER ABSORBING AGENT

The water absorbent resin of the present invention is used in hygienic materials such as paper diapers, sanitary napkins, incontinence pads, and medical pads. In that case, it is preferable to use a configuration including (a) a liquid-permeable top sheet that is disposed adjacently to the body of a wearer, (b) a back sheet that is impermeable to liquid and is disposed far from the body of the wearer and adjacently to the clothes of the wearer, and a water absorbent body disposed between the top sheet and the back sheet. The water absorbent body may include two or more layers, and may also be used together with a pulp layer and the like.

[5] EXAMPLES

Hereinafter, the invention is described by way of Examples, but the present invention should not be construed to be limited to the Examples. Furthermore, the various physical properties described in the claims and Examples of the present invention were determined according to the following measurement methods (5-1) to (5-13). Meanwhile, unless particularly stated otherwise, the various processes in the various Examples were carried out at substantially normal pressure (±5% of the atmospheric pressure, more preferably within 1%), and during the same process, the process was carried out without applying any pressure change caused by intentional pressurization or pressure reduction.

(5-1) Particle Size and Mass Average Particle Size (D50)

The particle size of a water absorbent resin powder/water absorbing agent related to the present invention was measured according to the measurement method disclosed in European Patent No. 0349240.

That is, 10 g of a particulate water absorbing agent was classified using the JIS standard sieves (JIS Z8801-1 (2000)) having mesh sizes of 850 μm, 710 μm, 600 μm, 500 μm, 420 μm, 300 μm, 212 μm, 150 μm, 106 μm, and 45 μm, or equivalent sieves. The masses of the water absorbent resin powder remaining on the respective sieves and the water absorbent resin powder/water absorbing agent that had passed through all the sieves were respectively measured.

(5-2) CRC (Water Absorption Capacity without Load)

The water absorption capacity for 30 minutes without load (CRC) against a 0.90 mass % aqueous solution of sodium chloride (also referred to as physiological saline) was determined according to ERT441.2-0.2.

(5-3) Water Absorption Capacity Under Load (AAP)

Measurement of the water absorption capacity under load (AAP) was carried out according to ERT442.2-02.

That is, 0.9 g of a particulate water absorbing agent (mass W3 [g]) was introduced into a measuring apparatus, and the mass of a set of the measuring apparatus (W4 [g]) was measured. Subsequently, a 0.90 mass % aqueous solution of sodium chloride was made to be absorbed by the particulate water absorbing agent under an added pressure of 2.06 kPa. After the passage of one hour, the mass of the set of the measuring apparatus (W5 [g]) was measured. The water absorption capacity under load (AAP) was calculated by the following Formula 1 from the values of W3 [g], W4 [g] and W5 [g] thus obtained.

$$AAP\ [g/g]=(W5-W4)/W3 \quad \text{(Formula 1)}$$

(5-4) Solid Content

This represents the proportion occupied by components that do not volatilize at 180° C. in a water absorbent resin powder. The relationship thereof with the moisture content is as follows: {solid content=100−moisture content}.

The method for measuring the solid content was carried out as follows.

Approximately 1 g of a water absorbent resin powder was weighed (mass W7 [g]) in an aluminum cup (mass W6 [g]) having a bottom diameter of about 5 cm, and the resin powder was left to stand for 3 hours in a still dryer at 180° C. and dried. The total mass of the aluminum cup and the water absorbent resin powder after drying (W8 [g]) was measured, and the solid content was determined by the following Formula 2.

$$\text{Solid content [mass \%]}=\{(W8-W6)/W7\}\times 100 \quad \text{(Formula 2)}$$

(5-6) Blocking Ratio Against Moisture Absorption

Approximately 2 g of a water absorbent resin powder/water absorbing agent was uniformly spread in an aluminum cup having a diameter of 52 mm, and then was left to stand for one hour in a thermo-hygrostat (manufactured by Espec Corp.; Model: SH-641) that was adjusted to a temperature of 25° C. and a relative humidity of 90±5% RH.

Thereafter, the water absorbent resin powder/water absorbing agent in the aluminum cup described above was gently transferred onto a JIS standard sieve (The IIDA Testing Sieve/inner diameter 80 mm) having a mesh size of 2000 μm (8.6 mesh), and the water absorbent resin powder/water absorbing agent was classified using a ro-tap type sieve shaker (manufactured by IIDA Seisakusho Corp.; ES-65 type sieve shaker/speed of rotation 230 rpm, number of impacts 130 rpm), for 5 seconds under the conditions of a temperature of 20° C. to 25° C. and a relative humidity of 50% RH.

Subsequently, the masses of the water absorbent resin powder/water absorbing agent remaining on the JIS standard sieve (mass W9 [g]) and the water absorbent resin powder/water absorbing agent that had passed through the JIS standard sieve (mass W10 [g]) described above were measured, and the hygroscopic fluidity (blocking ratio against moisture absorption) was calculated by the following Formula 3. The blocking ratio against moisture absorption is such that the value is lower, the hygroscopic fluidity is superior.

$$\text{Blocking ratio against moisture absorption [mass \%]}=\{W9/(W9+W10)\}\times 100 \quad \text{(Formula 3)}$$

(5-7) Measurement of Particle Size of Multi-Component Metal Compound (Hydrotalcite) on Water Absorbing Agent In regard to the particle size of the multi-component metal compound (hydrotalcite) related to the present invention, the unidirectional particle diameters of 100 grains of the fine particles adhering to the water absorbent resin surface were measured, and the average particle size was determined. For the measuring apparatus, a 3D real surface view microscope (manufactured by Keyence Corp.) was used.

Specifically, first, a water absorbing agent containing a multi-component metal compound added therein was classified using JIS standard sieves (JIS Z8801-1 (2000)) having mesh sizes of 600 μm and 300 μm, or equivalent sieves, and a water absorbing agent portion having a particle size of from 300 μm to 600 μm was collected. Approximately 0.05 g of the water absorbing agent was spread on a conductive carbon double-sided tape for SEM (manufactured by Nisshin EM Corp.) having a size of 0.8 cm×0.8 cm, and the tape was pasted on the observatory stand of a 3D real surface view microscope. Thereafter, images of the water absorbing agent surfaces were captured using the 3D real surface view microscope (detector; secondary electron detector, accelerating voltage: 1.7 kV, magnification ratio: 5000 times), the unidirectional particle diameters of the multi-component metal compound adhered on the water absorbing agent surface were measured, and the average particle size was determined (meanwhile, in the case of a water absorbing agent composed only of particles that had passed through the sieve having a mesh size of 300 μm, or composed only of particles that did not pass through the sieve having a mesh size of 600 μm, the measurement is made by substituting the water absorbing agent particles with particles classified at a width from the upper limit to the lower limit of 300 μm from the particles of a particle size distribution close to the mesh size of 600 to 300 μm, for example, 600 to 900 μm, and 300μ to 0 μm).

(5-8) Measurement of Amount of Dust

The measurement was carried out according to the description of [281] to [282] of WO 2006/098271. That is, the amount of dust of a water absorbing agent was measured based on the increase in mass of dust suctioned and captured on a glass fiber filter paper for a predetermined time under the conditions described below. For the measuring apparatus, a Heubach DUSTMETER manufactured by Heubach Engineering GmbH, Germany, was used, and the measurement was carried out in Type II measurement mode. The temperature of the atmosphere at the time of measurement was 23° C. (±2° C.), the relative humidity was 20% to 40%, and the pressure was normal pressure. The measurement method was carried out as follows.

(1) 100.00 g of a water absorbing agent as a measurement sample is introduced into a rotating drum.

(2) The mass of a glass fiber filter paper having a diameter of 50 mm (for example, manufactured by Advantec Group, GLASS FIBER GC-90 or an equivalent product thereof is processed to have a diameter of 50 mm) and having a retention particle size of 0.5 μm (JIS P3801) is measured to the place of 0.00001 g ([Da] g).

(3) A large-scale particle separator is installed in the rotating drum, and a filter case equipped with a glass fiber filter paper is installed thereon.

(4) The measurement conditions of the control unit in the dust meter are set as follows, and measurement is made. Number of drum rotation: 30 rpm, amount of suction wind; 4 L/min, time (measurement time): 30 minutes.

(5) After a predetermined time, the mass of the glass fiber filter paper is measured to the place of 0.00001 g ([Db]).

The amount of dust is calculated by the following Formula 4 using the Da value and the Db value.

$$\text{Amount of dust [mg/kg]}=([Db]-[Da])/100\times 1{,}000{,}000 \qquad \text{(Formula 4)}$$

(5-9) Method for Evaluating Coloration with the Lapse of Time

Coloration of a water absorbent resin after performing a coloration acceleration test as described below was evaluated.

The coloration acceleration test was carried out by placing a container for powder/paste sample filled with 5 g±0.01 g of a water absorbent resin in a thermo-hygrostat (small-sized environmental testing machine manufactured by Espec Corp.; Model SH-641) adjusted to an atmosphere at a temperature of 70° C. and a relative humidity of 65 RH % (apparatus setting), and exposing the water absorbent resin for one week.

The color hue of the water absorbent resin after exposure was measured. The measurement was carried out using a spectroscopic colorimeter, SZ-Σ80 COLOR MEASURING SYSTEM, manufactured by Nippon Denshoku Industries Co., Ltd. Regarding the cell for measurement, a round cell having a size of 35 mmφ×15H manufactured by Nippon Denshoku Kogyo Co., Ltd. was used, and the set condition for measurement was reflection measurement, and a standard round white board No. 2 for powder/paste, 30φ translucent pipe was used as a reference. 5 g±0.01 g of the water absorbent resin was filled in the cell.

(5-10) Elution Amount of Deteriorated Soluble Component 200 g of a 0.90 mass % aqueous solution of sodium chloride containing L-ascorbic acid dissolved therein at a concentration of 0.05% by weight (solution A) and 1 g of a water absorbent resin (composition) were introduced into a 250-ml glass beaker, the beaker was covered with a food wrapping film, and the beaker was left to stand for 2 hours at 60° C. Thereafter, a 35-mm rotator was introduced therein, and the content was stirred with a magnetic stirrer (about 500 rpm) for 1 hour and filtered with a pleated filter paper (manufactured by Toyo Roshi Kaisha, Ltd., No. 2). 50 g of the filtrate thus obtained was introduced into a 100-ml beaker, and acid-alkali titration was carried out.

First, the filtrate was titrated to pH 10 with a 0.1 N aqueous NaOH solution, and the titer Va (ml) was determined. Subsequently, the filtrate was titrated to pH 2.7 with a 0.1 N aqueous HCl solution, and the titer Vb (ml) was determined. Meanwhile, the same operation was carried out using a blank without introducing a water absorbent resin (composition), and Vab and Vbb were respectively determined as the blank amounts. The elution amount of deteriorated soluble components of the water absorbing agent (composition) was calculated by the following formula from the numerical values thus obtained.

$$\text{Elution amount of deteriorated soluble component (mass \%)}=0.1\times Mw\times 200\ \text{(amount of solution } A)\times 100\times(Vb-Vbb)/1000/1\ \text{(water absorbing agent)}/50\ \text{(amount of filtrate used for titration)}$$

Mw: Average molecular weight of polymer unit=72 (molecular weight of acrylic acid)×(1−N/100)+94 (molecular weight of sodium acrylate)×N/100

N: Neutralization rate of water absorbent resin=−(((Va−Vab)/(Vb−Vbb))−1)×100

(5-11) L-as/Fe Resistance Testing Method 60 g of a 0.90 mass % aqueous solution of sodium chloride containing 0.02% by weight of L-ascorbic acid and 0.0002% by weight of iron sulfate heptahydrate dissolved therein, and 2 g of a water absorbing agent (composition) were introduced into a 120-ml plastic container with a lid, and the container was covered with the lid and left to stand for 16 hours at 37° C. After 16 hours, the container was taken out from the oven, and an evaluation was carried out by visual inspection according to the following evaluation criteria.

(Evaluation method)

○: The gel does not flow even if the container is tumbled on its side.

Δ: The gel is deformed when the container is tumbled on its side.

X: The gel is deformed when the container is tumbled on its side and reaches the end of the container.

(5-12) Water-Soluble Magnesium Ion Quantification Method 100 g of ion-exchanged water was weighed in a beaker, and was heated to 70° C. At the time point of reaching 70° C., the amount of water was adjusted to 100 g, 1.0 g of hydrotalcite was added thereto, and the mixture was stirred for 10 minutes. The liquid after stirring was filtered twice using a filter paper No. 2 (24 cmφ) of Advantec Corp., and the filtrate was sucked in into a plastic syringe having a capacity of 60 ml, and was filtered by mounting a membrane filter (CHROMATODISC 25A manufactured by GL Sciences, Inc., pore diameter 0.45 μm). A liquid thus obtained was used as a measurement sample.

Quantification of magnesium ion was carried out using an ICP emission spectrometer (manufactured by Thermo Fisher Scientific, Inc., Thermo iCAP6500 Duo) under the following conditions.

Measurement mode: Axial (optical measurement in axial direction)

Detection wavelength: 279.6 nm

RF power: 1150 W

Pump flow rate: 50 rpm

Auxiliary gas: 1 L/min

Nebulizer gas: 0.65 L/min

Turbulent gas: 12 L/min

Additive gas: 0 L/min

Purge gas: 5.2 L/min

Meanwhile, detection was carried out by an external calibration curve method of using a calibration curve produced using general-purpose standard solutions for 23 element quantification (XSTC-22, manufactured by SPEX, Inc.). Furthermore, when the concentration adjustment of the standard solutions and the concentration adjustment of measurement samples were carried out, ultrapure water obtained with a water purifying apparatus (manufactured by Millipore Corp., Milli-Q Labo) was used.

(5-13) Quantification Method for Multi-Component Metal Compound (Hydrotalcite) by X-Ray Diffraction Qualitative and quantitative analyses of the hydrotalcite compound included in a water absorbent resin powder were carried out by powder X-ray diffraction (XRD) using a powder X-ray diffraction apparatus (manufactured by Rigaku Corp., product name: SMARTLAB). The measurement conditions are shown below.

X-radiation source: CuKα radiation (λ=0.15418 nm)/45 kV/200 mA

Scan range: 2θ=5° to 80°

Scan speed: 3°/min

A sample was uniformly filled in a glass sample holder having a depression measuring 0.5 mm, and the surface of the filled sample was flattened using another glass plate from the outside. Subsequently, the glass plate filled with the sample was mounted on the powder X-ray diffraction apparatus, and an XRD pattern was obtained.

Whether a water absorbent resin powder contains a hydrotalcite compound or not can be determined by checking whether or not two strong peaks characteristic to a hydrotalcite compound are recognized in the obtained XRD pattern. Specifically, when diffraction peaks are present at both the positions of the following two diffraction angles (a) and (b), it can be determined that the water absorbent resin powder contains a hydrotalcite compound.

(a) 2θ=11.5°±1.0°

(b) 2θ=22.9°±1.0°

The diffraction peak present at the position of (a) is determined to be based on the diffraction line for the (003) plane of the hydrotalcite compound, and the diffraction peak present at the position of (b) is determined to be based on the diffraction line for the (006) plane of the hydrotalcite compound.

A quantitative analysis of hydrotalcite included in the water absorbent resin powder can be calculated from the diffraction peak intensities of the XRD pattern. Specifically, XRD measurement of a water absorbent resin powder containing a known amount of hydrotalcite was carried out, and a calibration curve was produced from the diffraction peak intensities of (a) 2θ=11.5°±1.0° or (b) 2θ=22.9°±1.0° of the XRD pattern. This calibration curve was used as the external standard, and thus the content (% by mass) of the hydrotalcite compound in the water absorbent resin powder was determined.

Production Example 1

In 5500 g of an aqueous solution of sodium acrylate having the neutralization rate of 75% by mole (monomer concentration: 35% by mass), 0.38 g of trimethylolpropane triacrylate (molecular weight 296) (0.006% by mole relative to the monomer) was dissolved, and a monomer aqueous solution (a) was prepared. Subsequently, the monomer aqueous solution was degassed for 30 minutes in a nitrogen gas atmosphere.

Next, the monomer aqueous solution (a) was introduced into a reactor produced by providing a lid to a double blade type jacketed kneader made of stainless steel with an internal capacity of 10 L and having two sigma-shaped blades. Nitrogen gas was blown into the reactor while the liquid temperature was maintained at 30° C., and the reactor was purged with nitrogen such that the dissolved oxygen in the system reached 1 ppm or less.

Subsequently, 24.6 g of a 10 mass % aqueous solution of sodium persulfate and 21.8 g of a 0.2 mass % aqueous solution of L-ascorbic acid were separately added to the monomer aqueous solution (a) with stirring, and polymerization was initiated after about 1 minute. While the produced water-containing gel-like cross-linked polymer (a) was crushed, polymerization was performed at 30° C. to 90° C., and when 60 minutes had passed from the initiation of polymerization, a water-containing gel-like cross-linked polymer (a) was taken out from the reactor. The water-containing gel-like cross-linked polymer (a) thus obtained was subjected to grain refining to particles having a diameter of about 5 mm.

The water-containing gel-like cross-linked polymer (a) thus subjected to grain refining described above was spread on a wire gauze having a mesh size of 300 μm (50-mesh) and dried under hot air for 45 minutes at 180° C. Subsequently, the cross-linked polymer was pulverized with a roll mill, and was classified with JIS standard sieves having mesh sizes of 850 μm and 150 μm. Through this series of operations, a water absorbent resin powder (a), which was a water absorbent resin (solid content 4.0% by mass) in an irregularly shaped crushed form, was obtained. The CRC (water absorption capacity without load) of the water absorbent resin powder (a) was 53.0 [g/g].

Next, the water absorbent resin powder (a) was transferred into a rotary mixer manufactured by Deutsche Lödige GmbH, and an aqueous solution of surface cross-linking agent including 0.025 parts by mass of ethylene glycol diglycidyl ether (trade name: DENACOL EX-810 manufactured by Nagase ChemteX Corp.), 0.3 parts by mass of ethylene carbonate (melting point 36° C.), 0.5 parts by mass of 1,2-propanediol (melting point−59° C.), and 3.0 parts by mass of water, was uniformly mixed relative to 100 parts by mass of the water absorbent resin powder (a). The mixture was heat treated for 40 minutes at 175° C. Thereafter, the mixture was passed through a JIS standard sieve having a mesh size of 850 μm, and thereby water absorbent resin particles (surface cross-linked water absorbent resin) (a-1) were obtained. The water absorbent resin particles (a-1) were irregularly shaped, and 95% by mass or more of the particles were included in the range of 150 μm or more but less than 850 μm.

Production Example 2

In polypropylene containers having an inner diameter of 80 mm and a capacity of 1 liter and covered with expanded polystyrene, which is a thermal insulating material, a solution (A) in which 291 g of acrylic acid, 0.43 g (0.02% by mole relative to the carboxyl group-containing unsaturated monomer) of polyethylene glycol diacrylate (molecular weight 523) as an internal cross-linking agent, 1.80 g of a 1.0 mass % aqueous solution of pentasodium diethylenetriaminepentaacetate, and 3.60 g of a 1.0 mass % acrylic acid solution of IRGACURE (registered trademark) 184 were mixed, and a solution (B) in which 247 g of a 48.5 mass % aqueous solution of sodium hydroxide and 255 g of ion-exchanged water adjusted to 50° C. were mixed, were prepared. A monomer aqueous solution (C) was obtained by rapidly adding the solution (B) to the solution (A), which was being stirred at 800 rpm using a magnetic stirrer having a length of 5 cm, and mixing the solutions. The liquid temperature of the monomer aqueous solution (C) was increased to about 100° C. due to the heat of neutralization and the heat of dissolution. The neutralization rate of acrylic acid was 73.5% by mole.

Next, 1.8 g of a 3 mass % aqueous solution of sodium persulfate was added to the monomer aqueous solution (C), the mixture was stirred for about 1 second, and then the mixture was poured immediately into a vat type container made of stainless steel and lined with TEFLON (registered trademark) on the inner surface in an open system. Furthermore, ultraviolet was irradiated simultaneously with pouring of the monomer aqueous solution into the vat type container made of stainless steel.

As soon as the monomer aqueous solution was poured into the vat, polymerization was initiated (temperature at the time of initiation of polymerization 98° C.), and polymerization reached the peak temperature within about 1 minute. After 3 minutes, irradiation of ultraviolet was terminated, and a hydrous polymerization product was taken out. This series of operations were carried out in an open system in air.

An obtained hydrous polymerization product was crushed by a meat chopper (meat-chopper type: 12VR-400KSOX, Iizuka Kogyo, Inc., die orifice diameter: 6.4 mm, number of holes: 38, die thickness 8 mm), and subjected to grain refining, crushed hydrous polymer particles were obtained (mass average particle size 1000 μm).

These subjected to grain refining, crushed hydrous polymer particles were spread on a 50-mesh (mesh size 300 μm) wire gauze, and were subjected to hot air drying at 180° C. The dried product was pulverized with a roll mill, and the particles were classified with JIS standard sieves having a mesh size of 850 μm and a mesh size of 150 μm. Thereby, a water absorbent resin powder (b), which was a water absorbent resin (solid content 96% by mass) in an irregularly shaped crushed form, was obtained. The CRC (water absorption capacity without load) of the water absorbent resin powder (b) was 47.3 [g/g].

Next, the water absorbent resin powder (b) described above was transferred to a rotary mixer manufactured by Deutsche Lödige GmbH, and an aqueous solution of surface cross-linking agent including 0.015 parts by mass of ethylene glycol diglycidyl ether, 1.0 part by mass of propylene glycol, and 3.0 parts by mass of water, was uniformly mixed relative to 100 parts by mass of the water absorbent resin powder (b). The mixture was heat treated for 45 minutes at 100° C. Thereafter, the particle size of the water absorbent resin powder was adjusted using a JIS standard sieve having a mesh size of 850 μm, and thereby water absorbent resin particles (b-1) having the surface cross-linked were obtained. The water absorbent resin particles (b-1) were irregularly shaped, and 95% by mass or more of the particles were included in the range of 150 μm or more but less than 850 μm.

Production Example 3

Water absorbent resin particles (b-2) having the surface cross-linked were obtained by performing the same operations as in Production Example 2, except that the amount of addition of ethylene glycol diglycidyl ether used in Production Example 2 was changed to 0.03 parts by mass.

Comparative Example 1

The water absorbent resin particles (a-1) described in Production Example 1 were designated as comparative water absorbent resin particles (water absorbing agent) (1), and various physical properties thereof are presented in Table 1.

Comparative Example 2

The water absorbent resin particles (b-1) described in Production Example 2 were designated as comparative water absorbent resin particles (2), and various physical properties thereof are presented in Table 1. Furthermore, the results of measuring the particle size of the comparative water absorbent resin particles (2) are presented in Table 3.

Comparative Example 3

The water absorbent resin particles (b-2) described in Production Example 3 were designated as comparative water absorbent resin particles (3), and various physical properties thereof are presented in Table 1.

Example 1

0.3 parts by mass of hydrotalcite (product name: DHT-6, manufactured by Kyowa Chemical Industry Co., Ltd., $Mg_6Al_2(OH)_{16}CO_3.4H_2O$ [in general formula (1), x=0.25, m=0.50], volume average particle size 0.5 μm) was mixed relative to 100 parts by mass of the water absorbent resin particles (b-1) obtained in Production Example 2. Regarding the mixing, 30 g of the water absorbent resin was introduced into a mayonnaise bottle having a capacity of 225 ml together with hydrotalcite, and the content was mixed by vibration (for 3 minutes at room temperature) of a paint shaker (manufactured by Toyo Seiki Seisakusho, Ltd.). Thus, water absorbent resin particles (water absorbing agent) (1) were obtained. The performance of the water absorbent resin particles (1) is presented in the following Table 1. Furthermore, the results of measuring the particle size of the water absorbent resin particles (1) are presented in Table 3. The water absorbent resin particles (1) were such that 98.6% by mass of the particles were included in the particle size range of 150 μm or more but less than 850 μm. Furthermore, the content of hydrotalcite measured by an XRD analysis was 0.3% by mass.

Example 2

0.3 parts by mass of the hydrotalcite used in Example 1 were mixed in the same manner as in Example 1, relative to 100 parts by mass of the water absorbent resin particles (a-1) obtained in Production Example 1, and thus water absorbent resin particles (2) were obtained. The performance of the water absorbent resin particles (2) is presented in the following Table 1. Furthermore, the content of the hydrotalcite measured by an XRD analysis was 0.3% by mass. The water absorbent resin particles (2) were such that 98.5% by mass of the particles were included in the particle size range of 150 μm or more but less than 850 μm.

Example 3

0.3 parts by mass of the hydrotalcite used in Example 1 were mixed in the same manner as in Example 1, relative to 100 parts by mass of the water absorbent resin particles (b-2) obtained in Production Example 3, and thus water absorbent resin particles (3) were obtained. The performance of the water absorbent resin particles (3) is presented in the following Table 1. Furthermore, the content of the hydrotalcite measured by an XRD analysis was 0.3% by mass. The water absorbent resin particles (3) were such that 98.6% by mass of the particles were included in the particle size range of 150 μm or more but less than 850 μm.

Example 4

0.3 parts by mass of hydrotalcite (product name: HT-1-NC, manufactured by Sakai Chemical Industry Co., Ltd., chemical formula: $Mg_4Al_2(OH)_{12}CO_3.3H_2O$ [in general formula (1), x=0.33, m=0.5], volume average particle size 0.58 μm) were mixed in the same manner as in Example 1, relative to 100 parts by mass the water absorbent resin particles (b-1) obtained in Production Example 2, and thus water absorbent resin particles (4) were obtained. The performance of the water absorbent resin particles (4) is presented in the following Table 1. The water absorbent resin particles (4) were such that 98.8% by mass of the particles were included in the particle size range of 150 μm or more but less than 850 μm. The average particle size obtained by measurement of the particle size of hydrotalcite on the water absorbent resin described above was 0.58 μm. Furthermore, the content of the hydrotalcite measured by an XRD analysis was 0.3% by mass.

Example 5

0.2 parts by mass of hydrotalcite (product name: DHT-6, manufactured by Kyowa Chemical Industry Co., Ltd.) were mixed in the same manner as in Example 1, relative to 100 parts by mass of the water absorbent resin particles (b-1) obtained in Production Example 2, and thus water absorbent resin particles (5) were obtained. The performance of the water absorbent resin particles (5) is presented in the following Table 1. Furthermore, the content of hydrotalcite measured by an XRD analysis was 0.2% by mass. The water absorbent resin particles (5) were such that 98.5% by mass of the particles were included in the particle size range of 150 μm or more but less than 850 μm.

Example 6

0.3 parts by mass of hydrotalcite (product name: HT-P, manufactured by Sakai Chemical Industry Co., Ltd., chemical formula: $Mg_{4.5}Al_2(OH)_{13}CO_3 \cdot 3.5H_2O$ [in general formula (1), x=0.69, m=0.54], volume average particle size 0.45 μm) were mixed in the same manner as in Example 1, relative to 100 parts by mass of the water absorbent resin particles (b-1) obtained in Production Example 2, and thus water absorbent resin particles (6) were obtained. The performance of the water absorbent resin particles (6) is presented in the following Table 1. The water absorbent resin particles (6) were such that 98.8% by mass of the particles were included in the particle size range of 150 μm or more but less than 850 μm. The average particle size obtained by measurement of the particle size of hydrotalcite on the water absorbent resin described above was 0.45 μm.

Example 7

Water absorbent resin particles (7) were obtained in the same manner as in Example 1, except that the amount of addition of hydrotalcite in Example 1 was changed to 1.0 part by mass. The performance of the water absorbent resin particles (7) is presented in the following Table 1. Furthermore, the results of measuring the particle size of the water absorbent resin particles (7) are presented in Table 3. Furthermore, the content of the hydrotalcite measured by an XRD analysis was 1.0% by mass. The water absorbent resin particles (7) were such that 99.0% by mass of the particles were included in the particle size range of 150 μm or more but less than 850 μm.

Example 8

Water absorbent resin particles (8) were obtained in the same manner as in Example 1, except that the amount of addition of hydrotalcite of Example 1 was changed to 3.0 parts by mass. The performance of the water absorbent resin particles (8) is presented in the following Table 1. Furthermore, the results of measuring the particle size of the water absorbent resin particles (8) are presented in Table 3. The water absorbent resin particles (8) were such that 98.8% by mass of the particles were included in the particle size range of 150 μm or more but less than 850 μm.

Comparative Example 4

0.3 parts by mass of kaolin (product name: NEOGEN 2000, manufactured by Dry Brabch Kaolin Company) were mixed in the same manner as in Example 1, relative to 100 parts by mass of the water absorbent resin particles (b-1) obtained in Production Example 2, and thus comparative water absorbent resin particles (4) were obtained. The performance of the comparative water absorbent resin particles (4) is presented in the following Table 1.

Comparative Example 5

0.3 parts by mass of kaolin (product name: NEOGEN 2000, manufactured by Dry Brabch Kaolin Company) were mixed in the same manner as in Example 1, relative to 100 parts by mass of the water absorbent resin particles (a-1) obtained in Production Example 1, and thus comparative water absorbent resin particles (5) were obtained. The performance of the comparative water absorbent resin particles (5) is presented in the following Table 1.

Comparative Example 6

0.3 parts by mass of montmorillonite (manufactured by Alfa Aesar Corp., CAS No. 1318-93-0) were mixed in the same manner as in Example 1, relative to 100 parts by mass of the water absorbent resin particles (b-1) obtained in Production Example 2, and thus comparative water absorbent resin particles (6) were obtained. The performance of the comparative water absorbent resin particles (6) is presented in the following Table 1.

Comparative Example 7

0.3 parts by mass of montmorillonite (manufactured by Alfa Aesar Corp., CAS No. 1318-93-0) were mixed in the same manner as in Example 1, relative to 100 parts by mass of the water absorbent resin particles (a-1) obtained in Production Example 1, and thus comparative water absorbent resin particles (7) were obtained. The performance of the comparative water absorbent resin particles (7) is presented in the following Table 1.

Comparative Example 8

0.3 parts by mass of talc (product name: SG-2000, manufactured by Nippon Talc Co., Ltd.) were mixed in the same manner as in Example 1, relative to 100 parts by mass of the water absorbent resin particles (b-1) obtained in Production Example 2, and thus comparative water absorbent resin particles (8) were obtained. The performance of the comparative water absorbent resin particles (8) is presented in the following Table 1.

Comparative Example 9

0.3 parts by mass of silica (product name: AEROSIL 200CF, manufactured by Nippon Aerosil Co., Ltd.) were mixed in the same manner as in Example 1, relative to 100 parts by mass of the water absorbent resin particles (a-1) obtained in Production Example 1, and thus comparative water absorbent resin particles (9) were obtained. The performance of the comparative water absorbent resin particles (9) is presented in the following Table 1.

Comparative Example 10

0.3 parts by mass of silica (product name: AEROSIL 200CF, manufactured by Nippon Aerosil Co., Ltd.) were mixed in the same manner as in Example 1, relative to 100 parts by mass of the water absorbent resin particles (b-1) obtained in Production Example 2, and thus comparative water absorbent resin particles (10) were obtained. The performance of the comparative water absorbent resin particles (10) is presented in the following Table 1.

Comparative Example 11

0.3 parts by mass of laponite (product name: LAPONITE XLG, manufactured by Rockwood Additives, Ltd.) were mixed in the same manner as in Example 1, relative to 100 parts by mass of the water absorbent resin particles (a-1) obtained in Production Example 1, and thus comparative water absorbent resin particles (11) were obtained. The performance of the comparative water absorbent resin particles (11) is presented in the following Table 1.

Comparative Example 12

0.3 parts by mass of laponite (product name: LAPONITE XLG, manufactured by Rockwood Additives, Ltd.) were mixed in the same manner as in Example 1, relative to 100 parts by mass of the water absorbent resin particles (b-1) obtained in Production Example 2, and thus comparative water absorbent resin particles (12) were obtained. The performance of the comparative water absorbent resin particles (12) is presented in the following Table 1.

Comparative Example 13

The water absorbent resin powder (a) obtained in Production Example 1 was mixed in advance with 0.5 parts by mass of kaolin (product name: NEOGEN 2000, manufactured by Dry Brabch Kaolin Company), and the mixture was subjected to the addition of a surface cross-linking agent and to a heating treatment in the same manner as in Production Example 1. Thereby, comparative water absorbent resin particles (13) were obtained. The performance of the comparative water absorbent resin particles (13) is presented in the following Table 1.

Comparative Example 14

Comparative water absorbent resin particles (14) were obtained in the same manner as in Comparative Example 14, except that the amount of use of kaolin used in Comparative Example 13 was changed to 3.0 parts by mass. The performance of the comparative water absorbent resin particles (14) is presented in the following Table 1.

Comparative Example 15

Comparative water absorbent resin particles (15) were obtained in the same manner as in Comparative Example 1, except that when the water absorbent resin powder (a) was subjected to a heating treatment in Production Example 1, the aqueous solution of the surface cross-linking agent described in the production example was mixed with 2.0 parts by mass of kaolin (product name: NEOGEN 2000, manufactured by Dry Brabch Kaolin Company), and the resultant was used as the aqueous solution of surface cross-linking agent and was subjected to a heating treatment. The performance of the comparative water absorbent resin particles (15) is presented in the following Table 1.

Comparative Example 16

0.4 parts by mass of tricalcium phosphate (manufactured by Wako Pure Chemical Industries, Ltd., CAS No. 7758-87-4) were mixed in the same manner, relative to 100 parts by mass of the water absorbent resin particles (b-1) obtained in Production Example 2, and thus comparative water absorbent resin particles (16) were obtained. The amount of dust of the comparative water absorbent resin particles (16) was 192 mg/kg. The additive included in the comparative water absorbent resin particles (16) and the results of the amount of dust are presented in Table 2. The blocking ratio against moisture absorption of the comparative water absorbent resin particles (16) was 0.0% by mass, and the AAP was 31.5 g/g.

Example 9

0.3 parts by mass of tricalcium phosphate (manufactured by Wako Pure Chemical Industries, Ltd., CAS No. 7758-87-4) and 0.1 parts by mass of hydrotalcite (product name: DHT-6, manufactured by Kyowa Chemical Industry Co., Ltd.) were mixed relative to 100 parts by mass of the water absorbent resin particles (b-1) obtained in Production Example 2, and thus water absorbent resin particles (9) were obtained. The amount of dust of the water absorbent resin particles (9) was 129 mg/kg, and the amount of dust was smaller compared with the amount of dust in tricalcium phosphate alone. The additive included in the water absorbent resin particles (9) and the results of the amount of dust are presented in Table 2. The blocking ratio against moisture absorption of the water absorbent resin particles (9) was 0.0% by mass, and the AAP was 31.2 g/g.

Example 10

0.2 parts by mass of tricalcium phosphate (manufactured by Wako Pure Chemical Industries, Ltd., CAS No. 7758-87-4) and 0.2 parts by mass of hydrotalcite (product name: DHT-6, manufactured by Kyowa Chemical Industry Co., Ltd.) were mixed relative to 100 parts by mass of the water absorbent resin particles (b-1) obtained in Production Example 2, and thus water absorbent resin particles (10) were obtained. The amount of dust of the water absorbent resin particles (10) was 70 mg/kg. The additive included in the water absorbent resin particles (10) and the results of the amount of dust are presented in Table 2. The blocking ratio against moisture absorption of the water absorbent resin particles (10) was 0.0% by mass, and the AAP was 30.9 g/g.

Comparative Example 17

0.3 parts by mass of tricalcium phosphate (manufactured by Wako Pure Chemical Industries, Ltd., CAS No. 7758-87-4) and 0.1 parts by mass of kaolin (product name: NEOGEN 2000, manufactured by Dry Brabch Kaolin Company) were mixed relative to 100 parts by mass of the water absorbent resin particles (b-1) obtained in Production Example 2, and thus comparative water absorbent resin particles (17) were obtained. The amount of dust of the comparative water absorbent resin particles (17) was 204 mg/kg. The additive included in the comparative water absorbent resin particles (17) and the results of the amount of dust are presented in Table 2. The blocking ratio against moisture absorption of the comparative water absorbent resin particles (17) was 2.0% by mass, and the AAP was 30.8 g/g.

Comparative Example 18

0.3 parts by mass of tricalcium phosphate (manufactured by Wako Pure Chemical Industries, Ltd., CAS No. 7758-87-4) and 0.1 parts by mass of montmorillonite (manufactured by Alfa Aesar Corp., CAS No. 1318-93-0) were mixed relative to 100 parts by mass of the water absorbent resin particles (b-1) obtained in Production Example 2, and thus comparative water absorbent resin particles (18) were obtained. The amount of dust of the comparative water absorbent resin particles (18) was 230 mg/kg. The additive included in the comparative water absorbent resin particles (18) and the results of the amount of dust are presented in Table 2. The blocking ratio against moisture absorption of the comparative water absorbent resin particles (18) was 1.5% by mass, and the AAP was 31.3 g/g.

TABLE 1

| | | Additive | | | | | | | |
|---|---|---|---|---|---|---|---|---|---|
| | Water absorbent resin | Kind | Particle size (μm) | Amount of addition (wt %) | Time point of addition | CRC g/g | AAP g/g | Blocking ratio, mass % | Amount of dust mg/kg |
| Comparative Example 1 | Production Example 1 | — | — | — | After heating treatment | 43.0 | 29.0 | 100 | 46 |
| Comparative Example 2 | Production Example 2 | — | — | — | After heating treatment | 37.6 | 31.3 | 100 | 65 |
| Comparative Example 3 | Production Example 3 | — | — | — | After heating treatment | 34.5 | 31.9 | 100 | 50 |
| Example 1 | Production Example 2 | DHT-6 | 0.5 | 0.3 | After heating treatment | 37.6 | 30.9 | 0 | 27 |
| Example 2 | Production Example 1 | DHT-6 | 0.5 | 0.3 | After heating treatment | 42.9 | 28.6 | 0 | 30 |
| Example 3 | Production Example 3 | DHT-6 | 0.5 | 0.3 | After heating treatment | 34.5 | 31.2 | 0 | 30 |
| Example 4 | Production Example 2 | HT-1-NC | 0.58 | 0.3 | After heating treatment | 37.6 | 30.6 | 0 | 35 |
| Example 5 | Production Example 2 | DHT-6 | 0.5 | 0.2 | After heating treatment | 38.0 | 31.4 | 24 | 47 |
| Example 6 | Production Example 2 | HT-P | 0.45 | 0.3 | After heating treatment | 37.6 | 31.7 | 0 | 26 |
| Example 7 | Production Example 2 | DHT-6 | 0.5 | 1.0 | After heating treatment | 37.5 | 29.7 | 0 | 22 |
| Example 8 | Production Example 2 | DHT-6 | 0.5 | 3.0 | After heating treatment | 36.4 | 28.2 | 0 | 21 |
| Comparative Example 4 | Production Example 2 | Neogen2000 | 0.7 | 0.3 | After heating treatment | 37.4 | 30.7 | 100 | 110 |
| Comparative Example 5 | Production Example 1 | Neogen2000 | 0.7 | 0.3 | After heating treatment | 42.8 | 28.4 | 96 | 104 |
| Comparative Example 6 | Production Example 2 | Montmorillonite | 0.4 | 0.3 | After heating treatment | 37.7 | 30.4 | 100 | 133 |
| Comparative Example 7 | Production Example 1 | Montmorillonite | 0.4 | 0.3 | After heating treatment | 43.0 | 28.8 | 94 | 129 |
| Comparative Example 8 | Production Example 2 | SG-2000 | 1.0 | 0.3 | After heating treatment | 37.5 | 28.4 | 0 | 150 |
| Comparative Example 9 | Production Example 1 | AEROSIL | 0.012 | 0.3 | After heating treatment | 43.0 | 22.0 | 0 | 67 |
| Comparative Example 10 | Production Example 2 | AEROSIL | 0.012 | 0.3 | After heating treatment | 37.7 | 25.6 | 0 | 174 |
| Comparative Example 11 | Production Example 1 | LAPONITE | 0.025 | 0.3 | After heating treatment | 42.8 | 28.5 | 87 | |

TABLE 1-continued

| | Water absorbent resin | Additive Kind | Particle size (μm) | Amount of addition (wt %) | Time point of addition | CRC g/g | AAP g/g | Blocking ratio, mass % | Amount of dust mg/kg |
|---|---|---|---|---|---|---|---|---|---|
| Comparative Example 12 | Production Example 2 | LAPONITE | 0.025 | 0.3 | After heating treatment | 37.4 | 30.5 | 100 | |
| Comparative Example 13 | Production Example 1 | Neogen2000 | 0.7 | 0.5 | Before heating treatment | 44.6 | 28.0 | 99 | 290 |
| Comparative Example 14 | Production Example 1 | Neogen2000 | 0.7 | 3.0 | Before heating treatment | 40.7 | 25.8 | 0 | 863 |
| Comparative Example 15 | Production Example 1 | Neogen2000 | 0.7 | 2.0 | At the time of heating treatment | 40.5 | 30.1 | 34 | 341 |

TABLE 2

| | Water absorbent resin | Additive Kind (1) | Amount of addition (1) (wt %) | Kind (2) | Particle size (2) (μm) | Amount of addition (2) (wt %) | Amount of dust mg/kg |
|---|---|---|---|---|---|---|---|
| Comparative Example 16 | Production Example 2 | Tricalcium phosphate | 0.4 | — | — | — | 192 |
| Example 9 | Production Example 2 | Tricalcium phosphate | 0.3 | DHT-6 | 0.5 | 0.1 | 129 |
| Example 10 | Production Example 2 | Tricalcium phosphate | 0.2 | DHT-6 | 0.5 | 0.2 | 70 |
| Comparative Example 17 | Production Example 2 | Tricalcium phosphate | 0.3 | Neogen2000 | 0.7 | 0.1 | 204 |
| Comparative Example 18 | Production Example 2 | Tricalcium phosphate | 0.3 | Montmorillonite | 0.4 | 0.1 | 230 |

TABLE 3

| | Water absorbent resin particles: Comparative water absorbent resin particles (2) | Water absorbent resin particles (1) | Water absorbent resin particles (7) | Water absorbent resin particles (8) |
|---|---|---|---|---|
| Additive | Precursor | DHT-6 | DHT-6 | DHT-6 |
| Amount of addition | — | 0.3 wt % | 1.0 wt % | 3.0 wt % |
| 850on | 0.0 | 0.0 | 0.0 | 0.0 |
| 600on | 1.4 | 1.0 | 1.3 | 1.0 |
| 500on | 10.1 | 13.3 | 12.6 | 10.8 |
| 300on | 61.0 | 57.1 | 60.3 | 59.3 |
| 150on | 25.9 | 27.2 | 24.8 | 27.6 |
| 45on | 1.7 | 1.3 | 1.0 | 1.2 |
| pass | 0.1 | 0.0 | 0.0 | 0.0 |
| D50 | 355 | 358 | 363 | 353 |
| σζ | 0.32 | 0.34 | 0.32 | 0.32 |
| 150 thru | 1.73 | 1.36 | 1.02 | 1.27 |

(Summary of Table 1)

It was found that the dust reducer of the present invention reduced the amount of dust to a large extent only through addition of the agent in an amount of 0.3% by mass, and the blocking ratio against moisture absorption was 0%, while the AAP substantially did not decrease (width of decrease: 0.7 g/g or less). Furthermore, even if the amount of addition was increased to 3% by mass, dust did not increase.

When additives other than that were used, the amount of dust increased in all cases, and when the additives were added in an amount that brought the blocking ratio against moisture absorption to 0%, the AAP was decreased to a large extent (width of decrease: 2.9 to 7 g/g).

(Summary of Table 2)

It was found that when other additives were used in combination, only the dust reducer of the present invention could reduce the amount of dust.

(Summary of Table 3)

In regard to the results of measuring the particle size distribution using sieves, it is speculated that even in Example 9 in which the dust reducer of the present invention having an average particle size of 0.5 μm was added in an amount of 3% by mass, the amount of powder having a size of less than 150 μm or less than 45 μm did not increase, and the powder was closely adhered to the water absorbing agent.

(Conclusions)

From Table 1 and Table 3, it is understood not that the dust reducer of the present invention can not be definitely measured according to the dust measurement method of the present specification, but that the dust reducer exhibits its effect by adhering closely to the water absorbent resin. Furthermore, it is understood from Table 2 that not only the dust reducing agent and the water absorbing agent are adhered close to each other, but also, even the amount of dust that is considered to be attributable to the addition of a third particulate component can be reduced.

Production Example 2-1

A water absorbent resin powder was produced as described below, using the apparatus illustrated in FIG. 3 described in US Patent Publication No. 2004/0092688 A1. First, the flow rate of a 48.5 wt % aqueous solution of sodium hydroxide was set to 5.13 g/s, the flow rate of acrylic acid was set to 6.09 g/s, the flow rate of a 30 wt % aqueous solution of polyethylene glycol diacrylate (I) was set to 0.15 g/s, the flow rate of a solution (II) prepared by mixing 50.0 parts by mass of a 1.0 wt % acrylic acid solution of 2-hydroxymethyl-2-methylpropiophenone and 50.0 parts by mass of a 0.54 wt % aqueous solution of trisodium diethylenetriaminepentaacetate (abbreviation: DTPA.3Na, CHELEST PC-45; manufactured by Chelest Corp.) was set to 0.16 g/s, and the flow rate of water was set to 4.63 g/s. Thus, a monomer liquid 20 was produced using the apparatus illustrated in FIG. 3 described in US Patent Publication No. 2004/0092688 A1.

The temperature of this monomer liquid was stabilized at about 95° C. This polyethylene glycol diacrylate as an internal cross-linking agent was such that the average number n of added moles of ethylene oxide was 9. The monomer liquid was stirred in a stirring apparatus which was modified into a static mixer by inserting an element to which a twist of 1.5 rotations at a length of 18.6 mm and a diameter of 6 mm was added, to a pipe having a pipe diameter of 6 mm. Subsequently, a 2 wt % aqueous solution of sodium persulfate as a polymerization initiator was joined at a flow rate of 0.511 g/s at a position on the downstream side about 3 cm away from the end of the element, and thus a mixed liquid 40 was obtained. The mixed liquid 40 was supplied to a belt polymerization apparatus 70 that had an endless belt having a surface which measured 3.8 m in length and 60 cm in width and was coated with a fluororesin, had a UV lamp installed on the belt so that the bottom and the periphery were heated and kept warm at about 100° C., and had an air-intake pipe for collecting evaporated water installed at the center. Thus, polymerization was carried out continuously, and a band-shaped polymerized gel was obtained. Meanwhile, the pipe length from the site of joining the polymerization initiator to the site of ejecting the mixed liquid to the polymerizing machine was 30 cm.

Furthermore, the band-shaped polymerized gel having a surface temperature of about 70° C. was continuously crushed with a meat chopper, and was subjected to hot air drying at 180° C. to obtain a dried product. Subsequently, the polymerized gel was pulverized with a roll mill and was further classified and prepared with JIS standard sieves having mesh sizes of 850 μm and 150 μm. Thereby, a water absorbent resin powder (B−1) having a weight average particle size of 350 μm and a value of 0.36, in which the proportion of particles having a size of less than 150 μm was 2% of the total amount, was obtained. Meanwhile, the CRC (water absorption capacity without load) of the water absorbent resin powder (B−1) was 52.0 [g/g].

Production Example 2-2

A water absorbent resin powder (B-2) was obtained in the same manner as in Production Example 2-1, except that a 2.18 wt % aqueous solution of pentasodium N,N,N',N'-ethylenediaminetetrakismethylenephosphonate (abbreviation: EDTMP.5Na, DEQUEST (registered trademark) 2046; Italmatch Chemicals S.p.A. (31% aqueous solution) diluted) was used instead of the 0.54 wt % aqueous solution of DTPA.3Na.

To briefly explain the apparatus illustrated in FIG. 3 described in US Patent Publication No. 2004/0092688 A1, the apparatus includes a supply mechanism for the monomer liquid 20 on the upstream side of the supply pipe 10. First, the apparatus includes a tank 50 in which an aqueous solution of NaOH (sodium hydroxide) is stored, and a tank 60 in which AA (acrylic acid) is stored. The tanks 50 and 60 are connected to a disperser 56 via pumps 54 and 64, respectively. A cross-linking agent liquid (for example, PEGDA (polyethylene glycol diacrylate), water, other additives (for example, a chelating agent and a photoinitiator), and the like are supplied to a site between the pump 64 and the disperser 56. In the disperser 56, an aqueous solution of NaOH, AA, PEGDA and the like are uniformly neutralized and mixed, and a monomer liquid 20 is thus formed. In this stage, since there is no risk that polymerization and gelling may occur, a monomer liquid 20 having a uniform composition can be obtained by performing sufficient mixing with a conventional disperser 56. Subsequently, the monomer liquid 20 is regulated to a predetermined temperature with a condenser or a heater disposed between the disperser 56 and a stirring apparatus 12. Alternatively, if the disperser 56 is provided with a jacket for temperature regulation or the like, there is no need to install a condenser or a heater after the disperser. Furthermore, temperature adjustment of the monomer liquid 20 can be achieved to a certain extent when the temperatures of the aqueous solution of NaOH, AA and the like that are supplied to the disperser 56 are regulated in advance.

The monomer liquid 20 is vortexed by the stirring apparatus 12, and then is joined with a polymerization initiator 30 (for example, an aqueous solution of sodium persulfate) through a pipe 14. The monomer liquid 20 coming out from the disperser 56 may be vortexed by stirring and mixing by the disperser 56 in some occasions, and in that case, the polymerization initiator 30 may be joined here, and the disperser 56 can also be used in combination as the stirring apparatus 12. A supply port (discharge port) on the downstream side of the supply pipe 10 is provided above a belt conveyor 70 that constitutes a polymerization apparatus. The mixed liquid 40 is discharged on the conveyor belt and undergoes polymerization on the conveyor belt, and thus a polymerized gel 42 of a band-shaped water absorbent resin is formed.

Production Example 2-3

A water absorbent resin powder (B-3) was obtained in the same manner as in Production Example 2-1, except that a 5.45 wt % aqueous solution of EDTMP.5Na was used instead of the 0.54 wt % aqueous solution of DTPA.3Na.

Production Example 2-4

A water absorbent resin powder (B-4) was obtained in the same manner as in Production Example 2-1, except that a 10.9 wt % aqueous solution of pentasodium N,N,N',N'-ethylenediaminetetrakismethylenephosphonate (abbreviation: EDTMP.5Na, DEQUEST (registered trademark) 2046; Italmatch Chemicals S.p.A. (31% aqueous solution) diluted) was used instead of the 0.54 wt % aqueous solution of DTPA.3Na.

Production Example 2-5

A water absorbent resin powder (B-5) was obtained in the same manner as in Production Example 2-1, except that a 10.9 wt % aqueous solution of DTPA.3Na was used instead of the 0.54 wt % aqueous solution of DTPA.3Na.

Comparative Example 2-1

In 5500 g of an aqueous solution of sodium acrylate having the neutralization rate of 75% by mole (monomer concentration: 35% by mass), 0.38 g of trimethylolpropane triacrylate (molecular weight 296) (0.006% by mole relative to the monomer) was dissolved, and a monomer aqueous solution (a) was prepared. Subsequently, the monomer aqueous solution was degassed for 30 minutes in a nitrogen gas atmosphere.

Next, the monomer aqueous solution (a) was introduced into a reactor produced by providing a lid to a double blade type jacketed kneader made of stainless steel with an internal capacity of 10 L and having two sigma-shaped blades. Nitrogen gas was blown into the reactor while the liquid temperature was maintained at 30° C., and the reactor was purged with nitrogen such that the dissolved oxygen in the system would be 1 ppm or less.

Subsequently, 24.6 g of a 10 mass % aqueous solution of sodium persulfate and 21.8 g of a 0.2 mass % aqueous solution of L-ascorbic acid were separately added to the monomer aqueous solution (a) with stirring, and polymerization was initiated after about 1 minute. While the produced water-containing gel-like cross-linked polymer (a) was crushed, polymerization was performed at 30° C. to 90° C., and when 60 minutes had passed from the initiation of polymerization, a water-containing gel-like cross-linked polymer (a) was taken out from the reactor. The water-containing gel-like cross-linked polymer (a) thus obtained was subjected to grain refining to particles having a diameter of about 5 mm.

The water-containing gel-like cross-linked polymer (a) thus subjected to grain refining described above was spread on a wire gauze having a mesh size of 300 μm (50-mesh) and dried under hot air for 45 minutes at 180° C. Subsequently, the cross-linked polymer was pulverized with a roll mill, and was classified with JIS standard sieves having mesh sizes of 850 μm and 150 μm. Through this series of operations, a water absorbent resin powder (a), which was a water absorbent resin (solid content 4.0% by mass) in an irregularly shaped crushed form, was obtained. The CRC (water absorption capacity without load) of the water absorbent resin powder (a) was 53.0 [g/g].

Next, the water absorbent resin powder (a) was transferred into a rotary mixer manufactured by Deutsche Lödige GmbH, and an aqueous solution of surface cross-linking agent including 0.015 parts by mass of ethylene glycol diglycidyl ether (trade name: DENACOL EX-810 manufactured by Nagase ChemteX Corp.), 1.5 parts by mass of 1,2-propanediol (melting point−59° C.), and 3.5 parts by mass of water that had been warmed to 40° C., was uniformly mixed relative to 100 parts by mass of the water absorbent resin powder (a). The mixture was heat treated for 45 minutes at 100° C. Thereafter, the particle size of the water absorbent resin powder was adjusted using a JIS standard sieve having a mesh size of 850 μm, and thereby comparative water absorbent resin particles (surface cross-linked water absorbent resin) (a-2) were obtained. The comparative water absorbent resin particles (a-2) were irregularly shaped, and 95% by mass or more of the particles were included in the range of 150 μm or more but less than 850 μm. The comparative water absorbent resin particles (surface cross-linked water absorbent resin) (a-2) are regarded as the comparative water absorbent resin particles (water absorbing agent) (2-1), and performance thereof is shown in Table 2-2.

Comparative Example 2-2

The water absorbent resin powder (a) obtained in Comparative Example 2-1 was transferred to a rotary mixer manufactured by Deutsche Lödige GmbH, and an aqueous solution of surface cross-linking agent including 0.025 parts by mass of ethylene glycol diglycidyl ether (trade name: DENACOL EX-810 manufactured by Nagase ChemteX Corp.), 0.3 parts by mass of ethylene carbonate (melting point 36° C.) that had been warmed to 40° C. in advance, 0.5 parts by mass of 1,2-propanediol (melting point−59° C.), and 3.0 parts by mass of water that had been warmed to 40° C., was uniformly mixed relative to 100 parts by mass of the water absorbent resin powder (a). The mixture was heat treated for 40 minutes at 175° C. Thereafter, the mixture was passed through a JIS standard sieve having a mesh size of 850 μm, and thereby comparative water absorbent resin particles (surface cross-linked water absorbent resin) (a-1) were obtained. The comparative water absorbent resin particles (a-1) were irregularly shaped, and 95% by mass or more of the particles were included in the range of 150 μm or more but less than 850 μm. These comparative water absorbent resin particles (a-1) are regarded as the comparative water absorbent resin particles (water absorbing agent) (2-2), and performance thereof is shown in Table 2-2.

Comparative Example 2-3

An aqueous solution of surface cross-linking agent including 0.025 parts by mass of ethylene glycol diglycidyl ether (trade name: DENACOL EX-810, manufactured by Nagase ChemteX Corp.), 1.5 parts by mass of 1,2-propanediol (melting point−59° C.), and 3.5 parts by mass of water that had been warmed to 40° C., was uniformly mixed relative to 100 parts by mass of the water absorbent resin powder (B−1) obtained in Production Example 2-1. The mixture was heat treated for 45 minutes at 100° C. Thereafter, the particle size of the water absorbent resin powder was adjusted using a JIS standard sieve having a mesh size of 850 μm, and thereby water absorbent resin particles having the surface cross-linked were obtained.

Next, a mixed liquid including 0.01 parts by mass of DTPA.3Na and 1 part by mass of water, was uniformly mixed relative to 100 parts by mass of the water absorbent resin particles having the surface cross-linked. The mixture was granulated and then heat treated for 45 minutes at 60° C. Thereafter, the particle size of the water absorbent resin particles was adjusted using a JIS standard sieve having a mesh size of 850 μm, and thereby granulated comparative water absorbent resin particles (2-3) were obtained. The comparative water absorbent resin particles (2-3) were irregularly shaped, and 95% by mass or more of the particles were included in the range of 150 μm or more but less than 850 μm. The performance of the comparative water absorbent resin particles (2-3) is presented in Table 2-2.

Comparative Example 2-4

An aqueous solution of surface cross-linking agent including 0.025 parts by mass of ethylene glycol diglycidyl ether (trade name: DENACOL EX-810 manufactured by Nagase ChemteX Corp.), 0.3 parts by mass of ethylene carbonate (melting point 36° C.) that had been warmed to 40° C. in advance, 0.5 parts by mass of 1,2-propanediol (melting point−59° C.), and 3.0 parts by mass of water that had been warmed to 40° C., was uniformly mixed relative to 100 parts by mass of the water absorbent resin powder (B−1) obtained in Production Example 2-1. The mixture was heat treated for 40 minutes at 175° C. Thereafter, the particle size of the water absorbent resin powder was adjusted using a JIS standard sieve having a mesh size of 850 μm, and thereby water absorbent resin particles having the surface cross-linked were obtained.

Next, a mixed liquid including 0.01 parts by mass of DTPA.3Na and 1 part by mass of water, was uniformly mixed relative to 100 parts by mass of the water absorbent resin particles having the surface cross-linked. The mixture was granulated and then heat treated for 45 minutes at 60° C. Thereafter, the particle size of the water absorbent resin particles was adjusted using a JIS standard sieve having a mesh size of 850 μm, and thereby comparative water absorbent resin particles (2-4) were obtained. The performance of the comparative water absorbent resin particles (2-4) is presented in Table 2-2.

Example 2-1

0.3 parts by weight of hydrotalcite (product name: DHT-6, manufactured by Kyowa Chemical Industry Co., Ltd, $Mg_6Al_2(OH)_{16}CO_3.4H_2O$ [in general formula (1), x=0.25, m=0.50], volume average particle size 0.5 μm) were mixed relative to 100 parts by mass of the granulated comparative water absorbent resin particles (surface cross-linked water absorbent resin) (2-3) produced in Comparative Example 2-3. Regarding the mixing, 30 g of the water absorbent resin was introduced into a mayonnaise bottle having a capacity of 225 mL together with hydrotalcite, and the content was mixed for 3 minutes by vibration of a paint shaker (manufactured by Toyo Seiki Seisakusho Co., Ltd.). Thus, water absorbent resin particles (2-1) were obtained. The water absorbent resin particles (2-1) were such that 95% by mass of the particles were included in the particle size range of 150 μm or more but less than 850 μm. The performance of the water absorbent resin particles (2-1) is presented in Table 2-2.

Example 2-2

Water absorbent resin particles (2-2) were obtained in the same manner as in Example 2-1, except that a mixed liquid including 1.5 parts by mass of sodium dihydrogen phosphate and 3.5 parts by mass of water was used for the surface cross-linked water absorbent resin particles, instead of the mixed liquid including 0.01 parts by mass of DTPA.3Na and 1 part by mass of water. The water absorbent resin particles (2-2) were such that 95% by mass or more of the particles were included in the particle size range of 150 μm or more but less than 850 μm. The performance of the water absorbent resin particles (2-2) is presented in Table 2-2.

Example 2-3

An aqueous solution of surface cross-linking agent including 0.025 parts by mass of ethylene glycol diglycidyl ether (trade name: DENACOL EX-810, manufactured by Nagase ChemteX Corp.), 1.5 parts by mass of 1,2-propanediol (melting point−59° C.), and 3.5 parts by mass of water that had been warmed to 40° C., was uniformly mixed relative to 100 parts by mass of the water absorbent resin powder (B-2) obtained in Production Example 2-2. The mixture was heat treated for 45 minutes at 100° C. Thereafter, the particle size of the water absorbent resin powder was adjusted using a JIS standard sieve having a mesh size of 850 μm, and thereby water absorbent resin particles having the surface cross-linked were obtained.

Next, 0.3 parts by mass of the hydrotalcite used in Example 2-1 was mixed in the same manner as in Example 2-1, and water absorbent resin particles (2-3) were obtained. The water absorbent resin particles (2-3) were such that 95% by mass or more of the particles were included in the particle size range of 150 μm or more but less than 850 μm. The performance of the water absorbent resin particles (2-3) is presented in Table 2-2.

Example 2-4

Water absorbent resin particles (2-4) were obtained by the same manner as that used in Example 2-3, except that the hydrotalcite was changed from DHT-6 to DHT-4H (manufactured by Kyowa Chemical Industry Co., Ltd., chemical formula: $Mg_{4.5}Al_2(OH)_{13}CO_3.3.5H_2O$ [in general formula (1), x=0.31, m=0.54], volume average particle size 0.4 μm). The water absorbent resin particles (2-4) were such that 95% by mass or more of the particles were included in the particle size of 150 μm or more but less than 850 μm. The performance of the water absorbent resin particles (2-4) is presented in Table 2-2.

Example 2-5

Water absorbent resin particles (2-5) were obtained by the same manner as that used in Example 2-3, except that the hydrotalcite was changed from DHT-6 to HT-1-NC (manufactured by Sakai Chemical Industry Co., Ltd., chemical formula: $Mg_4Al_2(OH)_{12}CO_3.3H_2O$ [in general formula (1), x=0.33, m=0.5], volume average particle size 0.58 μm). The water absorbent resin particles (2-5) were such that 95% by mass or more of the particles were included in the particle size of 150 μm or more but less than 850 μm. The performance of the water absorbent resin particles (2-5) is presented in Table 2-2.

Example 2-6

Water absorbent resin particles (2-6) were obtained by the same method as that used in Example 2-1, except that a mixed liquid including 0.03 parts by mass of DTPA.3Na, 0.5 parts by mass of sodium bisulfite and 3.5 parts by mass of water was used in the surface cross-linked water absorbent resin particles, instead of the mixed liquid including 0.01 parts by mass of DTPA.3Na and 1 part by mass of water. The water absorbent resin particles (2-6) were such that 95% by mass or more of the particles were included in the particle size of 150 μm or more but less than 850 μm. The performance of the water absorbent resin particles (2-6) is presented in Table 2-2.

Example 2-7

An aqueous solution of surface cross-linking agent including 0.025 parts by mass of ethylene glycol diglycidyl ether (trade name: DENACOL EX-810, manufactured by Nagase ChemteX Corp.), 1.5 parts by mass of 1,2-propanediol (melting point−59° C.), and 3.5 parts by mass of water that had been warmed to 40° C., was uniformly mixed relative to 100 parts by mass of the water absorbent resin powder (B-2) obtained in Production Example 2-2. The mixture was heat treated for 45 minutes at 100° C. Thereafter, the particle size of the water absorbent resin powder was adjusted using a JIS standard sieve having a mesh size of 850 μm, and thereby water absorbent resin particles having the surface cross-linked were obtained.

Next, a mixed liquid including 0.44 parts by mass of sodium dihydrogen phosphate and 3.5 parts by mass of water, was uniformly mixed relative to 100 parts by mass of the water absorbent resin particles having the surface cross-linked. The mixture was granulated and then heat treated for 45 minutes at 60° C. Thereafter, the particle size of the water absorbent resin particles was adjusted using a JIS standard sieve having a mesh size of 850 μm, and thereby granulated water absorbent resin particles were obtained.

Next, 0.3 parts by mass of the hydrotalcite used in Example 2-1 was mixed in the same manner as in Example 2-1, and water absorbent resin particles (2-7) were obtained. The water absorbent resin particles (2-7) were such that 95% by mass or more of the particles were included in the particle size range of 150 μm or more but less than 850 μm. The performance of the water absorbent resin particles (2-7) is presented in Table 2-2.

Example 2-8

Water absorbent resin particles (2-8) were obtained by the same operation as that used in Example 2-7, except that the amount of hydrotalcite used in Example 2-7 was changed from 0.3 parts by mass to 0.5 parts by mass. The water absorbent resin particles (2-8) were such that 95% by mass or more of the particles were included in the particle size range of 150 μm or more but less than 850 μm. The performance of the water absorbent resin particles (2-8) is presented in Table 2-2.

Example 2-9

Water absorbent resin particles (2-9) were obtained by the same operation as that used in Example 2-7, except that the amount of sodium dihydrogen phosphate used in Example 2-7 was changed from 0.44 parts by mass to 1.0 part by mass. The water absorbent resin particles (2-9) were such that 95% by mass or more of the particles were included in the particle size range of 150 μm or more but less than 850 μm. The performance of the water absorbent resin particles (2-9) is presented in Table 2-2.

Example 2-10

Water absorbent resin particles (2-10) were obtained by the same operation as that used in Example 2-7, except that 0.44 parts by mass of sodium dihydrogen phosphate used in Example 2-7 was changed to disodium hydrogen phosphate. The water absorbent resin particles (2-10) were such that 95% by mass or more of the particles were included in the particle size range of 150 μm or more but less than 850 μm. The performance of the water absorbent resin particles (2-10) is presented in Table 2-2.

Example 2-11

Water absorbent resin particles (2-11) were obtained by the same operation as that used in Example 2-7, except that 0.44 parts by mass of sodium dihydrogen phosphate used in Example 2-7 was changed to 0.5 parts by mass of trisodium phosphate. The water absorbent resin particles (2-11) were such that 95% by mass or more of the particles were included in the particle size range of 150 μm or more but less than 850 The performance of the water absorbent resin particles (2-11) is presented in Table 2-2.

Example 2-12

A surface treating agent including 0.025 parts by mass of ethylene glycol diglycidyl ether (trade name: DENACOL EX-810, manufactured by Nagase ChemteX Corp.), 0.3 parts by mass of ethylene carbonate (melting point 36° C.) that had been warmed to 40° C. in advance, 0.5 parts by mass of 1,2-propanediol (melting point−59° C.), and 3.0 parts by mass of water that had been warmed to 40° C., was uniformly mixed relative to 100 parts by mass of the water absorbent resin powder (B-2) obtained in Production Example 2-2. The mixture was heat treated for 40 minutes at 175° C. Thereafter, the particle size of the water absorbent resin powder was adjusted using a JIS standard sieve having a mesh size of 850 μm, and thereby water absorbent resin particles having the surface cross-linked were obtained.

Next, a mixed liquid including 0.5 parts by mass of tripolyphosphoric acid and 3.5 parts by mass of water, was uniformly mixed relative to 100 parts by mass of the water absorbent resin particles having the surface cross-linked. The mixture was granulated and then heat treated for 45 minutes at 60° C. Thereafter, the particle size of the water absorbent resin particles was adjusted using a JIS standard sieve having a mesh size of 850 μm, and thereby granulated water absorbent resin particles were obtained.

Next, 0.3 parts by mass of the hydrotalcite used in Example 2-1 was mixed in the same manner as in Example 2-1, and water absorbent resin particles (2-12) were obtained. The water absorbent resin particles (2-12) were such that 95% by mass or more of the particles were included in the particle size range of 150 μm or more but less than 850 μm. The performance of the water absorbent resin particles (2-12) is presented in Table 2-2.

Example 2-13

Water absorbent resin particles (2-13) were obtained by the same operation as that used in Example 2-12, except that 0.5 parts by mass of tripolyphosphoric acid used in Example 2-12 was changed to 0.5 parts by mass of hexametaphosphoric acid. The water absorbent resin particles (2-13) were such that 95% by mass or more of the particles were included in the particle size range of 150 μm or more but less than 850 μm. The performance of the water absorbent resin particles (2-13) is presented in Table 2-2.

Example 2-14

Water absorbent resin particles (2-14) were obtained by the same operation as that used in Example 2-7, except that 0.44 parts by mass of sodium dihydrogen phosphate used in Example 2-7 was changed to 0.1 parts by mass of sodium bisulfite. The water absorbent resin particles (2-14) were such that 95% by mass or more of the particles were included in the particle size range of 150 μm or more but less than 850 μm. The performance of the water absorbent resin particles (2-14) is presented in Table 2-2.

Example 2-15

Water absorbent resin particles (2-15) were obtained by the same operation as that used in Example 2-14, except that the amount of sodium bisulfite used in Example 2-14 was changed from 0.1 parts by mass to 1 part by mass. The water absorbent resin particles (2-15) were such that 95% by mass or more of the particles were included in the particle size range of 150 μm or more but less than 850 μm. The performance of the water absorbent resin particles (2-15) is presented in Table 2-2.

Example 2-16

Water absorbent resin particles (2-16) were obtained by the same operation as that used in Example 2-14, except that 0.1 parts by mass of sodium bisulfite used in Example 2-14 was changed to 0.05 parts by mass of 2-hydroxy-2-sulfinatoacetic acid. The water absorbent resin particles (2-15) were such that 95% by mass or more of the particles were included in the particle size range of 150 μm or more but less than 850 μm. The performance of the water absorbent resin particles (2-16) is presented in Table 2-2.

Example 2-17

Water absorbent resin particles (2-17) were obtained by the same operation as that used in Example 2-16, except that the amount of 2-hydroxy-2-sulfinatoacetic acid used in Example 2-16 was changed from 0.05 parts by mass to 0.5 parts by weight. The water absorbent resin particles (2-17) were such that 95% by mass or more of the particles were included in the particle size range of 150 μm or more but less than 850 μm. The performance of the water absorbent resin particles (2-17) is presented in Table 2-2.

Example 2-18

Water absorbent resin particles (2-18) were obtained by the same operation as that used in Example 2-12, except that 0.5 parts by mass of tripolyphosphoric acid used in Example 2-12 was changed to 0.2 parts by mass of hypophosphorous acid. The water absorbent resin particles (2-18) were such that 95% by mass or more of the particles were included in the particle size range of 150 μm or more but less than 850 μm. The performance of the water absorbent resin particles (2-18) is presented in Table 2-2.

Example 2-19

Water absorbent resin particles (2-19) were obtained by the same operation as that used in Example 2-18, except that the amount of hypophosphorous acid used in Example 2-18 was changed from 0.2 parts by mass to 1.0 part by mass. The water absorbent resin particles (2-19) were such that 95% by mass or more of the particles were included in the particle size range of 150 μm or more but less than 850 μm. The performance of the water absorbent resin particles (2-19) is presented in Table 2-2.

Example 2-20

Water absorbent resin particles (2-20) were obtained by the same operation as that used in Example 2-7, except that 0.44 parts by mass of sodium dihydrogen phosphate used in Example 2-7 was changed to 0.5 parts by mass of DL-malic acid. The water absorbent resin particles (2-20) were such that 95% by mass or more of the particles were included in the particle size range of 150 μm or more but less than 850 μm. The performance of the water absorbent resin particles (2-20) is presented in Table 2-2.

Example 2-21

Water absorbent resin particles (2-21) were obtained by the same operation as that used in Example 2-20, except that the amount of DL-malic acid used in Example 2-20 was changed from 0.5 parts by mass to 1.5 parts by mass. The water absorbent resin particles (2-21) were such that 95% by mass or more of the particles were included in the particle size range of 150 μm or more but less than 850 μm. The performance of the water absorbent resin particles (2-21) is presented in Table 2-2.

Example 2-22

An aqueous solution of surface cross-linking agent including 0.025 parts by mass of ethylene glycol diglycidyl ether (trade name: DENACOL EX-810, manufactured by Nagase ChemteX Corp.), 1.5 parts by mass of 1,2-propanediol (melting point−59° C.), and 3.5 parts by mass of water that had been warmed to 40° C., was uniformly mixed relative to 100 parts by mass of the water absorbent resin powder (B-3) obtained in Production Example 2-3. The mixture was heat treated for 45 minutes at 100° C. Thereafter, the particle size of the water absorbent resin powder was adjusted using a JIS standard sieve having a mesh size of 850 μm, and thereby water absorbent resin particles having the surface cross-linked were obtained.

Next, 0.3 parts by mass of the hydrotalcite used in Example 2-1 was mixed in the same manner as in Example 2-1, and water absorbent resin particles (2-22) were obtained. The water absorbent resin particles (2-22) were such that 95% by mass or more of the particles were included in the particle size range of 150 μm or more but less than 850 μm. The performance of the water absorbent resin particles (2-22) is presented in Table 2-2.

Example 2-23

An aqueous solution of surface cross-linking agent including 0.025 parts by mass of ethylene glycol diglycidyl ether (trade name: DENACOL EX-810, manufactured by Nagase ChemteX Corp.), 1.5 parts by mass of 1,2-propanediol (melting point−59° C.), and 3.5 parts by mass of water that had been warmed to 40° C., was uniformly mixed relative to 100 parts by mass of the water absorbent resin powder (B-5) obtained in Production Example 2-5. The mixture was heat treated for 45 minutes at 100° C. Thereafter, the particle size of the water absorbent resin powder was adjusted using a JIS standard sieve having a mesh size of 850 μm, and thus water absorbent resin particles having the surface cross-linked were obtained.

Next, 0.3 parts by mass of the hydrotalcite used in Example 2-1 was mixed in the same manner as in Example 2-1, and water absorbent resin particles (2-23) were obtained. The water absorbent resin particles (2-23) were such that 95% by mass or more of the particles were included in the particle size range of 150 μm or more but less than 850 μm. The performance of the water absorbent resin particles (2-23) is presented in Table 2-2.

Example 2-24

An aqueous solution of surface cross-linking agent including 0.025 parts by mass of ethylene glycol diglycidyl ether (trade name: DENACOL EX-810, manufactured by Nagase ChemteX Corp.), 1.5 parts by mass of 1,2-propanediol (melting point−59° C.), and 3.5 parts by mass of water that had been warmed to 40° C., was uniformly mixed relative to 100 parts by mass of the water absorbent resin powder (B−1) obtained in Production Example 2-1. The mixture was heat treated for 45 minutes at 100° C. Thereafter, the particle size of the water absorbent resin powder was adjusted using a JIS standard sieve having a mesh size of 850 μm, and thereby water absorbent resin particles having the surface cross-linked were obtained.

Next, a mixed liquid including 0.095 parts by mass of DTPA.3Na and 1 part by mass of water, was uniformly mixed relative to 100 parts by mass of the water absorbent resin particles having the surface cross-linked. The mixture was granulated and then heat treated for 45 minutes at 60° C. Thereafter, the particle size of the water absorbent resin particles was adjusted using a JIS standard sieve having a mesh size of 850 μm, and thereby granulated water absorbent resin particles (2-24) were obtained. The water absorbent resin particles (2-24) were irregularly shaped, and 95% by mass or more of the particles were included in the range of 150 μm or more but less than 850 μm. The performance of the water absorbent resin particles (2-24) is presented in Table 2-2.

Example 2-25

An aqueous solution of surface cross-linking agent including 0.025 parts by mass of ethylene glycol diglycidyl ether (trade name: DENACOL EX-810, manufactured by Nagase ChemteX Corp.), 1.5 parts by mass of 1,2-propanediol (melting point−59° C.), and 3.5 parts by mass of water that had been warmed to 40° C., was uniformly mixed relative to 100 parts by mass of the water absorbent resin powder (B-4) obtained in Production Example 2-4. The mixture was heat treated for 45 minutes at 100° C. Thereafter, the particle size of the water absorbent resin powder was adjusted using a JIS standard sieve having a mesh size of 850 μm, and thereby water absorbent resin particles having the surface cross-linked were obtained.

Next, 0.3 parts by mass of the hydrotalcite used in Example 2-1 was mixed in the same manner as in Example 2-1, and water absorbent resin particles (2-25) were obtained. The water absorbent resin particles (2-25) were such that 95% by mass or more of the particles were included in the particle size range of 150 μm or more but less than 850 μm. The performance of the water absorbent resin particles (2-25) is presented in Table 2-2.

Example 2-26

An aqueous solution of surface cross-linking agent including 0.025 parts by mass of ethylene glycol diglycidyl ether (trade name: DENACOL EX-810, manufactured by Nagase ChemteX Corp.), 1.5 parts by mass of 1,2-propanediol (melting point−59° C.), and 3.5 parts by mass of water that had been warmed to 40° C., was uniformly mixed relative to 100 parts by mass of the water absorbent resin powder (B-2) obtained in Production Example 2-2. The mixture was heat treated for 45 minutes at 100° C. Thereafter, the particle size of the water absorbent resin powder was adjusted using a JIS standard sieve having a mesh size of 850 μm, and thereby water absorbent resin particles having the surface cross-linked were obtained.

Next, a mixed liquid including 0.08 parts by mass of pentasodium N,N,N',N'-ethylenediaminetetrakismethylenephosphonate (abbreviation: EDTMP.5Na, DEQUEST (registered trademark) 2046; Italmatch Chemicals S.p.A. (31% aqueous solution) diluted) and 1 parts by mass of water, was uniformly mixed relative to 100 parts by mass of the water absorbent resin particles having the surface cross-linked. The mixture was granulated and then heat treated for 45 minutes at 60° C. Thereafter, the particle size of the water absorbent resin particles was adjusted using a JIS standard sieve having a mesh size of 850 μm, and thereby granulated water absorbent resin particles (2-26) were obtained. The water absorbent resin particles (2-26) were irregularly shaped, and 95% by mass or more of the particles were included in the range of 150 μm or more but less than 850 μm. The performance of the water absorbent resin particles (2-26) is presented in Table 2-2.

Comparative Example 2-5

Comparative water absorbent resin particles (2-5) were obtained by the same method as that used in Example 2-3, except that 0.3 parts by mass of hydrotalcite was changed to 0.3 parts by mass of silica (product name: AEROSIL 200CF, manufactured by Nippon Aerosil Co., Ltd.). The water absorbent resin particles (2-5) were such that 95% by mass or more of the particles were included in the particle size range of 150 μm or more but less than 850 The performance of the water absorbent resin particles (2-5) is presented in Table 2-2.

Comparative Example 2-6

Comparative water absorbent resin particles (2-6) were obtained by the same method as that used in Example 2-3, except that 0.3 parts by mass of hydrotalcite was changed to 0.3 parts by mass of magnesium hydroxide (manufactured by Wako Pure Chemical Industries, Ltd.). The water absorbent resin particles (2-6) were such that 95% by mass or more of the particles were included in the particle size range of 150 μm or more but less than 850 μm. The performance of the water absorbent resin particles (2-6) is presented in Table 2-2.

TABLE 2-1

| | | Additive 1 | | | Additive 2 | | | Additive 3 | | |
|---|---|---|---|---|---|---|---|---|---|---|
| | Water absorbent resin | Kind | Time point of addition | Amount of addition ppm | Kind | Time point of addition | Amount of addition ppm | Kind | Time point of addition | Amount of addition mass % |
| Comparative Example 2-1 | Comparative Example 2-1 | — | — | — | — | | — | — | — | — |
| Comparative Example 2-2 | Comparative Example 2-1 | — | — | — | — | | — | — | — | — |
| Comparative Example 2-3 | Production Example 2-1 | DTPA•3Na | Polymerization | 50 | DTPA•3Na | After heating treatment | 100 | — | — | — |
| Comparative Example 2-4 | Production Example 2-1 | DTPA•3Na | Polymerization | 50 | DTPA•3Na | After heating treatment | 100 | — | — | — |

TABLE 2-1-continued

| | Water absorbent resin | Additive 1 Kind | Additive 1 Time point of addition | Additive 1 Amount of addition ppm | Additive 2 Kind | Additive 2 Time point of addition | Additive 2 Amount of addition ppm | Additive 3 Kind | Additive 3 Time point of addition | Additive 3 Amount of addition mass % |
|---|---|---|---|---|---|---|---|---|---|---|
| Example 2-1 | Production Example 2-1 | DTPA•3Na | Polymerization | 50 | DTPA•3Na | After heating treatment | 100 | DHT-6 | After addition of additive 2 | 0.3 |
| Example 2-2 | Production Example 2-1 | DTPA•3Na | Polymerization | 50 | $NaH_2PO4$ | After heating treatment | 15000 | DHT-6 | After addition of additive 2 | 0.3 |
| Example 2-3 | Production Example 2-2 | EDTMP•5Na | Polymerization | 200 | — | — | — | DHT-6 | After heating treatment | 0.3 |
| Example 2-4 | Production Example 2-2 | EDTMP•5Na | Polymerization | 200 | — | — | — | DHT-4H | After heating treatment | 0.3 |
| Example 2-5 | Production Example 2-2 | EDTMP•5Na | Polymerization | 200 | — | — | — | HT-1-NC | After heating treatment | 0.3 |
| Example 2-6 | Production Example 2-1 | DTPA•3Na | Polymerization | 50 | DTPA•3Na + SBS | After heating treatment | 300 + 5000 | DHT-6 | After addition of additive 2 | 0.3 |
| Example 2-7 | Production Example 2-2 | EDTMP•5Na | Polymerization | 200 | $NaH_2PO_4$ | After heating treatment | 4400 | DHT-6 | After addition of additive 2 | 0.3 |
| Example 2-8 | Production Example 2-2 | EDTMP•5Na | Polymerization | 200 | $NaH_2PO_4$ | After heating treatment | 4400 | DHT-6 | After addition of additive 2 | 0.5 |
| Example 2-9 | Production Example 2-2 | EDTMP•5Na | Polymerization | 200 | $NaH_2PO_4$ | After heating treatment | 10000 | DHT-6 | After addition of additive 2 | 0.3 |
| Example 2-10 | Production Example 2-2 | EDTMP•5Na | Polymerization | 200 | $Na_2HPO_4$ | After heating treatment | 5000 | DHT-6 | After addition of additive 2 | 0.3 |
| Example 2-11 | Production Example 2-2 | EDTMP•5Na | Polymerization | 200 | $Na_3PO_4$ | After heating treatment | 5000 | DHT-6 | After addition of additive 2 | 0.3 |
| Example 2-12 | Production Example 2-2 | EDTMP•5Na | Polymerization | 200 | Tripolyphosphoric acid | After heating treatment | 5000 | DHT-6 | After addition of additive 2 | 0.3 |
| Example 2-13 | Production Example 2-2 | EDTMP•5Na | Polymerization | 200 | Hexameta-phosphoric acid | After heating treatment | 5000 | DHT-6 | After addition of additive 2 | 0.3 |
| Example 2-14 | Production Example 2-2 | EDTMP•5Na | Polymerization | 200 | SBS | After heating treatment | 1000 | DHT-6 | After addition of additive 2 | 0.3 |
| Example 2-15 | Production Example 2-2 | EDTMP•5Na | Polymerization | 200 | SBS | After heating treatment | 10000 | DHT-6 | After addition of additive 2 | 0.3 |
| Example 2-16 | Production Example 2-2 | EDTMP•5Na | Polymerization | 200 | 2-Hydroxy-2-sulfinatoacetic acid•2Na | After heating treatment | 500 | DHT-6 | After addition of | 0.3 |

TABLE 2-1-continued

| | Water absorbent resin | Additive 1 Kind | Additive 1 Time point of addition | Additive 1 Amount of addition ppm | Additive 2 Kind | Additive 2 Time point of addition | Additive 2 Amount of addition ppm | Additive 3 Kind | Additive 3 Time point of addition | Additive 3 Amount of addition mass % |
|---|---|---|---|---|---|---|---|---|---|---|
| | | | | | | | | | additive 2 | |
| Example 2-17 | Production Example 2-2 | EDTMP•5Na | Polymerization | 200 | 2-Hydroxy-2-sulfinatoacetic acid•2Na | After heating treatment | 5000 | DHT-6 | After addition of additive 2 | 0.3 |
| Example 2-18 | Production Example 2-2 | EDTMP•5Na | Polymerization | 200 | Hypophosphorous acid | After heating treatment | 2000 | DHT-6 | After addition of additive 2 | 0.3 |
| Example 2-19 | Production Example 2-2 | EDTMP•5Na | Polymerization | 200 | Hypophosphorous acid | After heating treatment | 10000 | DHT-6 | After addition of additive 2 | 0.3 |
| Example 2-20 | Production Example 2-2 | EDTMP•5Na | Polymerization | 200 | Malic acid | After heating treatment | 5000 | DHT-6 | After addition of additive 2 | 0.3 |
| Example 2-21 | Production Example 2-2 | EDTMP•5Na | Polymerization | 200 | Malic acid | After heating treatment | 15000 | DHT-6 | After addition of additive 2 | 0.3 |
| Example 2-22 | Production Example 2-3 | EDTMP•5Na | Polymerization | 500 | — | — | — | DHT-6 | After heating treatment | 0.3 |
| Example 2-23 | Production Example 2-5 | DTPA•3Na | Polymerization | 1000 | — | — | — | DHT-6 | After heating treatment | 0.3 |
| Example 2-24 | Production Example 2-1 | DTPA•3Na | Polymerization | 50 | DTPA•3Na | After heating treatment | 950 | DHT-6 | After addition of additive 2 | 0.3 |
| Example 2-25 | Production Example 2-4 | EDTMP•5Na | Polymerization | 1000 | — | — | — | DHT-6 | After heating treatment | 0.3 |
| Example 2-26 | Production Example 2-2 | EDTMP•5Na | Polymerization | 200 | EDTMP•5Na | After heating treatment | 800 | DHT-6 | After addition of additive 2 | 0.3 |
| Comparative Example 2-5 | Production Example 2-2 | EDTMP•5Na | Polymerization | 200 | — | — | — | AEROSIL | After heating treatment | 0.3 |
| Comparative Example 2-6 | Production Example 2-2 | EDTMP•5Na | Polymerization | 200 | — | — | — | Mg hydroxide | After heating treatment | 0.3 |

Table 2-1 is a list of production conditions.

TABLE 2-2

| | Water absorbent resin | Additive 1 Kind | Additive 1 Amount of addition ppm | Additive 2 Kind | Additive 2 Amount of addition ppm | Additive 3 Kind | Additive 3 Amount of addition, mass % | CRC g/g | AAp g/g | Blocking ratio, mass % | Y1 | Amount of dust mg/kg |
|---|---|---|---|---|---|---|---|---|---|---|---|---|
| Comparative Example 2-1 | Comparative Example 2-1 | — | — | — | — | — | — | 42 | 20 | 100 | 36 | |
| Comparative Example 2-2 | Comparative Example 2-1 | — | — | — | — | — | — | 43 | 29 | 100 | 35 | |
| Comparative Example 2-3 | Production Example 2-1 | DTPA•3Na | 50 | DTPA•3Na | 100 | — | — | 38.0 | 31.0 | 100 | 28.8 | |

TABLE 2-2-continued

| | Water absorbent resin | Additive 1 Kind | Additive 1 Amount of addition ppm | Additive 2 Kind | Additive 2 Amount of addition ppm | Additive 3 Kind | Additive 3 Amount of addition, mass % | CRC g/g | AAp g/g | Blocking ratio, mass % | Y1 | Amount of dust mg/kg |
|---|---|---|---|---|---|---|---|---|---|---|---|---|
| Comparative Example 2-4 | Production Example 2-1 | DTPA•3Na | 50 | DTPA•3Na | 100 | — | — | 40.0 | 28.0 | 100 | 27.2 | |
| Example 2-1 | Production Example 2-1 | DTPA•3Na | 50 | DTPA•3Na | 100 | DHT-6 | 0.3 | 38.0 | 31.0 | 0 | 30.9 | |
| Example 2-2 | Production Example 2-1 | DTPA•3Na | 50 | NaH2PO4 | 15000 | DHT-6 | 0.3 | 37.4 | 30.4 | 0 | 31.5 | |
| Example 2-3 | Production Example 2-2 | EDTMP•5Na | 200 | — | — | DHT-6 | 0.3 | 37.6 | 30.9 | 0 | 27.2 | 26 |
| Example 2-4 | Production Example 2-2 | EDTMP•5Na | 200 | — | — | DHT-4H | 0.3 | 37.6 | 30.3 | 0 | 26.2 | 31 |
| Example 2-5 | Production Example 2-2 | EDTMP•5Na | 200 | — | — | HT-1-NC | 0.3 | 37.6 | 30.6 | 0 | 24.8 | 35 |
| Example 2-6 | Production Example 2-1 | DTPA•3Na | 50 | DTPA•3Na + SBS | 300 + 5000 | DHT-6 | 0.3 | 38.0 | 31.0 | 0 | 19 | |
| Example 2-7 | Production Example 2-2 | EDTMP•5Na | 200 | NaH2PO4 | 4400 | DHT-6 | 0.3 | 37.5 | 31.0 | 0 | 22.7 | |
| Example 2-8 | Production Example 2-2 | EDTMP•5Na | 200 | NaH2PO4 | 4400 | DHT-6 | 0.5 | 37.3 | 30.8 | 0 | 22.9 | |
| Example 2-9 | Production Example 2-2 | EDTMP•5Na | 200 | NaH2PO4 | 10000 | DHT-6 | 0.3 | 37.4 | 30.4 | 0 | 21.5 | |
| Example 2-10 | Production Example 2-2 | EDTMP•5Na | 200 | NaH2PO4 | 5000 | DHT-6 | 0.3 | 37.7 | 30.8 | 0 | 21.2 | |
| Example 2-11 | Production Example 2-2 | EDTMP•5Na | 200 | Na3PO4 | 5000 | DHT-6 | 0.3 | 38.0 | 30.8 | 0 | 23 | |
| Example 2-12 | Production Example 2-2 | EDTMP•5Na | 200 | Tripolyphosphoric acid | 5000 | DHT-6 | 0.3 | 40.1 | 28.1 | 0 | 22.2 | |
| Example 2-13 | Production Example 2-2 | EDTMP•5Na | 200 | Hexametaphosphoric acid | 5000 | DHT-6 | 0.3 | 39.6 | 28.6 | 0 | 22 | |
| Example 2-14 | Production Example 2-2 | EDTMP•5Na | 200 | SBS | 1000 | DHT-6 | 0.3 | 38.0 | 30.9 | 0 | 17.3 | |
| Example 2-15 | Production Example 2-2 | EDTMP•5Na | 200 | SBS | 10000 | DHT-6 | 0.3 | 37.8 | 31.0 | 0 | 20.4 | |
| Example 2-16 | Production Example 2-2 | EDTMP•5Na | 200 | 2-Hydroxy-2-sulfinatoacetic acid•2Na | 500 | DHT-6 | 0.3 | 38.1 | 30.8 | 0 | 14.3 | |
| Example 2-17 | Production Example 2-2 | EDTMP•5Na | 200 | 2-Hydroxy-2-sulfinatoacetic acid•2Na | 5000 | DHT-6 | 0.3 | 37.9 | 30.6 | 0 | 15.9 | |
| Example 2-18 | Production Example 2-2 | EDTMP•5Na | 200 | Hypophosphorous acid | 2000 | DHT-6 | 0.3 | 39.9 | 28.3 | 0 | 21.8 | |
| Example 2-19 | Production Example 2-2 | EDTMP•5Na | 200 | Hypophosphorous acid | 10000 | DHT-6 | 0.3 | 39.6 | 28.4 | 0 | 16 | |
| Example 2-20 | Production Example 2-2 | EDTMP•5Na | 200 | Malic acid | 5000 | DHT-6 | 0.3 | 37.8 | 30.5 | 3 | 20 | |
| Example 2-21 | Production Example 2-2 | EDTMP•5Na | 200 | Malic acid | 15000 | DHT-6 | 0.3 | 37.7 | 30.1 | 7 | 19.9 | |
| Example 2-22 | Production Example 2-3 | EDTMP•5Na | 500 | — | — | DHT-6 | 0.3 | 38.1 | 31 | 0 | 23 | |
| Example 2-23 | Production Example 2-5 | DTPA•3Na | 1000 | — | — | DHT-6 | 0.3 | 38 | 31 | 0 | 27.5 | |
| Example 2-24 | Production Example 2-1 | DTPA•3Na | 50 | DTPA•3Na | 950 | DHT-6 | 0.3 | 37.6 | 30.7 | 0 | 27.2 | |
| Example 2-25 | Production Example 2-4 | EDTMP•5Na | 1000 | — | — | DHT-6 | 0.3 | 37.6 | 30.6 | 0 | 20.3 | |
| Example 2-26 | Production Example 2-2 | EDTMP•5Na | 200 | EDTMP•5Na | 800 | DHT-6 | 0.3 | 37.2 | 30.1 | 0 | 22 | |
| Comparative Example 2-5 | Production Example 2-2 | EDTMP•5Na | 200 | — | — | AEROSIL | 0.3 | 37.2 | 26.3 | 0 | 21 | |
| Comparative Example 2-6 | Production Example 2-2 | EDTMP•5Na | 200 | — | — | Mg hydroxide | 0.3 | 37.4 | 30.2 | 99 | 39 | |

(Summary of Table 2-2)

As shown in the above tables, the water absorbing agents of the present invention have low blocking ratio against moisture absorptions. Furthermore, it is understood that coloration with the lapse of time is suppressed by adding a chelating agent.

Production Example 3-1

In 5500 g of an aqueous solution of sodium acrylate having the neutralization rate of 75% by mole (monomer concentration: 35% by mass), 0.38 g of trimethylolpropane triacrylate (molecular weight 296) (0.006% by mole relative to the monomer) was dissolved, and a monomer aqueous solution (a) was prepared. Subsequently, the monomer aqueous solution was degassed for 30 minutes in a nitrogen gas atmosphere.

Next, the monomer aqueous solution (a) was introduced into a reactor produced by providing a lid to a double blade type jacketed kneader made of stainless steel with an internal capacity of 10 L and having two sigma-shaped blades. Nitrogen gas was blown into the reactor while the liquid temperature was maintained at 30° C., and the reactor was purged with nitrogen such that the dissolved oxygen in the system would be 1 ppm or less.

Subsequently, 24.6 g of a 10 mass % aqueous solution of sodium persulfate and 21.8 g of a 0.2 mass % aqueous solution of L-ascorbic acid were separately added to the monomer aqueous solution (a) with stirring, and polymerization was initiated after about 1 minute. While the produced water-containing gel-like cross-linked polymer (a) was crushed, polymerization was performed at 30° C. to 90° C., and when 60 minutes had passed from the initiation of polymerization, a water-containing gel-like cross-linked polymer (a) was taken out from the reactor. The water-containing gel-like cross-linked polymer (a) thus obtained was subjected to grain refining to particles having a diameter of about 5 mm.

The water-containing gel-like cross-linked polymer (a) thus subjected to grain refining described above was spread on a wire gauze having a mesh size of 300 μm (50-mesh) and dried under hot air for 45 minutes at 180° C. Subsequently, the cross-linked polymer was pulverized with a roll mill, and was classified with JIS standard sieves having mesh sizes of 850 μm and 150 μm. Through this series of operations, a water absorbent resin powder (a), which was a water absorbent resin (solid content 4.0% by mass) in an irregularly shaped crushed form, was obtained. The CRC (water absorption capacity without load) of the water absorbent resin powder (a) was 56.0 [g/g].

Next, the water absorbent resin powder (a) was transferred into a rotary mixer manufactured by Deutsche Lödige GmbH, and an aqueous solution of surface cross-linking agent including 0.025 parts by mass of ethylene glycol diglycidyl ether (trade name: DENACOL EX-810 manufactured by Nagase ChemteX Corp.), 0.3 parts by mass of ethylene carbonate, 0.5 parts by mass of 1,2-propanediol (melting point−59° C.), and 3.0 parts by mass of water, was uniformly mixed relative to 100 parts by mass of the water absorbent resin powder (a). The mixture was heat treated for 40 minutes at 175° C. Thereafter, the mixture was passed through a JIS standard sieve having a mesh size of 850 μm, and thereby water absorbent resin particles (surface cross-linked water absorbent resin) (a-1) were obtained. The water absorbent resin particles (a-1) were irregularly shaped, and 95% by mass or more of the particles were included in the range of 150 μm or more but less than 850 μm.

Production Example 3-2

In polypropylene containers having an inner diameter of 80 mm and a capacity of 1 liter and covered with expanded polystyrene, which is a thermal insulating material, a solution (A) in which 291 g of acrylic acid, 0.43 g (0.02% by mole relative to the carboxyl group-containing unsaturated monomer) of polyethylene glycol diacrylate (molecular weight 523) as an internal cross-linking agent, and 3.60 g of an acrylic acid solution prepared by dissolving IRGACURE (registered trademark) 184 in acrylic acid at 1.0% by mass were mixed, and a solution (B) in which 247 g of a 48.5 mass % aqueous solution of sodium hydroxide and 255 g of ion-exchanged water adjusted to 50° C. were mixed, were prepared. A monomer aqueous solution (C) was obtained by rapidly adding the solution (B) to the solution (A), which was being stirred at 800 rpm using a magnetic stirrer having a length of 5 cm, and mixing the solutions. The liquid temperature of the monomer aqueous solution (C) was increased to about 100° C. due to the heat of neutralization and the heat of dissolution. The neutralization rate of acrylic acid was 73.5% by mole.

Next, 1.8 g of a 3 mass % aqueous solution of sodium persulfate was added to the monomer aqueous solution (C), and the mixture was stirred for about 1 second, and then the mixture was poured immediately into a vat type container made of stainless steel and lined with TEFLON (registered trademark) on the inner surface, in an open system. Furthermore, ultraviolet was irradiated simultaneously with pouring of the monomer aqueous solution into the vat type container made of stainless steel.

As soon as the monomer aqueous solution was poured into the vat, polymerization was initiated (temperature at the time of initiation of polymerization 98° C.), and polymerization reached the peak temperature within about 1 minute. After 3 minutes, irradiation of ultraviolet was terminated, and a hydrous polymerization product was taken out. This series of operations were carried out in an open system in air.

An obtained hydrous polymerization product was crushed by a meat chopper (meat-chopper type: 12VR-400KSOX, Iizuka Kogyo, Inc., die orifice diameter: 7.5 mm, number of holes: 38, die thickness 8 mm), and subjected to grain refining, crushed hydrous polymer particles were obtained (mass average particle size 1000 μm).

These subjected to grain refining, crushed hydrous polymer particles were spread on a 50-mesh (mesh size 300 μm) wire gauze, and were subjected to hot air drying at 180° C. The dried product was pulverized with a roll mill, and the particles were classified with JIS standard sieves having a mesh size of 850 μm and a mesh size of 150 μm. Thereby, a water absorbent resin powder (b), which was a water absorbent resin (solid content 96% by mass) in an irregularly shaped crushed form, was obtained. The CRC (water absorption capacity without load) of the water absorbent resin powder (b) was 52.0 [g/g].

Next, the water absorbent resin powder (b) described above was transferred to a rotary mixer manufactured by Deutsche Lödige GmbH, and an aqueous solution of surface cross-linking agent including 0.025 parts by mass of ethylene glycol diglycidyl ether, 1.5 parts by mass of propylene glycol, and 3.5 parts by mass of water, was uniformly mixed relative to 100 parts by mass of the water absorbent resin powder (b). The mixture was heat treated for 45 minutes at 100° C. Thereafter, the particles size of the water absorbent resin powder was adjusted using a JIS standard sieve having a mesh size of 850 μm, and thereby water absorbent resin particles (b-1) having the surface cross-linked were obtained. The water absorbent resin particles (b-1) were irregularly shaped, and 95% by mass or more of the particles were included in the range of 150 μm or more but less than 850 μm.

Production Example 3-3

Water absorbent resin particles (c-1) having the surface cross-linked were obtained by performing the same treatment as in Production Example 3-1, except that at the time of preparing the monomer aqueous solution (a) in Production Example 3-1, 0.61 g of 0.45 wt % sodium diethylenetriaminepentaacetate (abbreviation: DTPA.3Na, CHELEST PC-45; manufactured by Chelest Corp.) was added to the monomer aqueous solution (a), and polymerization was carried out. The water absorbent resin particles (c-1) were irregularly shaped, and 95% by mass or more of the particles were included in the range of 150 μm or more but less than 850 μm.

Production Example 3-4

Water absorbent resin particles (d-1) having the surface cross-linked were obtained by performing the same treatment as in Production Example 3-2, except that at the time of preparing the monomer aqueous solution (a) in Production Example 3-2, 0.61 g of 0.45 wt % sodium diethylenetriaminepentaacetate (abbreviation: DTPA.3Na, CHELEST PC-45; manufactured by Chelest Corp.) was added to the monomer aqueous solution (a), and polymerization was carried out. The water absorbent resin particles (d-1) were irregularly shaped, and 95% by mass or more of the particles were included in the range of 150 μm or more but less than 850 μm.

Production Example 3-5

Water absorbent resin particles (e-1) having the surface cross-linked were obtained by performing the same treatment as in Production Example 3-1, except that at the time of preparing the monomer aqueous solution (a) in Production Example 3-1, 3.6 g of pentasodium N,N,N',N'-ethylenediaminetetrakismethylenephosphonate (abbreviation: EDTMP.5Na, DEQUEST (registered trademark) 2046; Italmatch Chemicals S.p.A. (31% aqueous solution) diluted) was added to the monomer aqueous solution (a), and polymerization was carried out. The water absorbent resin particles (e-1) were irregularly shaped, and 95% by mass or more of the particles were included in the range of 150 μm or more but less than 850 μm.

Production Example 3-6

Water absorbent resin particles (f-1) having the surface cross-linked were obtained by performing the same treatment as in Production Example 3-2, except that at the time of preparing the monomer aqueous solution (a) in Production Example 3-2, 3.6 g of pentasodium N,N,N',N'-ethylenediaminetetrakismethylenephosphonate (abbreviation: EDTMP.5Na, DEQUEST (registered trademark) 2046; Italmatch Chemicals S.p.A. (31% aqueous solution) diluted) was added to the monomer aqueous solution (a), and polymerization was carried out. The water absorbent resin particles (f-1) were irregularly shaped, and 95% by mass or more of the particles were included in the range of 150 μm or more but less than 850 μm.

Production Example 3-7

Water absorbent resin particles (g-1) having the surface cross-linked were obtained by performing the same treatment as in Production Example 3-2, except that at the time of preparing the monomer aqueous solution (a) in Production Example 3-2, 8.9 g of pentasodium N,N,N',N'-ethylenediaminetetrakismethylenephosphonate (abbreviation: EDTMP.5Na, DEQUEST (registered trademark) 2046; Italmatch Chemicals S.p.A. (31% aqueous solution) diluted) was added to the monomer aqueous solution (a), and polymerization was carried out. The water absorbent resin particles (g-1) were irregularly shaped, and 95% by mass or more of the particles were included in the range of 150 μm or more but less than 850 μm.

Production Example 3-8

Water absorbent resin particles (h-1) having the surface cross-linked were obtained by performing the same treatment as in Production Example 3-2, except that at the time of preparing the monomer aqueous solution (a) in Production Example 3-2, 12.2 g of 0.45 wt % sodium diethylenetriaminepentaacetate (abbreviation: DTPA.3Na, CHELEST PC-45; manufactured by Chelest Corp.) was added to the monomer aqueous solution (a), and polymerization was carried out. The water absorbent resin particles (h-1) were irregularly shaped, and 95% by mass or more of the particles were included in the range of 150 μm or more but less than 850 μm.

Production Example 3-9

Water absorbent resin particles (i-1) having the surface cross-linked were obtained by performing the same treatment as in Production Example 3-2, except that at the time of preparing the monomer aqueous solution (a) in Production Example 3-2, 18.0 g of pentasodium N,N,N',N'-ethylenediaminetetrakismethylenephosphonate (abbreviation: EDTMP.5Na, DEQUEST (registered trademark) 2046; Italmatch Chemicals S.p.A. (31% aqueous solution) diluted) was added to the monomer aqueous solution (a), and polymerization was carried out. The water absorbent resin particles (i-1) were irregularly shaped, and 95% by mass or more of the particles were included in the range of 150 μm or more but less than 850 μm.

Comparative Example 3-1

The water absorbent resin particles (b-1) described in Production Example 3-2 are designated as comparative water absorbent resin particles (water absorbing agent) (1), and various physical properties thereof are presented in Table 3-2.

Comparative Example 3-2

The water absorbent resin particles (a-1) described in Production Example 3-1 are designated as comparative water absorbent resin particles (water absorbing agent) (2), and various physical properties thereof are presented in Table 3-2.

Comparative Example 3-3

The water absorbent resin particles (d-1) described in Production Example 3-4 are designated as comparative water absorbent resin (water absorbing agent) (3), and various physical properties thereof are presented in Table 3-2.

Example 3-1

A mixed liquid including 0.01 parts by mass of DTPA.3Na and 1 part by mass of water, was uniformly mixed relative to 100 parts by mass of the water absorbent resin particles (c-1) described in Production Example 3-3. The mixture was granulated and then heat treated for 45 minutes at 60° C. Thereafter, the particle size of the water absorbent resin particles was adjusted using a JIS standard sieve having a mesh size of 850 μm, and thereby granulated water absorbent resin particles were obtained.

0.3 parts by weight of hydrotalcite (product name: DHT-6, manufactured by Kyowa Chemical Industry Co., Ltd., $Mg_6Al_2(OH)_{16}CO_3.4H_2O$ [in general formula (1), x=0.25, m=0.50], volume average particle size 0.5 μm) was mixed relative to 100 parts by mass of the granulated water absorbent resin particles (surface cross-linked water absorbent resin) described above. Regarding the mixing, 30 g of the water absorbent resin was introduced into a mayonnaise bottle having a capacity of 225 mL together with hydrotalcite, and the content was mixed for 3 minutes by vibration of a paint shaker (manufactured by Toyo Seiki Seisakusho Co., Ltd.). Thus, a water absorbent resin (3-1) was obtained. The performance of the water absorbent resin (3-1) is presented in Table 3-2.

Example 3-2

A mixed liquid including 0.01 parts by mass of DTPA.3Na and 1 part by mass of water, was uniformly mixed relative to 100 parts by mass of the water absorbent resin particles (d-1) described in Production Example 3-4. The mixture was granulated and then heat treated for 45 minutes at 60° C. Thereafter, the particle size of the water absorbent resin particles was adjusted using a JIS standard sieve having a mesh size of 850 μm, and thereby granulated water absorbent resin particles were obtained.

0.3 parts by weight of hydrotalcite (product name: DHT-6, manufactured by Kyowa Chemical Industry Co., Ltd., $Mg_6Al_2(OH)_{16}CO_3.4H_2O$ [in general formula (1), x=0.25, m=0.50], volume average particle size 0.5 μm) were mixed relative to 100 parts by mass of the granulated water absorbent resin particles (surface cross-linked water absorbent resin) described above. Regarding the mixing, 30 g of the water absorbent resin was introduced into a mayonnaise bottle having a capacity of 225 mL together with hydrotalcite, and the content was mixed for 3 minutes by vibration of a paint shaker (manufactured by Toyo Seiki Seisakusho Co., Ltd.). Thus, a water absorbent resin (3-2) was obtained. The performance of the water absorbent resin (3-2) is presented in Table 3-2.

Example 3-3

A water absorbent resin (3-3) was obtained in the same manner as in Example 3-2, except that 100 parts by mass of the water absorbent resin particles having the surface cross-linked, which were used in Example 3-2, were uniformly mixed with a mixed liquid including 0.03 parts by mass of DTPA.3Na and 1 part by mass of water. The performance of the water absorbent resin (3-3) is presented in Table 3-2.

Example 3-4

A water absorbent resin (3-4) was obtained in the same manner as in Example 3-1, except that 0.3 parts by mass of SBS (sodium hydrogen sulfite) was added in addition to 0.01 parts by mass of DTPA.3Na and 1 part by mass of water used in Example 3-1. The performance of the water absorbent resin (3-4) is presented in Table 3-2.

Example 3-5

A water absorbent resin (3-5) was obtained in the same manner as in Example 3-3, except that 0.03 parts by mass of DTPA.3Na used in Example 3-3 was replaced with 0.022 parts by mass of EDTMP. The performance of the water absorbent resin (3-5) is presented in Table 3-2.

Example 3-6

0.3 parts by weight of hydrotalcite (product name: DHT-6, manufactured by Kyowa Chemical Industry Co., Ltd., $Mg_6Al_2(OH)_{16}CO_3.4H_2O$ [in general formula (1), x=0.25, m=0.50], volume average particle size 0.5 μm) were mixed relative to 100 parts by mass of the water absorbent resin (f-1) described in Production Example 3-6. Regarding the mixing, 30 g of the water absorbent resin was introduced into a mayonnaise bottle having a capacity of 225 mL together with hydrotalcite, and the content was mixed for 3 minutes by vibration of a paint shaker (manufactured by Toyo Seiki Seisakusho Co., Ltd.). Thus, a water absorbent resin (3-6) was obtained. The performance of the water absorbent resin (3-6) is presented in Table 3-2.

Example 3-7

0.3 parts by weight of hydrotalcite (product name: DHT-6, manufactured by Kyowa Chemical Industry Co., Ltd., $Mg_6Al_2(OH)_{16}CO_3.4H_2O$ [in general formula (1), x=0.25, m=0.50], volume average particle size 0.5 μm) were mixed relative to 100 parts by mass of the water absorbent resin (g-1) described in Production Example 3-7. Regarding the mixing, 30 g of the water absorbent resin was introduced into a mayonnaise bottle having a capacity of 225 mL together with hydrotalcite, and the content was mixed for 3 minutes by vibration of a paint shaker (manufactured by Toyo Seiki Seisakusho Co., Ltd.). Thus, a water absorbent resin (3-7) was obtained. The performance of the water absorbent resin (3-7) is presented in Table 3-2.

Comparative Example 3-4

The water absorbent resin particles (f-1) described in Production Example 3-6 are designated as comparative water absorbent resin particles (3-4), and the performance thereof is presented in Table 3-2.

Comparative Example 3-5

0.3 parts by mass of silica (product name: AEROSIL 200CF, manufactured by Nippon Aerosil Co., Ltd.) were mixed in the same manner as in Example 3-6, relative to 100 parts by mass of the comparative water absorbent resin particles (3-4) (surface cross-linked water absorbent resin), and comparative water absorbent resin particles (3-5) were obtained. The performance of the comparative water absorbent resin particles (3-5) is presented in Table 3-2.

Comparative Example 3-6

0.3 parts by mass of silica (product name: AEROSIL 200CF, manufactured by Nippon Aerosil Co., Ltd.) were mixed in the same manner as in Example 3-6, relative to 100 parts by mass of the water absorbent resin (e-1) described in Production Example 3-5, and comparative water absorbent resin particles (3-6) were obtained. The performance of the comparative water absorbent resin particles (3-6) is presented in Table 3-2.

Example 3-8

A mixed liquid including 0.01 parts by mass of DTPA.3Na and 1 part by mass of water, was uniformly mixed relative to 100 parts by mass of the water absorbent resin (e-1) described in Production Example 3-5. The mixture was granulated and then heat treated for 45 minutes at 60° C. Thereafter, the particle size of the water absorbent resin was adjusted using a JIS standard sieve having a mesh size of 850 μm, and thereby granulated water absorbent resin particles were obtained.

0.3 parts by weight of hydrotalcite (product name: DHT-6, manufactured by Kyowa Chemical Industry Co., Ltd., $Mg_6Al_2$ $(OH)_{15}CO_3.4H_2O$ [in general formula (1), x=0.25, m=0.50], volume average particle size 0.5 μm) were mixed relative to 100 parts by mass of the granulated water absorbent resin particles (surface cross-linked water absorbent resin) described above. Regarding the mixing, 30 g of the water absorbent resin was introduced into a mayonnaise bottle having a capacity of 225 mL together with hydrotalcite, and the content was mixed for 3 minutes by vibration of a paint shaker (manufactured by Toyo Seiki Seisakusho Co., Ltd.). Thus, a water absorbent resin (3-8) was obtained. The performance of the water absorbent resin (3-8) is presented in Table 3-2.

Example 3-9

A mixed liquid including 0.01 parts by mass of DTPA.3Na and 1 part by mass of water, was uniformly mixed relative to 100 parts by mass of the water absorbent resin (g-1) described in Production Example 3-7. The mixture was granulated and then heat treated for 45 minutes at 60° C. Thereafter, the particle size of the water absorbent resin was adjusted using a JIS standard sieve having a mesh size of 850 μm, and thereby granulated water absorbent resin particles were obtained.

0.3 parts by weight of hydrotalcite (product name: DHT-6, manufactured by Kyowa Chemical Industry Co. Ltd., $Mg_6Al_2$ $(OH)_{16}CO_3.4H_2O$ [in general formula (1), x=0.25, m=0.50], volume average particle size 0.5 μm) were mixed relative to 100 parts by mass of the granulated water absorbent resin particles (surface cross-linked water absorbent resin) described above. Regarding the mixing, 30 g of the water absorbent resin was introduced into a mayonnaise bottle having a capacity of 225 mL together with hydrotalcite, and the content was mixed for 3 minutes by vibration of a paint shaker (manufactured by Toyo Seiki Seisakusho Co., Ltd.). Thus, a water absorbent resin (3-9) was obtained. The performance of the water absorbent resin (3-9) is presented in Table 3-2.

Example 3-10

A mixed liquid including 0.03 parts by mass of DTPA.3Na, 0.440 parts by mass of sodium dihydrogen phosphate, and 3.0 parts by mass of water, was uniformly mixed relative to 100 parts by mass of the comparative water absorbent resin particles (3-4) (surface cross-linked water absorbent resin). The mixture was granulated and then heat treated for 45 minutes at 60° C. Thereafter, the particle size of the water absorbent resin particles was adjusted using a JIS standard sieve having a mesh size of 850 μm, and thereby granulated water absorbent resin particles were obtained.

0.3 parts by weight of hydrotalcite (product name: DHT-6, manufactured by Kyowa Chemical Industry Co., Ltd., $Mg_6Al_2$ $(OH)_{16}CO_3.4H_2O$ [in general formula (1), x=0.25, m=0.50], volume average particle size 0.5 μm) were mixed relative to 100 parts by mass of the granulated water absorbent resin particles (surface cross-linked water absorbent resin) described above. Regarding the mixing, 30 g of the water absorbent resin was introduced into a mayonnaise bottle having a capacity of 225 mL together with hydrotalcite, and the content was mixed for 3 minutes by vibration of a paint shaker (manufactured by Toyo Seiki Seisakusho Co., Ltd.). Thus, a water absorbent resin (3-10) was obtained. The performance of the water absorbent resin (3-10) is presented in Table 3-2.

Example 3-11

A water absorbent resin (3-11) was obtained by the same operation as that used in Example 3-10, except that 0.03 parts by mass of DTPA.3Na and 0.440 parts by mass of sodium dihydrogen phosphate used in Example 3-10 were changed to 0.5 parts by mass of sodium bisulfite. The performance of the water absorbent resin (3-11) is presented in Table 3-2.

Example 3-12

0.3 parts by weight of hydrotalcite (product name: DHT-6, manufactured by Kyowa Chemical Industry Co., Ltd., $Mg_6Al_2$ $(OH)_{16}CO_3.4H_2O$ [in general formula (1) x=0.25, m=0.50], volume average particle size 0.5 μm) were mixed relative to 100 parts by mass of the water absorbent resin (h-1) described in Production Example 3-8. Regarding the mixing, 30 g of the water absorbent resin was introduced into a mayonnaise bottle having a capacity of 225 mL together with hydrotalcite, and the content was mixed for 3 minutes by vibration of a paint shaker (manufactured by Toyo Seiki Seisakusho Co., Ltd.). Thus, a water absorbent resin (3-12) was obtained. The performance of the water absorbent resin (3-12) is presented in Table 3-2.

Example 3-13

A mixed liquid including 0.1 parts by mass of DTPA.3Na and 1 part by mass of water, was uniformly mixed relative to 100 parts by mass of the water absorbent resin (a-1) described in Production Example 3-2. The mixture was granulated and then heat treated for 45 minutes at 60° C. Thereafter, the particle size of the water absorbent resin was adjusted using a JIS standard sieve having a mesh size of 850 μm, and thereby granulated water absorbent resin particles were obtained.

0.3 parts by weight of hydrotalcite (product name: DHT-6, manufactured by Kyowa Chemical Industry Co., Ltd., $Mg_6Al_2$ $(OH)_{16}CO_3.4H_2O$ [in general formula (1), x=0.25, m=0.50], volume average particle size 0.5 μm) were mixed relative to 100 parts by mass of the granulated water absorbent resin particles (surface crosslinked water absorbent resin) described above. Regarding the mixing, 30 g of the water absorbent resin was introduced into a mayonnaise bottle having a capacity of 225 mL together with hydrotalcite, and the content was mixed for 3 minutes by vibration of a paint shaker (manufactured by Toyo Seiki Seisakusho Co., Ltd.). Thus, a water absorbent resin (3-13) was obtained. The performance of the water absorbent resin (3-13) is presented in Table 3-2.

Example 3-14

0.3 parts by weight of hydrotalcite (product name: DHT-6, manufactured by Kyowa Chemical Industry Co., Ltd., $Mg_6Al_2$ $(OH)_{16}CO_3.4H_2O$ [in general formula (1), x=0.25, m=0.50], volume average particle size 0.5 μm) were mixed relative to 100 parts by mass of the water absorbent resin (i-1) described in Production Example 3-9. Regarding the mixing, 30 g of the water absorbent resin was introduced into a mayonnaise bottle having a capacity of 225 mL together with hydrotalcite, and the content was mixed for 3 minutes by vibration of a paint shaker (manufactured by Toyo Seiki Seisakusho Co., Ltd.). Thus, a water absorbent resin (3-14) was obtained. The performance of the water absorbent resin (3-14) is presented in Table 3-2.

Example 3-15

A water absorbent resin (3-15) was obtained in the same manner as in Example 3-8, except that 0.01 parts by mass of DTPA.3Na used in Example 3-6 was replaced with 0.08 parts by mass of EDTMP.5Na. The performance of the water absorbent resin (3-15) is presented in Table 3-2.

Example 3-16

A water absorbent resin (3-16) was obtained in the same manner as in Example 3-8, except that the amount of DTPA.3Na used in Example 3-6 was changed from 0.01 parts by mass to 0.03 parts by mass. The performance of the water absorbent resin (3-16) is presented in Table 3-2.

Example 3-17

A mixed liquid including 0.1 parts by mass of DTPA.3Na and 1 part by mass of water, was uniformly mixed relative to 100 parts by mass of the water absorbent resin (i-1) described in Production Example 3-9. The mixture was granulated and then heat treated for 45 minutes at 60° C. Thereafter, the particle size of the water absorbent resin was adjusted using a JIS standard sieve having a mesh size of 850 μm, and thereby granulated water absorbent resin particles were obtained.

0.3 parts by weight of hydrotalcite (product name: DHT-6, manufactured by Kyowa Chemical Industry Co., Ltd., $Mg_6Al_2(OH)_{16}CO_3.4H_2O$ [in general formula (1), x=0.25, m=0.50], volume average particle size 0.5 μm) were mixed relative to 100 parts by mass of the granulated water absorbent resin particles (surface crosslinked water absorbent resin) described above. Regarding the mixing, 30 g of the water absorbent resin was introduced into a mayonnaise bottle having a capacity of 225 mL together with hydrotalcite, and the content was mixed for 3 minutes by vibration of a paint shaker (manufactured by Toyo Seiki Seisakusho Co., Ltd.). Thus, a water absorbent resin (3-17) was obtained. The performance of the water absorbent resin (3-17) is presented in Table 3-2.

TABLE 3-1

| | | Additive 1 | | | Additive 2 | | | Additive 3 | | |
|---|---|---|---|---|---|---|---|---|---|---|
| | Water absorbent resin | Kind | Time point of addition | Amount of addition ppm | Kind | Time point of addition | Amount of addition ppm | Kind | Time point of addition | Amount of addition, mass % |
| Comparative Example 3-1 | Production Example 3-2 | — | — | — | — | | — | — | — | — |
| Comparative Example 3-2 | Production Example 3-1 | — | — | — | — | | — | — | — | — |
| Comparative Example 3-3 | Production Example 3-4 | DTPA•3Na | Polymerization | 50 | — | | — | — | — | — |
| Example 3-1 | Production Example 3-3 | DTPA•3Na | Polymerization | 50 | DTPA•3Na | After heating treatment | 100 | DHT-6 | After addition of additive 2 | 0.3 |
| Example 3-2 | Production Example 3-4 | DTPA•3Na | Polymerization | 50 | DTPA•3Na | After heating treatment | 100 | DHT-6 | After addition of additive 2 | 0.3 |
| Example 3-3 | Production Example 3-4 | DTPA•3Na | Polymerization | 50 | DTPA•3Na | After heating treatment | 300 | DHT-6 | After addition of additive 2 | 0.3 |
| Example 3-4 | Production Example 3-3 | DTPA•3Na | Polymerization | 50 | DTPA•3Na + SBS | After heating treatment | 50 + 3000 | DHT-6 | After addition of additive 2 | 0.3 |
| Example 3-5 | Production Example 3-4 | DTPA•3Na | Polymerization | 50 | EDTMP•5Na | At the time of heating treatment | 220 | DHT-6 | After heating treatment | 0.3 |
| Example 3-6 | Production Example 3-6 | EDTMP•5Na | Polymerization | 200 | — | — | — | DHT-6 | After heating treatment | 0.3 |
| Example 3-7 | Production Example 3-7 | EDTMP•5Na | Polymerization | 500 | — | — | — | DHT-6 | After heating treatment | 0.3 |
| Comparative Example 3-4 | Production Example 3-6 | EDTMP•5Na | Polymerization | 200 | — | — | — | — | — | — |
| Comparative Example 3-5 | Production Example 3-6 | EDTMP•5Na | Polymerization | 200 | — | — | — | AEROSIL | After heating treatment | 0.3 |
| Comparative Example 3-6 | Production Example 3-5 | EDTMP•5Na | Polymerization | 200 | — | — | — | AEROSIL | After heating treatment | 0.3 |
| Example 3-8 | Production Example 3-5 | EDTMP•5Na | Polymerization | 200 | DTPA•3Na | After heating treatment | 100 | DHT-6 | After addition of additive 2 | 0.3 |
| Example 3-9 | Production Example 3-7 | EDTMP•5Na | Polymerization | 500 | DTPA•3Na | After heating treatment | 100 | DHT-6 | After addition of additive 2 | 0.3 |
| Example 3-10 | Production Example 3-6 | EDTMP•5Na | Polymerization | 200 | DTPA•3Na + $NaH_2PO_4$ | After heating treatment | 300 + 4400 | DHT-6 | After addition of additive 2 | 0.3 |
| Example 3-11 | Production Example 3-6 | EDTMP•5Na | Polymerization | 200 | SBS | After heating treatment | 5000 | DHT-6 | After addition of additive 2 | 0.3 |
| Example 3-12 | Production Example 3-8 | DTPA•3Na | Polymerization | 1000 | — | — | — | DHT-6 | After heating treatment | 0.3 |
| Example 3-13 | Production Example 3-2 | — | — | — | DTPA•3Na | After heating treatment | 1000 | DHT-6 | After addition of additive 2 | 0.3 |
| Example 3-14 | Production Example 3-9 | EDTMP•5Na | Polymerization | 1000 | — | — | — | DHT-6 | After heating treatment | 0.3 |

TABLE 3-1-continued

| | Water absorbent resin | Additive 1 Kind | Additive 1 Time point of addition | Additive 1 Amount of addition ppm | Additive 2 Kind | Additive 2 Time point of addition | Additive 2 Amount of addition ppm | Additive 3 Kind | Additive 3 Time point of addition | Additive 3 Amount of addition, mass % |
|---|---|---|---|---|---|---|---|---|---|---|
| Example 3-15 | Production Example 3-6 | EDTMP•5Na | Polymerization | 200 | EDTMP•5Na | After heating treatment | 800 | DHT-6 | After addition of additive 2 | 0.3 |
| Example 3-16 | Production Example 3-6 | EDTMP•5Na | Polymerization | 200 | DTPA•3Na | After heating treatment | 300 | DHT-6 | After addition of additive 2 | 0.3 |
| Example 3-17 | Production Example 3-9 | EDTMP•5Na | Polymerization | 1000 | DTPA•3Na | After heating treatment | 1000 | DHT-6 | After addition of additive 2 | 0.3 |

TABLE 3-1

| | Water absorbent resin | Additive 1 Kind | Additive 1 Amount of addition ppm | Additive 2 Kind | Additive 2 Amount of addition ppm | Additive 3 Kind | Additive 3 Amount of addition ppm |
|---|---|---|---|---|---|---|---|
| Comparative Example 3-1 | Production Example 3-2 | — | — | — | — | — | — |
| Comparative Example 3-2 | Production Example 3-1 | — | — | — | — | — | — |
| Comparative Example 3-3 | Production Example 3-4 | DTPA•3Na | 50 | — | — | — | — |
| Example 3-1 | Production Example 3-3 | DTPA•3Na | 50 | DTPA•3Na | 100 | DHT-6 | 0.3 |
| Example 3-2 | Production Example 3-4 | DTPA•3Na | 50 | DTPA•3Na | 100 | DHT-6 | 0.3 |
| Example 3-3 | Production Example 3-4 | DTPA•3Na | 50 | DTPA•3Na | 300 | DHT-6 | 0.3 |
| Example 3-4 | Production Example 3-3 | DTPA•3Na | 50 | DTPA•3Na + SBS | 50 + 3000 | DHT-6 | 0.3 |
| Example 3-5 | Production Example 3-4 | DTPA•3Na | 50 | EDTMP•5Na | 220 | DHT-6 | 0.3 |
| Example 3-6 | Production Example 3-6 | EDTMP•5Na | 200 | — | — | DHT-6 | 0.3 |
| Example 3-7 | Production Example 3-7 | EDTMP•5Na | 500 | — | — | DHT-6 | 0.3 |
| Comparative Example 3-4 | Production Example 3-6 | EDTMP•5Na | 200 | — | — | — | — |
| Comparative Example 3-5 | Production Example 3-6 | EDTMP•5Na | 200 | — | — | AEROSIL | 0.3 |
| Comparative Example 3-6 | Production Example 3-5 | EDTMP•5Na | 200 | — | — | AEROSIL | 0.3 |
| Example 3-8 | Production Example 3-5 | EDTMP•5Na | 200 | DTPA•3Na | 100 | DHT-6 | 0.3 |
| Example 3-9 | Production Example 3-7 | EDTMP•5Na | 500 | DTPA•3Na | 100 | DHT-6 | 0.3 |
| Example 3-10 | Production Example 3-6 | EDTMP•5Na | 200 | DTPA•3Na + $NaH_2PO_4$ | 300 + 4400 | DHT-6 | 0.3 |
| Example 3-11 | Production Example 3-6 | EDTMP•5Na | 200 | SBS | 5000 | DHT-6 | 0.3 |
| Example 3-12 | Production Example 3-8 | DTPA•3Na | 1000 | — | — | DHT-6 | 0.3 |
| Example 3-13 | Production Example 3-2 | — | — | DTPA•3Na | 1000 | DHT-6 | 0.3 |
| Example 3-14 | Production Example 3-9 | EDTMP•5Na | 1000 | — | — | DHT-6 | 0.3 |
| Example 3-15 | Production Example 3-6 | EDTMP•5Na | 200 | EDTMP•5Na | 800 | DHT-6 | 0.3 |
| Example 3-16 | Production Example 3-6 | EDTMP•5Na | 200 | DTPA•3Na | 300 | DHT-6 | 0.3 |
| Example 3-17 | Production Example 3-9 | EDTMP•5Na | 1000 | DTPA•3Na | 1000 | DHT-6 | 0.3 |

| | CRC g/g | AAP g/g | Blocking ratio, mass % | Deteriorated soluble component % | L-as/Fe resistance % | Amount of dust mg/kg |
|---|---|---|---|---|---|---|
| Comparative Example 3-1 | 38.6 | 30.0 | 100 | 75 | X | |
| Comparative Example 3-2 | 40.2 | 28.0 | 100 | 72 | X | |

TABLE 3-1-continued

| | | | | | | |
|---|---|---|---|---|---|---|
| Comparative Example 3-3 | 38.0 | 31.0 | 100 | 48 | X | |
| Example 3-1 | 40.0 | 28.0 | 0 | 22 | X | 27 |
| Example 3-2 | 38.0 | 31.0 | 0 | 23 | X | |
| Example 3-3 | 37.6 | 31.4 | 0 | 20 | ○ | |
| Example 3-4 | 40.0 | 28.2 | 0 | 19 | ○ | |
| Example 3-5 | 38.0 | 30.6 | 0 | 22 | Δ | |
| Example 3-6 | 38.2 | 30.6 | 0 | 43 | X | |
| Example 3-7 | 38.0 | 30.8 | 0 | 30 | X | |
| Comparative Example 3-4 | 38.0 | 31.3 | 100 | 21 | X | |
| Comparative Example 3-5 | 37.7 | 25.6 | 0 | 23 | Δ | 174 |
| Comparative Example 3-6 | 40.2 | 22.5 | | 23 | Δ | |
| Example 3-8 | 39.9 | 28.1 | 0 | 18 | Δ | |
| Example 3-9 | 38.2 | 30.9 | 0 | 17 | Δ | |
| Example 3-10 | 37.5 | 31.0 | 0 | 17 | Δ | |
| Example 3-11 | 38.2 | 31.0 | 0 | 23 | ○ | |
| Example 3-12 | 38 | 31 | 0 | 21 | ○ | |
| Example 3-13 | 37.6 | 30.7 | 0 | 19 | ○ | |
| Example 3-14 | 37.6 | 30.6 | 0 | 21 | Δ | |
| Example 3-15 | 37.2 | 30.1 | 0 | 22 | Δ | |
| Example 3-16 | 37.5 | 31 | 0 | 20 | Δ | |
| Example 3-17 | 38.1 | 31.2 | 0 | 20 | Δ | |

(Summary of Table 3-2)

As can be seen from the above tables, it is understood that the water absorbing agents of the present invention have low blocking ratio against moisture absorptions, and urine resistance is suppressed by addition of a chelating agent.

Production Example 4-1

In 5500 g of an aqueous solution of sodium acrylate having the neutralization rate of 75% by mole (monomer concentration: 35% by mass), 0.38 g of trimethylolpropane triacrylate (molecular weight 296) (0.006% by mole relative to the monomer) was dissolved, and a monomer aqueous solution (a) was prepared. Subsequently, the monomer aqueous solution was degassed for 30 minutes in a nitrogen gas atmosphere.

Next, the monomer aqueous solution (a) was introduced into a reactor produced by providing a lid to a double blade type jacketed kneader made of stainless steel with an internal capacity of 10 L and having two sigma-shaped blades. Nitrogen gas was blown into the reactor while the liquid temperature was maintained at 30° C., and the reactor was purged with nitrogen such that the dissolved oxygen in the system would be 1 ppm or less.

Subsequently, 24.6 g of a 10 mass % aqueous solution of sodium persulfate and 21.8 g of a 0.2 mass % aqueous solution of L-ascorbic acid were separately added to the monomer aqueous solution (a) with stirring, and polymerization was initiated after about 1 minute. While the produced water-containing gel-like cross-linked polymer (a) was crushed, polymerization was performed at 30° C. to 90° C., and when 60 minutes had passed from the initiation of polymerization, a water-containing gel-like cross-linked polymer (a) was taken out from the reactor. The water-containing gel-like cross-linked polymer (a) thus obtained was subjected to grain refining to particles having a particle diameter of about 5 mm.

The water-containing gel-like cross-linked polymer (a) thus subjected to grain refining described above was spread on a wire gauze having a mesh size of 300 μm (50-mesh), and dried under hot air for 45 minutes at 180° C. Subsequently, the cross-linked polymer was pulverized with a roll mill, and was classified with JIS standard sieves having mesh sizes of 850 μm and 150 μm. Through this series of operations, a water absorbent resin powder (a), which was a water absorbent resin (solid content 4.0% by mass) in an irregularly shaped crushed form, was obtained. The CRC (water absorption capacity without load) of the water absorbent resin powder (a) was 53.0 [g/g].

Next, the water absorbent resin powder (a) was transferred into a rotary mixer manufactured by Deutsche Lödige GmbH, and an aqueous solution of surface cross-linking agent including 0.025 parts by mass of ethylene glycol diglycidyl ether (trade name: DENACOL EX-810, manufactured by Nagase ChemteX Corp.), 0.3 parts by mass of ethylene carbonate (melting point 36° C.), 0.5 parts by mass of 1,2-propanediol (melting point−59° C.), and 3.0 parts by mass of water, was uniformly mixed relative to 100 parts by mass of the water absorbent resin powder (a). The mixture was heat treated for 40 minutes at 175° C. Thereafter, the mixture was passed through a JIS standard sieve having a mesh size of 850 μm, and thereby water absorbent resin particles (surface cross-linked water absorbent resin) (4-1) were obtained.

Production Example 4-2

In polypropylene containers having an inner diameter of 80 mm and a capacity of 1 liter and covered with expanded polystyrene, which is a thermal insulating material, a solution (A) in which 291 g of acrylic acid, 0.43 g (0.02% by mole relative to the carboxyl group-containing unsaturated monomer) of polyethylene glycol diacrylate (molecular weight 523) as an internal cross-linking agent, 1.80 g of a 1.0 mass % aqueous solution of pentasodium diethylenetriaminepentaacetate, and 3.60 g of a 1.0 mass % acrylic acid solution of IRGACURE (registered trademark) 184 were mixed, and a solution (B) in which 247 g of a 48.5 mass % aqueous solution of sodium hydroxide and 255 g of ion-exchanged water adjusted to 50° C. were mixed, were prepared. A monomer aqueous solution (C) was obtained by rapidly adding the solution (B) to the solution (A) which was being stirred at 800 rpm using a magnetic stirrer having a length of 5 cm, and mixing the solutions. The liquid temperature of the monomer aqueous solution (C) was increased to about 100° C. due to the heat of neutralization and the heat of dissolution. The neutralization rate of acrylic acid was 73.5% by mole.

Next, 1.8 g of a 3 mass % aqueous solution of sodium persulfate was added to the monomer aqueous solution (C), and the mixture was stirred for about 1 second, and then the mixture was poured immediately into a vat type container made of stainless steel and lined with TEFLON (registered trademark) on the inner surface, in an open system. Furthermore, ultraviolet was irradiated simultaneously with pouring of the monomer aqueous solution into the vat type container made of stainless steel.

As soon as the monomer aqueous solution was poured into the vat, polymerization was initiated (temperature at the time of initiation of polymerization 98° C.), and polymerization reached the peak temperature within about 1 minute. After 3 minutes, irradiation of ultraviolet was terminated, and a hydrous polymerization product was taken out. This series of operations were carried out in an open system in air.

The obtained hydrous polymer was crushed by a meat chopper (meat-chopper type: 12VR-400KSOX, Iizuka Kogyo, Inc., die orifice diameter: 6.4 mm, number of holes: 38, die thickness 8 mm), and subjected to grain refining, crushed hydrous polymer particles were obtained (mass average particle size 1000 μm).

These subjected to grain refining, crushed hydrous polymer particles were spread on a 50-mesh (mesh size 300 μm) wire gauze, and were subjected to hot air drying at 180° C. The dried product was pulverized with a roll mill, and the particles were classified with JIS standard sieves having mesh size of 850 μm and a mesh size of 150 μm. Thereby, a water absorbent resin powder (b), which was a water absorbent resin (solid content 96% by mass) in an irregularly shaped crushed form, was obtained. The CRC (water absorption capacity without load) of the water absorbent resin powder (b) was 47.3 [g/g].

Next, the water absorbent resin powder (b) described above was transferred to a rotary mixer manufactured by Deutsche Lödige GmbH, and an aqueous solution of surface cross-linking agent including 0.015 parts by mass of ethylene glycol diglycidyl ether, 1.0 parts by mass of propylene glycol, and 3.0 parts by mass of water, was uniformly mixed relative to 100 parts by mass of the water absorbent resin powder (b). The mixture was heat treated for 45 minutes at 100° C. Thereafter, the particle size of the water absorbent resin powder was adjusted using a JIS standard sieve having a mesh size of 850 μm, and thereby water absorbent resin particles (4-2) having the surface cross-linked were obtained.

Production Example 4-3

Water absorbent resin particles (4-3) having the surface cross-linked were obtained by performing the same operation as in Production Example 4-2, except that the amount of ethylene glycol diglycidyl ether in Production Example 4-2 was changed to 0.03 parts by mass.

Example 4-1

0.3 parts by mass of a hydrotalcite having a Mg/Al ratio of 3.0/1 (product name: DHT-6, manufactured by Kyowa Chemical Industry Co., Ltd.) were mixed relative to 100 parts by mass of the water absorbent resin particles (4-1) obtained in Production Example 4-1. Regarding the mixing, 30 g of the water absorbent resin was introduced into a mayonnaise bottle having a capacity of 225 ml together with the hydrotalcite, and the content was mixed by vibration (for 3 minutes at room temperature) of a paint shaker (manufactured by Toyo Seiki Seisakusho Co., Ltd.). Thus, a water absorbing agent (4-1) was obtained. The performance of the water absorbing agent (4-1) is presented in the following Table 4-1. Furthermore, the results of measuring the particle size of the water absorbing agent (4-1) are presented in Table 4-2.

Example 4-2

0.3 parts by mass of a hydrotalcite having a Mg/Al ratio of 2.1/1 (product name: DHT-4H, manufactured by Kyowa Chemical Industry Co., Ltd.) were mixed relative to 100 parts by mass of the water absorbent resin particles (4-1) obtained in Production Example 4-1. Regarding the mixing, 30 g of the water absorbent resin was introduced into a mayonnaise bottle having a capacity of 225 ml together with the hydrotalcite, and the content was mixed by vibration (for 3 minutes at room temperature) of a paint shaker (manufactured by Toyo Seiki Seisakusho Co., Ltd.). Thus, a water absorbing agent (4-2) was obtained. The performance of the water absorbing agent (4-2) is presented in the following Table 4-1. Furthermore, the results of measuring the particle size of the water absorbing agent (4-2) are presented in Table 4-2.

Example 4-3

0.3 parts by mass of the hydrotalcite used in Example 4-1 were mixed in the same manner as in Example 4-1, relative to 100 parts by mass of the water absorbent resin particles (4-2) obtained in Production Example 4-2, and thus a water absorbing agent (4-3) was obtained. The performance of the water absorbing agent (4-3) is presented in the following Table 4-1. Furthermore, the results of measuring the particle size of the water absorbing agent (4-3) are presented in Table 4-2.

Example 4-4

0.3 parts by mass of a hydrotalcite having a Mg/Al ratio of 2.1/1 (product name: HT-1-NC, manufactured by Sakai Chemical Industry Co., Ltd.) were mixed in the same manner as in Example 4-1, relative to 100 parts by mass of the water absorbent resin particles (4-2) obtained in Production Example 4-2, and thus a water absorbing agent (4-4) was obtained. The performance of the water absorbing agent (4-4) is presented in the following Table 4-1. Furthermore, the results of measuring the particle size of the water absorbing agent (4-4) are presented in Table 4-2.

Example 4-5

100 parts by mass of the water absorbent resin particles (4-3) obtained in Production Example 4-3 and 0.3 parts by mass of the hydrotalcite used in Example 4-1 were mixed in the same manner as in Example 4-1, and thus a water absorbing agent (4-5) was obtained. The performance of the water absorbing agent (4-5) is presented in the following Table 4-2.

Example 4-6

100 parts by mass of the water absorbent resin particles (4-3) obtained in Production Example 4-3 and 0.3 parts by mass of the hydrotalcite used in Example 4-2 were mixed in the same manner as in Example 4-1, and thus a water absorbing agent (4-6) was obtained. The performance of the water absorbing agent (4-6) is presented in the following Table 4-2.

Example 4-7

The water absorbent resin powder (4-1) obtained in Production Example 4-1 was further pulverized with a roll mill, and the powder was classified with JIS standard sieves having mesh size of 850 μm and mesh size of 150 μm. Through this series of operations, a water absorbent resin powder (c) was obtained. Meanwhile, the CRC (water absorption capacity without load) of the water absorbent resin powder (c) was 53.0 [g/g].

Next, a surface treating agent including 0.025 parts by mass of ethylene glycol diglycidyl ether (trade name: DENACOL EX-810, manufactured by Nagase ChemteX Corp.), 0.3 parts by mass of ethylene carbonate (melting point 36° C.), 0.5 parts by mass of 1,2-propanediol (melting point−59° C.), and 3.0 parts by mass of water, was uniformly mixed relative to 100 parts by mass of the water absorbent resin powder (c). The mixture was heat treated for 40 minutes at 175° C. Thereafter, the mixture was passed through a JIS standard sieve having a mesh size of 850 μm, and thereby water absorbent resin particles (4-4) were obtained.

0.3 parts by mass of the hydrotalcite used in Example 4-2 were mixed in the same manner as in Example 4-1, relative to 100 parts by mass of the water absorbent resin particles (4-4), and thus a water absorbing agent (4-7) was obtained. The performance of the water absorbing agent (4-7) is presented in the following Table 4-2.

Comparative Example 4-1

The water absorbent resin particles (4-1) described in Production Example 4-1 are regarded as a comparative water absorbing agent (4-1), and various physical properties thereof are presented in Table 4-1. Furthermore, the results for measuring the particle size of the comparative water absorbing agent (4-1) are presented in Table 4-2.

Comparative Example 4-2

The water absorbent resin particles (4-2) described in Production Example 4-2 are regarded as a comparative water absorbing agent (4-2), and various physical properties thereof are presented in Table 4-1. Furthermore, the results for measuring the particle size of the comparative water absorbing agent (4-2) are presented in Table 4-2.

Comparative Example 4-3

The water absorbent resin particles (4-3) described in Production Example 4-3 are regarded as a comparative water absorbing agent (4-3), and various physical properties thereof are presented in Table 4-2.

Comparative Example 4-4

100 parts by mass of the water absorbent resin particles (4-2) obtained in Production Example 4-2 and 0.3 parts by mass of silica (product name: AEROSIL 200CF, manufactured by Nippon Aerosil Co., Ltd.) were mixed in the same manner as in Example 4-1, and thus a comparative water absorbing agent (4-4) was obtained. The performance of the comparative water absorbing agent (4-4) is presented in the following Table 4-1. Furthermore, the results for measuring the particle size of the comparative water absorbing agent (4-4) are presented in Table 4-2.

Comparative Example 4-5

0.3 parts by mass of magnesium oxide (product name: 500-04R, manufactured by Kyowa Chemical Industry Co., Ltd.) were mixed in the same manner as in Example 4-1, relative to 100 parts by mass of the water absorbent resin particles (4-2) obtained in Production Example 4-2, and thus a comparative water absorbing agent (4-5) was obtained. The performance of the comparative water absorbing agent (4-5) is presented in the following Table 4-2.

Comparative Example 4-6

0.3 parts by mass of a magnesium aluminate having a Mg/Al ratio of 0.5/1 (Sigma-Aldrich Co.) were mixed in the same manner as in Example 1, relative to 100 parts by mass of the water absorbent resin particles (4-2) obtained in the Production Example 4-2, and thus a comparative water absorbing agent (4-6) was obtained. The performance of the comparative water absorbing agent (4-6) is presented in the following Table 4-2.

(Method for Evaluating Absorbent Speed (Core Acquisition) and Amount of Rewetting of Absorbent Articles)

An absorbent article that should be measured was produced by the method described below. That is, first, 60 parts by weight of a water absorbing agent (or a water absorbent resin) and 40 parts by weight of wood pulverized pulp were subjected to air papermaking using a batch type air papermaking apparatus on a 400-mesh wire screen (mesh size 38 μm), and thereby, a web having a size of 120 mm×400 mm was formed. Furthermore, this web was pressed using a hydraulic pressing machine, and thereby an absorbent body having a density of about 0.1 g/cm$^3$ was obtained. Subsequently, this absorbent body was provided with a liquid-impermeable back sheet and a liquid-permeable top sheet, and thus an absorbent article was obtained.

Then, a 20-mesh wire mesh having a size of 120 mm×400 mm was disposed on the absorbent article described above, and a load of 20 g/cm$^2$ (1.9 kPa) was uniformly applied over the entire absorbent article. Also, a cylinder having a diameter of 70 mm and a height of 100 mm was made to stand vertically by firmly pressing the cylinder at the central area of the absorbent body. Subsequently, 75 g of a test liquid at 37° C. was poured into the cylinder at a rate of 7 ml/sec, and the time period from the time point at which pouring of the test liquid was started to the time point at which the test liquid was all absorbed by the absorbent body, was measured, and this value was designated as the absorbent speed (seconds) of first round. Thereafter, the same measurement was repeated three times at an interval of 60 minutes using the absorbent body used in the measurement described above, and the absorbent speed (seconds) of second round, the absorbent speed (seconds) of third round, and the absorbent speed (seconds) of fourth round were measured. Thirty minutes after the test liquid of the fourth round was introduced, the load was removed from the absorbent article, and a paper towel (manufacturer: Oji Paper Co., Ltd., Kitchen Towel Extra Dry, cut to a size of 120 mm×450 mm and 30 sheets were overlapped) was mounted on the absorbent article, while a load of 43 g/cm$^2$ (4.2 kPa) was left to stand thereon for 1 minute. The amount of liquid absorbed by the paper towel was determined by measuring the weight change of the paper towel, and this was designated as the amount of rewetting (g). Meanwhile, a 0.9 mass % aqueous solution of sodium chloride was used as the test liquid.

Example 4-8

The evaluation of the absorbent speed (core acquisition) and the amount of rewetting of an absorbent article was carried out using the water absorbing agent (4-3) obtained in Example 4-3. The results of evaluation of the absorbent body are presented in Table 4-3.

Comparative Example 4-7

The evaluation of the absorbent speed (core acquisition) and the amount of rewetting of an absorbent article was carried out using the water absorbing agent (4-4) obtained in Example 4-4. The results of evaluation of the absorbent body are presented in Table 4-3.

TABLE 4-1

| | Water absorbing agent | Water absorbent resin | Additive Kind | Additive Mg/Al ratio | Additive Amount of addition (wt %) | Proportion of 150 to 850 μm (wt %) | CRC (g/g) | AAP (g/g) | Blocking ratio against moisture absorption (%) | Amount of dust (mg/kg) |
|---|---|---|---|---|---|---|---|---|---|---|
| Example 4-1 | Water absorbing agent (4-1) | Water absorbent resin (4-1) | DHT-6 | 3.0/1 | 0.3 | 99 | 42.9 | 28.3 | 0 | 27 |
| Example 4-2 | Water absorbing agent (4-2) | Water absorbent resin (4-1) | DHT-4H | 2.1/1 | 0.3 | 99 | 42.9 | 27.8 | 0 | |
| Example 4-3 | Water absorbing agent (4-3) | Water absorbent resin (4-2) | DHT-6 | 3.0/1 | 0.3 | 97.6 | 37.6 | 30.9 | 0 | |
| Example 4-4 | Water absorbing agent (4-4) | Water absorbent resin (4-2) | HT-1-NC | 2.1/1 | 0.3 | 97.6 | 37.6 | 30.6 | 0 | 35 |
| Example 4-5 | Water absorbing agent (4-5) | Water absorbent resin (4-3) | DHT-6 | 3.0/1 | 0.3 | 97.7 | 34.5 | 31.2 | 0 | 30 |
| Example 4-6 | Water absorbing agent (4-6) | Water absorbent resin (4-3) | DHT-4H | 2.1/1 | 0.3 | 97.7 | 34.5 | 30.9 | 0 | |
| Example 4-7 | Water absorbing agent (4-7) | Water absorbent resin (4-4) | DHT-4H | 2.1/1 | 0.3 | 92.6 | 42.9 | 28.1 | 0 | |
| Comparative Example 4-1 | Comparative water absorbing agent (4-1) | Water absorbent resin (4-1) | — | — | 0 | 99.0 | 43.0 | 29.0 | 100 | 46 |
| Comparative Example 4-2 | Comparative water absorbing agent (4-2) | Water absorbent resin (4-2) | — | — | 0 | 97.6 | 37.6 | 31.3 | 100 | 65 |
| Comparative Example 4-3 | Comparative water absorbing agent (4-3) | Water absorbent resin (4-3) | — | — | 0 | 97.7 | 34.5 | 31.9 | 100 | 50 |
| Comparative Example 4-4 | Comparative water absorbing agent (4-4) | Water absorbent resin (4-2) | AEROSIL | AEROSIL | 0.3 | 97.6 | 37.7 | 25.6 | 0 | 176 |
| Comparative Example 4-5 | Comparative water absorbing agent (4-5) | Water absorbent resin (4-2) | Mg oxide | Mg oxide | 0.3 | 97.6 | 37.5 | 30.6 | 99 | |
| Comparative Example 4-6 | Comparative water absorbing agent (4-6) | Water absorbent resin (4-2) | Mg aluminate | 0.5/1 | 0.3 | 97.6 | 37.9 | 28.6 | 43 | 210 |

TABLE 4-2

| | | Water absorbing agent | | | | | | Comparative water absorbing agent | | | |
|---|---|---|---|---|---|---|---|---|---|---|---|
| | | 4-1 | 4-2 | 4-3 | 4-4 | 4-5 | 4-6 | 4-1 | 4-2 | 4-3 | 4-4 |
| on 850 μm | (%) | 0.0 | 0.0 | 0.0 | 0.0 | 0.0 | 0.0 | 0.0 | 0.0 | 0.0 | 0.0 |
| on 600 μm | (%) | 20.0 | 20.8 | 0.8 | 0.8 | 5.0 | 5.2 | 19.7 | 0.7 | 4.9 | 22.2 |
| on 500 μm | (%) | 23.9 | 24.2 | 10.1 | 10.0 | 17.2 | 18.2 | 21.2 | 9.8 | 17.1 | 23.9 |
| on 300 μm | (%) | 35.7 | 36.7 | 58.2 | 59.1 | 53.7 | 53.1 | 37.5 | 56.8 | 54.9 | 35.4 |
| on 150 μm | (%) | 19.0 | 17.3 | 29.0 | 28.4 | 22.3 | 22.3 | 20.6 | 30.6 | 22.2 | 17.7 |
| on 45 μm | (%) | 1.4 | 0.8 | 2.0 | 1.7 | 1.7 | 1.1 | 0.9 | 2.1 | 0.9 | 0.8 |
| thru 45 μm | (%) | 0.0 | 0.0 | 0.0 | 0.0 | 0.1 | 0.1 | 0.1 | 0.0 | 0.0 | 0.0 |
| D50 | (μm) | 462 | 470 | 347 | 349 | 383 | 387 | 445 | 343 | 385 | 476 |
| σζ | | 0.40 | 0.38 | 0.33 | 0.32 | 0.35 | 0.35 | 0.41 | 0.34 | 0.34 | 0.38 |

TABLE 4-3

|  | Water absorbing agent | Absorbent speed of absorbent body | | | | Amount of re-wetting (g) |
|---|---|---|---|---|---|---|
|  |  | First round (sec) | Second round (sec) | Third round (sec) | Fourth round (sec) |  |
| Example 4-8 | Water absorbing agent (4-3) | 17 | 34 | 37 | 39 | 25 |
| Comparative Example 4-8 | Comparative water absorbing agent (4-4) | 18 | 34 | 39 | 41 | 36 |

TABLE 5-1

|  | Additive 1 | | Additive 3 | | | Water-soluble magnesium ion | |
|---|---|---|---|---|---|---|---|
|  | Kind | Amount of addition ppm | Kind | Amount of addition, mass % | Y1 | Measured value ppb | Relative amount of addition ppm |
| Comparative Example 2-6 | EDTMP•5Na | 200 | Mg hydroxide | 0.3 | 39 | 55142 | 15.8 |
| Example 2-4 | EDTMP•5Na | 200 | DHT-4H | 0.3 | 26.2 | 1483 | 0.43 |
| Example 2-5 | EDTMP•5Na | 200 | HT-1-NC | 0.3 | 24.8 | 897 | 0.25 |
| Comparative Example 2-5 | EDTMP•5Na | 200 | AEROSIL | 0.3 | 21 | — | — |

Table 5-1 shows the comparison between coloration resistance and the results of water-soluble magnesium ion measurement and the reduced amount (relative amount of addition) in the case of being added to water absorbing agents. As shown in Table 5-1, it is understood that as the relative amount of addition of water-soluble magnesium ion increases, the YI is increased.

The present patent application is based on Japanese Patent Application No. 2012-219517, filed on Oct. 1, 2012, and Japanese Patent Application Nos. 2013-184485 and 2013-184487, filed on Sep. 5, 2013, the entire disclosures of which are incorporated herein by reference.

The invention claimed is:

1. A method for producing a water absorbing agent, the method comprising:
   a surface cross-linking step; and
   a multi-component metal compound adding step of adding a multi-component metal compound, which has a hydrotalcite structure and contains a hydroxyl group and two kinds of metal cations that are divalent and trivalent, to a polyacrylic acid (salt)-based water absorbent resin powder in an amount of 0.01% by mass to 5% by mass, wherein the volume average particle size of the multi-component metal compound is 2 μm or less.

2. The production method according to claim 1, wherein in the multi-component metal compound adding step, the water absorbent resin powder and the multi-component metal compound are dry mixed.

3. The production method according to claim 1, wherein the surface cross-linking step is carried out in a preceding step and/or a subsequent step of the multi-component metal compound adding step.

4. The production method according to claim 1, further comprising a chelating agent adding step of adding a chelating agent.

5. The production method according to claim 1, wherein the addition of a chelating agent is carried out in a step for preparing an aqueous solution of an acrylic acid (salt)-based monomer or in an aqueous solution polymerization step, and at least one selected from a chelating agent, an inorganic reducing agent, an α-hydroxycarboxylic acid, and a phosphorus compound is added after the surface cross-linking step and before the multi-component metal compound adding step.

6. The method according to claim 1, wherein the volume average particle size of the multi-component metal compound is greater than 0.1 μm and less than or equal to 2 μm.

7. The method according to claim 1, wherein the volume average particle size of the multi-component metal compound is greater than or equal to 0.3 μm and less than or equal to 2 μm.

8. A water absorbing agent comprising a polyacrylic acid (salt)-based water absorbent resin as a main component and having a blocking ratio against moisture absorption of 0% to 30% by mass, the water absorbing agent comprising 0.01% by mass to 5% by mass a multi-component metal compound which has a hydrotalcite structure and contains a hydroxyl group and two kinds of metal cations that are divalent and trivalent, wherein the volume average particle size of the multi-component metal compound is 2 μm or less.

9. The water absorbing agent according to claim 8, wherein the absorption capacity under load (AAP) is 20 (g/g) or more.

10. The water absorbing agent according to claim 8, further comprising a chelating agent.

11. The water absorbing agent according to claim 8, wherein the volume average particle size of the multi-component metal compound is greater than 0.1 μm and less than or equal to 2 μm.

12. The water absorbing agent according to claim 8, wherein the volume average particle size of the multi-component metal compound is greater than or equal to 0.3 μm and less than or equal to 2 μm.

* * * * *